(12) United States Patent
Lai et al.

(10) Patent No.: US 7,622,113 B2
(45) Date of Patent: Nov. 24, 2009

(54) MONOCLONAL ANTIBODIES THAT BIND OR NEUTRALIZE DENGUE VIRUS

(75) Inventors: Ching-Juh Lai, Bethesda, MD (US); Robert H. Purcell, Gaithersburg, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 241 days.

(21) Appl. No.: 10/582,006

(22) PCT Filed: Dec. 3, 2004

(86) PCT No.: PCT/US2004/040674

§ 371 (c)(1),
(2), (4) Date: Jun. 7, 2006

(87) PCT Pub. No.: WO2005/056600

PCT Pub. Date: Jun. 23, 2005

(65) Prior Publication Data

US 2007/0134256 A1 Jun. 14, 2007

Related U.S. Application Data

(60) Provisional application No. 60/528,161, filed on Dec. 8, 2003, provisional application No. 60/541,676, filed on Feb. 4, 2004, provisional application No. 60/552,528, filed on Mar. 12, 2004, provisional application No. 60/574,492, filed on May 26, 2004, provisional application No. 60/624,261, filed on Nov. 1, 2004.

(51) Int. Cl.
*A61K 39/42* (2006.01)
*A61K 49/00* (2006.01)
*C07K 16/10* (2006.01)
*C12N 15/13* (2006.01)
*C12N 5/10* (2006.01)
*C12N 1/21* (2006.01)

(52) U.S. Cl. .............. 424/133.1; 424/141.1; 424/141.2; 424/147.1; 424/9.1; 530/387.3; 530/388.1; 435/328; 435/339; 435/252.3; 435/5; 536/23.53

(58) Field of Classification Search ........................ None
See application file for complete search history.

(56) References Cited

U.S. PATENT DOCUMENTS 6,184,024 B1 2/2001 Lai et al.
7,282,205 B2 * 10/2007 Schofield et al. ......... 424/141.1

FOREIGN PATENT DOCUMENTS

WO WO 99/55369 A1 11/1999

OTHER PUBLICATIONS

Pupo-Antunez et al. Hybridoma 20:35-41, 2001.*
Kellerman et al. Current Opinion in BIotechnology 13:593-597, 2002.*
Paul, Fundamental Immunology, (textbook), 1993, pp. 292-295. Lippincott-Raven Publishers, Philadelphai, PA.*
Pupo-Antunez et al (Hybridoma 20:35-42, 2001).*
Gavilondo et al (BioTechniques 29:128-145, 2000).*
Scherer et al (American Journal of Tropical Medicine and Hygiene 27:590-599, 1978, abstract only cited).*
Sanna et al (Immunotechnology 4:185-188, 1999).*
Men et al, Journal of Virology 78:4665-4674, 2004.*
Allen, J.M. et al. (1989) "Isolation and expression of functional high-affinity Fc receptor complementary DNAs." *Science* 243:378-381.
Ames, R.S. et al. (1995) "Conversion of murine fabs isolated from a combinatorial phage display library to full length immunoglobulins" *J. Immunol. Methods* 184:177-186.
Armour, K.L. et al. (1999) "Recombinant human IgG molecules lacking Fcγ receptor I binding and monocyte triggering activities" *Eur. J. Immunol.* 29:2613-2624.
Barbas, C.F. et al. (1991) "Assembly of combinatorial antibody libraries on phage surfaces: the gene III site." *PNAS USA* 88:7978-7982.
Barbas, C.F. et al. (1994) "In vitro evolution of a neutralizing human antibody to human immunodeficiency virus type 1 to enhance affinity and broaden strain cross reactivity." *PNAS USA* 91:3809-3813.
Brandriss, M.W. et al. (1986) "Lethal 17D yellow fever encephalitis in mice. I. Passive protection by monoclonal antibodies to the envelope proteins of 17D yellow fever and dengue 2 viruses." *J. Gen. Virol.* 67:229-234.
Bray, M. et al. (1991) "Dengue virus premembrane and membrane proteins elicit a protective immune response." *Virology* 185:505-508.
Burton, D.R. et al. (1994) "Efficient neutralization of primary isolates of HIV-1 by a recombinant human monoclonal antibody" *Science* 266:1024-1027.
Chambers, T.J. et al. (1990) "Flavivirus genome organization, expression, and replication" *Annu. Rev. Microbiol.* 44:649-688.
Chappel, M.S. et al. (1991) "Identification of the Fcγ receptor class I binding site in human IgG through the use of recombinant IgG1/IgG2 hybrid and point-mutated antibodies." *PNAS USA* 88:9036-9040.
Cox, J.P. et al. (1994) "A directory of human germ-line Vκ segments reveals a strong bias in their usage." *Eur. J. Immunol.* 24:827-836.

(Continued)

*Primary Examiner*—Mary E Mosher
(74) *Attorney, Agent, or Firm*—Edwards Angell Palmer & Dodge LLP; Peter F. Corless

(57) ABSTRACT

The present invention relates to monoclonal antibodies that bind or neutralize dengue type 1, 2, 3, and/or 4 virus. The invention provides such antibodies, fragments of such antibodies retaining dengue virus-binding ability, fully human or humanized antibodies retaining dengue virus-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

26 Claims, 20 Drawing Sheets

OTHER PUBLICATIONS

Crowe, J.E., Jr. et al. (1994) "Recombinant human respiratory syncytial virus (RSV) monoclonal antibody Fab is effective therapeutically when introduced directly into the lungs of RSV-infected mice." *PNAS USA* 91:1386-1390.

Doral H. et al. (1987) "The effect of dihydrofolate reductase-mediated gene amplification on the expression of transfected immunoglobulin genes." *J. Immunol.* 139:4232-4241.

Durbin, A.P. et al. (2001) "Attenuation and immunogenicity in humans of a live dengue virus type 4 vaccine candidate with a 30 nucleotide deletion in its 3'-untranslated region." *Am. J. Trop. Med. Hyg.* 65:405-413.

Ehrlich, P.H. et al. (1988) "Further characterization of the fate of human monoclonal antibodies in rhesus monkeys." *Hybridoma* 7:385-395.

Ehrlich, P.H. et al. (1990) "Potential of primate monoclonal antibodies to substitute for human antibodies: nucleotide sequence of chimpanzee Fab fragments." *Hum. Antib. Hybrid.* 1:23-26.

Ehrlich, P.H. et al. (1991) "Nucleotide sequence of chimpanzee Fc and hinge regions." *Mol. Immunol.* 28:319-322.

Falgout, B. et al. (1990) "Immunization of mice with recombinant vaccinia virus expressing authentic dengue virus nonstructural protein NS1 protects against lethal dengue virus encephalitis." *J. Virol.* 64:4356-4363.

Falgout, B. et al. (1991) "Both nonstructural proteins NS2B and NS3 are required for the proteolytic processing of dengue virus nonstructural proteins." *J. Virol.* 65:2467-2475.

Gentry, M.K. et al. 1982 "Identification of distinct antigenic determinants on dengue 2 virus using monoclonal antibodies." *Am. J. Trop. Med. Hyg.* 31:548-555.

Glamann, J. et al. (1998) "Simian immunodeficiency virus (SIV) envelope-specific Fabs with high-level homologous neutralizing activity: recovery from a long-term-nonprogressor SIV-infected macaque." *J. Virol.* 72:585-592.

Goncalvez, A.P. et al. (2004) "Chimpanzee fab fragments and a derived humanized immunoglobulin G1 antibody that efficiently cross-neutralize dengue type 1 and type 2 viruses." *J. Virol.* 78:12910-12918.

Goncalvez, A.P. et al. (2004) "Epitope determinants of a chimpanzee Fab antibody that efficiently cross-neutralizes dengue type 1 and type 2 viruses map to inside and in close proximity to fusion loop of the dengue type 2 virus envelope glycoprotein." *J. Virol.* 78:12919-12928.

Gould, E.A. et al. (1986) "Neutralizing (54K) and non-neutralizing (54K and 48K) monoclonal antibodies against structural and non-structural yellow fever virus proteins confer immunity in mice." *J. Gen. Virol.* 67:591-595.

Halstead, S. (1982) "Immune enhancement of viral infection." *Prog. Allergy* 31:301-364.

Heinz, F.X. (1986) "Epitope mapping of flavivirus glycoproteins." *Adv. Virus Res.* 31:103-168.

Heinz, F.X. et al. (1983) "A topological and functional model of epitopes on the structural glycoprotein of tick-borne encephalitis virus defined by monoclonal antibodies." *Virology* 126:525-537.

Heinz, F.X. et al. (1994) "Structural changes and functional control of the tick-borne encephalitis virus glycoprotein E by the heterodimeric association with protein prM." *Virology* 198:109-117.

Henchal, E.A. et al. (1982) "Dengue virus-specific and flavivirus group determinants identified with monoclonal antibodies by indirect immunofluorescence" *Am. J. Trop. Med. Hyg.* 31:830-836.

Henchal, E.A. et al. (1985) "Epitopic analysis of antigenic determinants on the surface of dengue 2 virion using monoclonal antibodies" *Am. J. Trop. Med. Hyg.* 34:162-169.

Henchal, E.A. et al. (1986) "Identification of an antigenic and genetic variant of dengue-4 virus from the Caribbean." *Am. J. Trop. Med. Hyg.* 35:393-400.

Henchal, E.A. et al. (1988) "Synergistic interactions of anti-NS1 monoclonal antibodies protect passively immunized mice from lethal challenge with dengue 2 virus" *J. Gen. Virol.* 69:2101-2107.

Holzmann, H. et al. (1995) "Tick-borne encephalitis virus envelope protein E-specific monoclonal antibodies for the study of low pH-induced conformational changes and immature virions." *Arch. Virol.* 140:213-221.

Huber, C. et al. (1993) "The Vκ genes of the L regions and the repertoire of Vκ gene sequences in the human germ line." *Eur. J. Immunol.* 23:2868-2875.

International Preliminary Report on Patentability from PCT/US2004/040674, Jun. 12, 2006.

Johnson, S. et al. (1997) "Development of a humanized monoclonal antibody (MEDI-493) with potent in vitro and in vivo activity against respiratory syncytial virus." *J. Infect. Dis.* 176:1215-1224.

Kaufman, B.M. et al. (1987) "Monoclonal antibodies against dengue 2 virus E-glycoprotein protect mice against lethal dengue infection." *Am. J. Trop. Med. Hyg.* 36:427-434.

Kimura-Kuroda, J. et al. (1988) "Protection of mice against Japanese encephalitis virus by passive administration with monoclonal antibodies." *J. Immunol.* 141:3606-3610.

Lai, C.J. et al. (1991) "Infectious RNA transcribed from stably cloned full-length cDNA of dengue type 4 virus." *PNAS USA* 88:5139-5143.

Lanciotti, R.S. et al. (1997) "Molecular evolution and phylogeny of dengue type 4 virus." *J. Gen. Virol.* 78:2279-2286.

Lin, C.-W. et al. (2003) "A functional epitope determinant on domain III of the Japanese encephalitis virus envelope protein interacted with neutralizing-antibody combining sites." *J. Virol.* 77:2600-2606.

Mandl, C.W. et al. (1989) "Antigenic structure of the flavivirus envelope protein E at the molecular level, using tick-borne encephalitis virus as a model." *J. Virol.* 63:564-571.

Markoff, L. (1989) "In vitro processing of dengue virus structural proteins: cleavage of the pre-membrane protein." *J. Virol.* 63:3345-3352.

Maruyama, T. et al. (1999) "Ebola virus can be effectively neutralized by antibody produced in natural human infection." *J. Virol.* 73:6024-6030.

Mathews, J.H. et al. (1984) "Elucidation of the topography and determination of the protective epitopes on the E glycoprotein of Saint Louis encephalitis virus by passive transfer with monoclonal antibodies." *J. Immunol.* 132:1533-1537.

Men, R. et al. (1991) "Carboxy-terminally truncated dengue virus envelope glycoproteins expressed on the cell surface and secreted extracellularly exhibit increased immunogenicity in mice." *J. Virol.* 65:1400-1407.

Men, R. et al. (1996) "Dengue type 4 virus mutants containing deletions in the 3' noncoding region of the RNA genome: analysis of growth restriction in cell culture and altered viremia pattern and immunogenicity in rhesus monkeys." *J. Virol.* 70:3930-3937.

Men, R. et al. (2004) "Identification of chimpanzee fab fragments by repertoire cloning and production of a full-length humanized immunoglobulin g1 antibody that is highly efficient for neutralization of dengue type 4 virus." *J. Virol.* 78:4665-4674.

Modis, Y. et al. (2003) "A ligand-binding pocket in the dengue virus envelope glycoprotein." *PNAS USA* 100:6986-6991.

Ogata, N. et al. (1993) "Markedly prolonged incubation period of hepatitis B in a chimpanzee passively immunized with a human monoclonal antibody to the α determinant of hepatitis B surface antigen." *PNAS USA* 90:3014-3018.

Okuno, Y. et al. (1985) "Rapid focus reduction neutralization test of Japanese encephalitis virus in microtiter system." *Arch. Virol.* 86:129-135.

Pech, M. et al. (1985) "A large section of the gene locus encoding human immunoglobulin variable regions of the kappa type is duplicated." *J. Mol. Biol.* 183:291-299.

Persson, M.A. et al. (1991) "Generation of diverse high-affinity human monoclonal antibodies by repertoire cloning." *PNAS USA* 88:2432-2436.

Raffai, R. et al. (2000) "Binding of an antibody mimetic of the human low density lipoprotein receptor to apolipoprotein E is governed through electrostatic forces." *J. Biol. Chem.* 275:7109-7116.

Rey, P.A. et al. (1995) "The envelope glycoprotein from tick-borne encephalitis virus at 2 Å resolution." *Nature* 375:291-298.

Roehrig, J.T. et al. (1998) "Monoclonal antibody mapping of envelope glycoprotein of the dengue 2 virus, Jamaica." *Virology* 246:317-328.

Rosen, L. (1986) "Dengue in Greece in 1927 and 1928 and the pathogenesis of dengue hemorrhagic fever: new data and different conclusion." *Am. J. Trop. Med. Hyg.* 35:642-653.

Sanna, P.P. et al. (1999) "pFab-CMV, a single vector system for the rapid conversion of recombinant fabs into whole IgG1 antibodies." *Immunotechnology* 4:185-188.

Schlesinger, J.J. et al. (1999) "Influence of the human high-affinity IgG receptor FcγRI (CD64) on residual infectivity of neutralized dengue virus." *Virology* 260:84-88.

Schofield, D.J. et al. (2000) "Identification by phage display and characterization of two neutralizing chimpanzee monoclonal antibodies to the hepatitis E virus capsid protein." *J. Virol.* 74:5548-5555.

Shields, R L. et al. (2001) "High resolution mapping of the binding site on human IgG1 for FcγRI, FcγRII, FcγRIII, and FcRn and design of IgG1 variants with improved binding to the FcγR." *J. Biol. Chem.* 276:6591-6604.

Stadler, K. et al. (1997) "Proteolytic activation of tick-borne encephalitis virus by furin." *J. Virol.* 71:8475-8481.

Takahashi, N. et al. (1982) "Structure of human immunoglobulin gamma genes: implications for evolution of a gene family." *Cell* 29:671-679.

Tomlinson, I.M. et al. (1992) "The repertoire of human germline $V_H$ sequences reveals about fifty groups of $V_H$ segments with different hypervariable loops." *J. Mol. Biol.* 227:776-798.

Wang, W.-K. et al. (2002) "Dengue type 3 virus in plasma is a population of closely related genomes: quasispecies." *J. Virol.* 76:4662-4665.

Wengler, G. et al. (1989) "Cell-associated west nile flavivirus is covered with E + pre-M protein heterodimers which are destroyed and reorganized by proteolytic cleavage during virus release." *J. Virol.* 63:2521-2526.

Williamson, R.A. et al. (1993) "Human monoclonal antibodies against a plethora of viral pathogens from single combinatorial libraries." *PNAS USA* 90:4141-4145.

Wood, C.R. et al. (1990) "High level synthesis of immunoglobulins in Chinese hamster ovary cells." *J. Immunol.* 145:3011-3016.

Wu, T.T. et al. (1993) "Length distribution of CDRH3 in antibodies." *Proteins Struct. Funct. Genet.* 16:1-7.

\* cited by examiner (A)

| | FR1 | CDR1 | FR2 | CDR2 |
|---|---|---|---|---|
| 5A7 | ---ELTQGPATLSLSPGERATLSC | RAGQSLDS----SLLS | WYQQKPGQAPRLLMY | DASTRAP |
| 3C1 | ELQM,,S,S,,,A,V,D,V,VT, | ,,SED,N-----KW,A | ,,,,,,,,K,,K,,I, | K,,SLES |
| 3E4 | --,,,,S,LS,PVTL,QP,SI,, | ,SS,N,VHSDGNTY,, | ,I,,R,,,P,,,,I,, | KV,N,DS |
| 7G4 | --,,,,S,S,,,A,V,D,V,IT, | ,,S,GIS-----,W,A | ,,,,,,,,K,,KF,I, | K,,SLES |
| 5H2 | ELQM,,S,SS,,A,V,D,V,IT, | ,,S,DIS------IR,N | ,,,,,,,,K,,K,,I, | ,,,,LES |
| 5D9 | --,,,,SS,,A,V,D,V,IT,, | ,,S,GIS------NR,N | ,,,,,,,,G,KF,,, | ,,,SLVS |

| | FR3 | CDR3 | FR4 |
|---|---|---|---|
| 5A7 | GVPARFSGSGSGTDFTLTISSLQPEDFAVYY | CQQHYNLPRT | FGGGTKLEIKRT |
| 3C1 | ,,,S,,,,,,,,,,E,,,,,,,,,D,,,T,, | ,,,YQSY,Y, | ,,P,,,,,,,,,, |
| 3E4 | ,,,D,,,,,,A,,,,,,K,TRVEA,,VGL,, | ,V,GVQF,I, | ,,P,,,,,,,,,, |
| 7G4 | ,,,S,,,,,,,,,,E,,,,,,,,,D,,,T,, | ,,,YGSY,L, | ,,P,,,VD,,,,, |
| 5H2 | ,,,S,,,,,,,,,,,,,,,,,,,,,T,,,,, | ,,,FNSY,L, | ,,G,,,V,,,,,, |
| 5D9 | ,,,S,,,,,,,,,,,,,,,,,,,,,,,,,,, | ,,,FNSY,L, | ,,G,,,,,,,,,, |

(B)

| | FR1 | CDR1 | FR2 | CDR2 |
|---|---|---|---|---|
| 5A7 | EVQLLES-GGGLVQPGGSLRLSCAASGVTFS | SYWMH | WVRQAPGKGLEWV | SRINSDGSSTNYADSVEG |
| 3C1 | ,,,,,,,,,,,AEVKK,,,,VKV,,G,L,, | ,,GIS | ,,,,,,,,Q,P,,M | GV,IPIRGTA,,,QKFQ, |
| 3E4 | ,,,,,,,,QS,AEVKK,,,,VKV,,G,,,, | RNPIS | ,,,,,,,,Q,,,,M | ,V,VPIVGT,KH,QKFQ, |
| 7G4 | ,,,,,,,,,,,,,,,,,,,,T,,,,,,F,, | ,,,,, | ,,,,,,,,P,,,, | AL,KK,,,EKY,,E,,K, |
| 5H2 | ,,,,,,,,,,,,P,,,,K,SET,S,,T,TV,,GSI, | DFYWS | ,L,S,,,,,,,,,I | GYAH,RV,-AY,NP,LKS |
| 5D9 | ,,,,,,,,,,,,P,,,,K,SET,S,,T,TV,,GSI, | DFYWS | ,L,S,,,,,,,,,I | GVAH,RV,-AY,NP,LKS |

| | FR3 | CDR3 | FR4 |
|---|---|---|---|
| 5A7 | RFTISRDNAKNTLYLQMNSLRAEDTAVYYC | SRGGLWDWSPRRIEETKTPFDY | WGQGTLVTVSS |
| 3C1 | ,V,YTA,ESTS,V,MELS,,,S,,,,,,,, | AT------G,,CRYPTGS,,, | ,,,,,A,,,,,,, |
| 3E4 | ,V,,TA,ESTS,A,MELS,,,S,,,,,,,, | AT------Y,,YADVSSYSE, | ,,,,,,,,,,,,, |
| 7G4 | ,,,,,,,,,,,,,,,,,,S,,,,,,,,,,, | T,------ RITTLTVISDA,,I | ,,,,,,M,,,,,, |
| 5H2 | ,V,,,V,TS,,Q,S,RLSAVT,A,,,L,,, | A,------QGTGTTGVSED,F,L | ,,,,,K,I,,L |
| 5D9 | ,V,,,V,TS,,Q,S,RLSAVT,A,A,L,,, | A,------QGTGTTGVSED,F,L | ,,,,,K,I,,L, |

```
              FR1                          CDR1              FR2               CDR2
2H7    ELQMTQSPSSLSASVGDRVTITC RASQSITN----YLS WYQQKPGKAPKLLIS YSSTLQS
2H5    --EL.....V...........  .........T.. ... ............. .Y.FA...H.
3A2    --EL.....V.....T..A..  ............V.. ............N.. .Y.HA.....
1A5    .........V.....T..A..  ............... ............... .Y.HA.....
1B2    .....................  .....G.SS----E.N ............... .Y.DA.S.E.
1A10   ......L..VAP.QPAS.S..  KS...LLHSDGNT..F .L..S.QS.Q...Y GLSNRA.
3E4    ..A.L..L.PVTL.QPAS.S..  RS..NLVHSDGNT..S .IQ.RP.QP.R...Y KVSNRD.

FR3                          CDR3           FR4
2H7    GVPSRFSGSGSGTDFTLTISSLQPEDFATYY CHYG-YGTHT FGPGTKVDIKRT
2H5    ............N....D............. .Q.-...Q.. .Q...LEV...
3A2    .....I..........D............. ..........  .Q...LE....
1A5    .....I.......................... ..........  .Q...LE....
1B2    ................................ .QHFNSFPW.  .Q...LE....
1A10   ........D.....K..QVEA..VGVF.... .MQ.TQLPY.  .Q...LE....
3E4    ........D..A...K.TRVEA..VGLY.... .VQ.VQFPI.  .Q..RLE....
```

(B)

```
              FR1                   CDR1              FR2                CDR2
2H7    EVQLLE-SGGGLVQPGGSRRLSCAASGFTIS-- DNVMH WVRQAPGKGLEWV ALIYSAD-STHYADSVKG
2H5    ................................ ..... ............ ........-T........
3A2    .........Q..................... . ..... ............ ........-T........
1A5    ............................... . ..... ............ ........-T........
1B2    ------P..K.SQTLS.T..V..GSITSD HYFWS .M......R.... I GY.SYRG-T.Y.NP.L.S
1A10   ------E..AEVKK..SSVKV..KV..GTF.-- R.PIS ..........Q. ....M GV.VPIVGT.KH.QKFQ.
3E4    ......Q..AEVKK..SSVKV..KV..GTF.-- R.PIS ..........Q. ....M GV.VPIVGT.KH.QKFQ.

FR3                          CDR3               FR4
2H7    RFTISRDNSKNTLYLQMDGLRPEDTAVYYC AREYCTGGT-CFAHFDY WGQGTLVTVSS
2H5    ............................S .........-....... .S.........
3A2    ............................S .D.-...... .S.........
1A5    ............................S .G.-...... .T.........
1B2    ............................S .D.-...... .S.........
1A10   .V.M.VTAA................... .ASV.AGMPAAGTL.H ...........
1A10   RV.IIA..ESTSTAYMELSS...S...... TYYAD-----SSYSEY ...........
3E4    RV.IIA..ESTSTAYMELSS...S...... TYYADV----SSYSEY ...........
```

Fig. 10

A
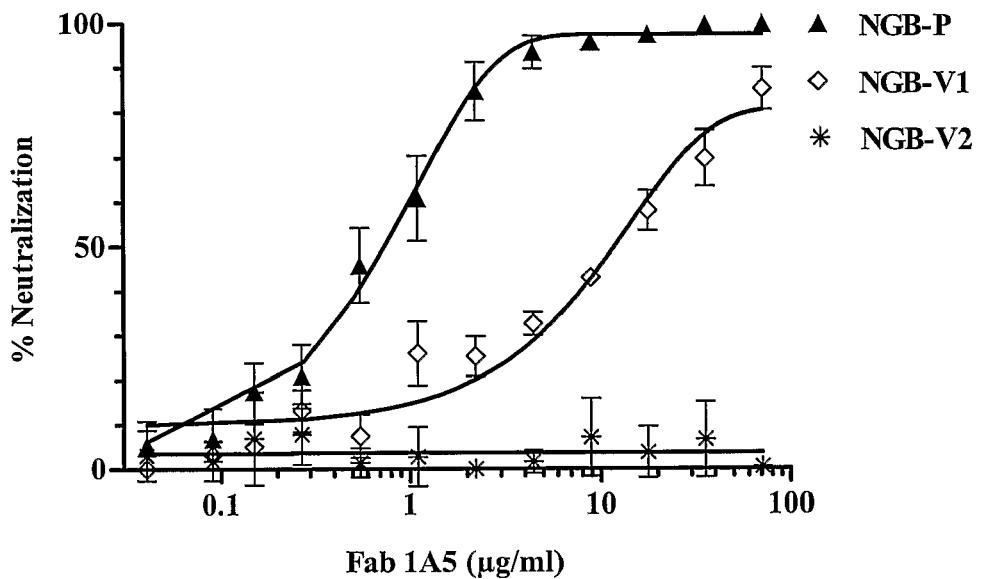
B
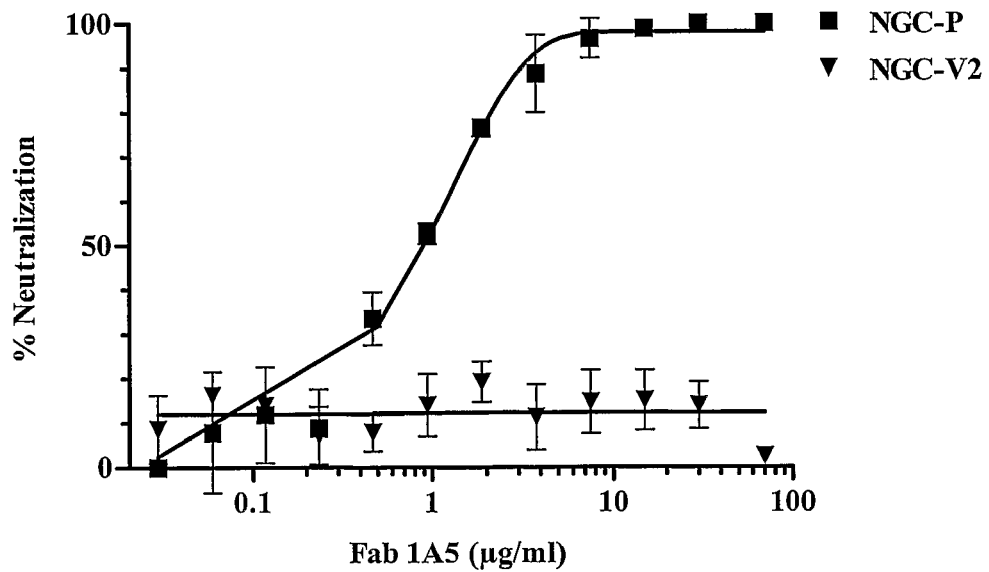
Fig. 11

A

```
                                          Gly106
                             c              ↓           d
DENV-2 P       89 RFVCKHSMVDRGWGNGCGLFGKGGIVTCAMFT 120
DENV-2 V1         --------------------------------
DENV-2 V2         ----------------V---------------
DENV-1            N---RRTF---------------SLI---K-K
DENV-3            NY----TY---------------SL----K-Q
DENV-4            QYI-RRDV---------------V----K-S
WNV               A---RQGV---------------S-D---K-A
JEV               SY---QGFT--------------S-D---K-S
JEV SA14-14-2     SY---QGFT-------F------S-D---K-S
SLEV              T----RDV---------------S-D---K--
YFV Asibi         DNA--RTYS--------------S--A--K--
YFV 17D           DNA--RTYS--------------S--A--K--
LGTV              GT---RDQS------H-------S----VK--
TBEV              GT---RDQS------H-------S--A-VKAA
```

B

```
                                    His317
                              A       ↓        B
DENV-2 P    306 FKVVKEIAETQHGTIVIRVQY 326
DENV-2 V1       -----------Q---------
DENV-2 V2       ---------------------
DENV-1          --LE--V-------VLVQ-K-
DENV-3          -VLK--VS------L-K-E-
DENV-4          -SID--M-------T-VK-K-
WNV             --FLGTP-D-G---V-LEL--
JEV             -SFA-NP-D-G---V--ELT-
JEV SA14-14-2   -SFA-NP-D-G---V--ELT-
SLEV            -TFS-NPTD-G---VIVEL--
YFV Asibi       MFF--NPDT-G---V-MQ-KV
YFV 17D         MFF--NPDT-G---V-MQ-KV
LGTV            -TWKRAPTDSG-D-V-ME-GF
TBEV            -TWRRAPTDSG-D-V-ME-TF
```

Fig. 12

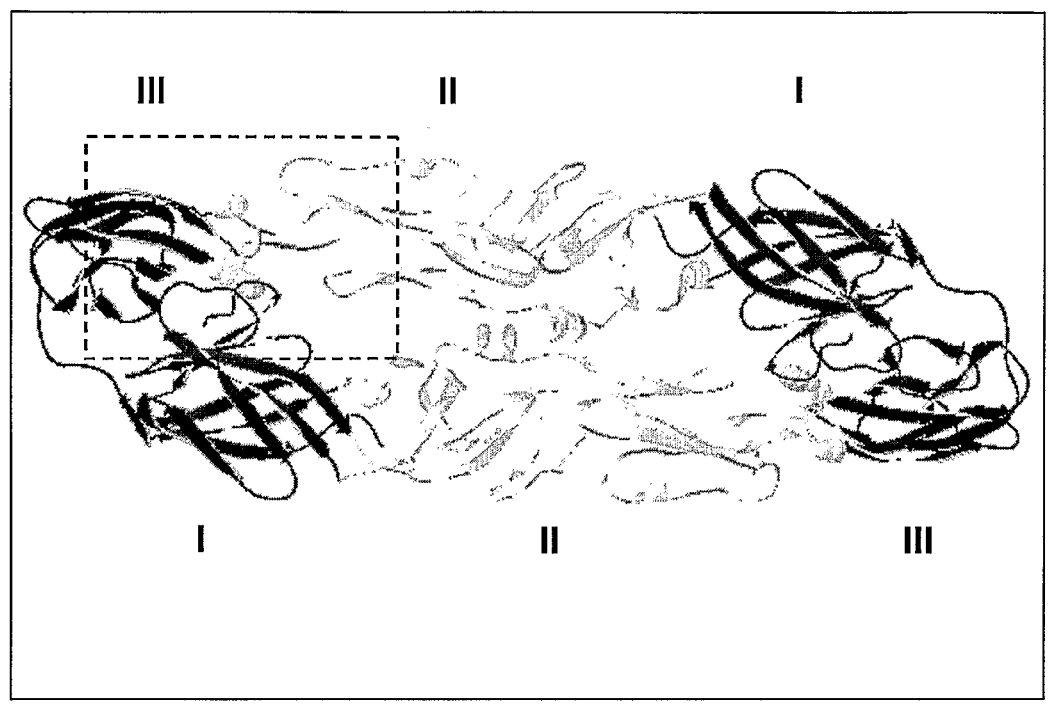
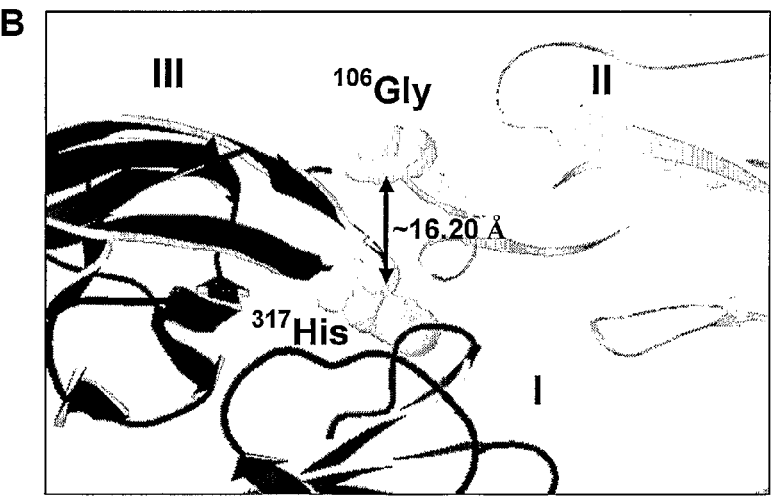
Fig. 13

A
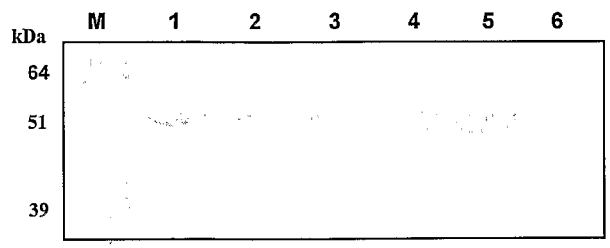
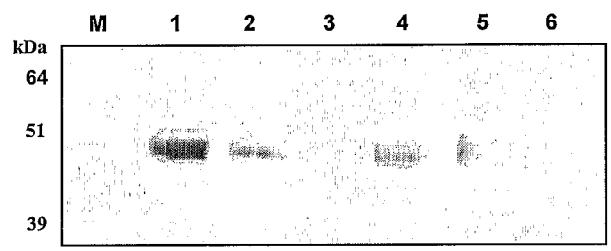
B
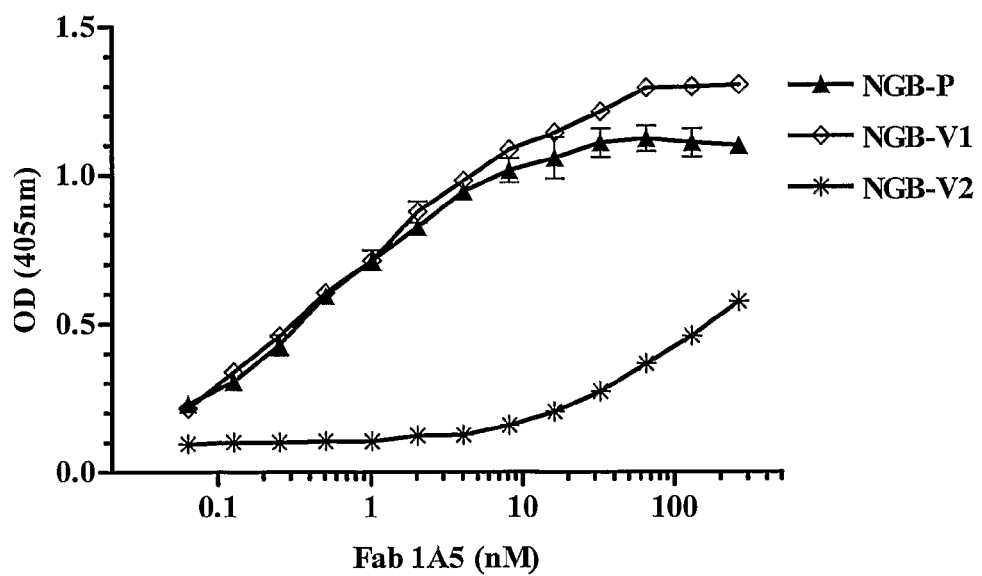
Fig. 14

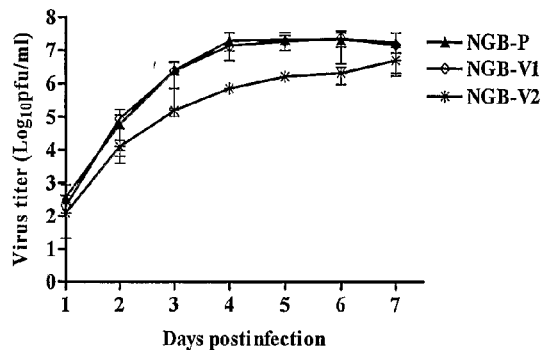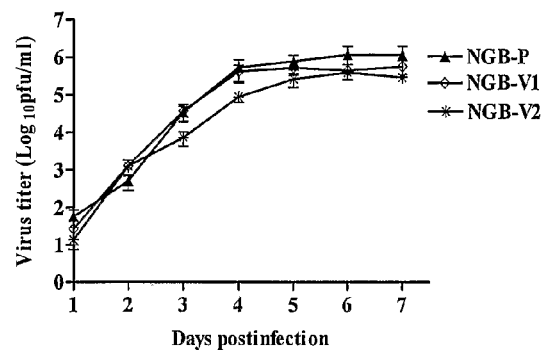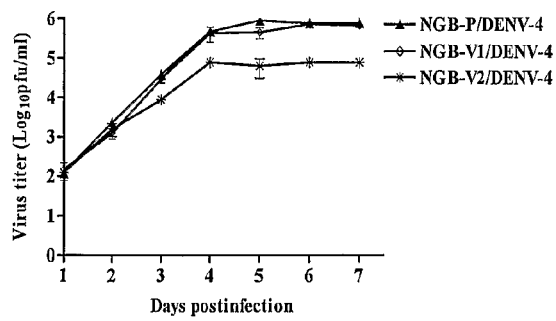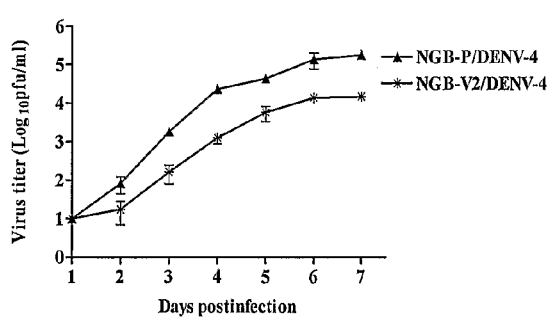
Fig. 16

A

<chart>
X-axis: Fab 1A5 (μg/ml), log scale 0.001 to 10
Y-axis: OD (405nm), 0.0 to 2.4
■ DENV-4 parent
▲ DENV-4 Gly$_{106}$Val
▼ DENV-4 Leu$_{107}$Phe
</chart>

B

<chart>
X-axis: Fab 1A5 (μg/ml), log scale 0.1 to 100
Y-axis: % Neutralization, 0 to 100
■ DENV-4 parent
▲ DENV-4 Gly$_{106}$Val
▼ DENV-4 Leu$_{107}$Phe
</chart>

Fig. 18

SEQUENCE LISTING

<160> NUMBER OF SEQ ID NOS: 228

<210> SEQ ID NO 1
<211> LENGTH: 123
<212> TYPE: PRT
<213> ORGANISM: Pan troglodytes

<400> SEQUENCE: 1

Glu Val Gln Leu Leu Glu Ser Gly Pro Gly Leu Val Lys Pro Ser Glu
 1               5                  10                  15

Thr Leu Ser Leu Thr Cys Thr Val Ser Gly Gly Ser Ile Ser Asp Phe
            20                  25                  30

Tyr Trp Ser Trp Leu Arg Gln Ser Pro Gly Lys Gly Leu Glu Trp Ile
        35                  40                  45

Gly Tyr Ala His Ser Arg Val Ser Ala Tyr Tyr Asn Pro Ser Leu Lys
    50                  55                  60

Ser Arg Val Thr Ile Ser Val Asp Thr Ser Lys Asn Gln Leu Ser Leu
65                  70                  75                  80

Arg Leu Ser Ala Val Thr Ala Ala Asp Thr Ala Leu Tyr Tyr Cys Ala
                85                  90                  95

Arg Gln Gly Thr Gly Thr Thr Gly Val Ser Glu Asp Pro Phe Asp Leu
            100                 105                 110

Trp Gly Gln Gly Thr Lys Val Ile Val Ser Leu
        115                 120

<210> SEQ ID NO 2
<211> LENGTH: 30
<212> TYPE: PRT
<213> ORGANISM: Pan troglodytes

<400> SEQUENCE: 2

Glu Val Gln Leu Leu Glu Ser Gly Pro Gly Leu Val Lys Pro Ser Glu
 1               5                  10                  15

Thr Leu Ser Leu Thr Cys Thr Val Ser Gly Gly Ser Ile Ser
            20                  25                  30

<210> SEQ ID NO 3
<211> LENGTH: 5
<212> TYPE: PRT
<213> ORGANISM: Pan troglodytes

<400> SEQUENCE: 3

Asp Phe Tyr Trp Ser
 1               5

<210> SEQ ID NO 4
<211> LENGTH: 13
<212> TYPE: PRT
<213> ORGANISM: Pan troglodytes

<400> SEQUENCE: 4

Trp Leu Arg Gln Ser Pro Gly Lys Gly Leu Glu Trp Ile
 1               5                  10

<210> SEQ ID NO 5
<211> LENGTH: 17
<212> TYPE: PRT
<213> ORGANISM: Pan troglodytes

<400> SEQUENCE: 5

```
Gly Tyr Ala His Ser Arg Val Ser Ala Tyr Tyr Asn Pro Ser Leu Lys
 1               5                  10                  15

Ser

<210> SEQ ID NO 6
<211> LENGTH: 30
<212> TYPE: PRT
<213> ORGANISM: Pan troglodytes

<400> SEQUENCE: 6

Arg Val Thr Ile Ser Val Asp Thr Ser Lys Asn Gln Leu Ser Leu Arg
 1               5                  10                  15

Leu Ser Ala Val Thr Ala Ala Asp Thr Ala Leu Tyr Tyr Cys
            20                  25                  30

<210> SEQ ID NO 7
<211> LENGTH: 17
<212> TYPE: PRT
<213> ORGANISM: Pan troglodytes

<400> SEQUENCE: 7

Ala Arg Gln Gly Thr Gly Thr Thr Gly Val Ser Glu Asp Pro Phe Asp
 1               5                  10                  15

Leu

<210> SEQ ID NO 8
<211> LENGTH: 11
<212> TYPE: PRT
<213> ORGANISM: Pan troglodytes

<400> SEQUENCE: 8

Trp Gly Gln Gly Thr Lys Val Ile Val Ser Leu
 1               5                  10

<210> SEQ ID NO 9
<211> LENGTH: 109
<212> TYPE: PRT
<213> ORGANISM: Pan troglodytes

<400> SEQUENCE: 9

Glu Leu Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Ile Arg
            20                  25                  30

Leu Asn Trp Tyr Gln Gln Lys Pro Gly Lys Ala Pro Lys Leu Leu Ile
        35                  40                  45

Tyr Asp Ala Ser Thr Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Phe Asn Ser Tyr Pro Leu
                85                  90                  95

Thr Phe Gly Gly Gly Thr Lys Val Glu Ile Lys Arg Thr
            100                 105

<210> SEQ ID NO 10
<211> LENGTH: 23
<212> TYPE: PRT
<213> ORGANISM: Pan troglodytes
```

```
<400> SEQUENCE: 10

Glu Leu Gln Met Thr Gln Ser Pro Ser Ser Leu Ser Ala Ser Val Gly
 1               5                  10                  15

Asp Arg Val Thr Ile Thr Cys
            20

<210> SEQ ID NO 11
<211> LENGTH: 11
<212> TYPE: PRT
<213> ORGANISM: Pan troglodytes

<400> SEQUENCE: 11

Arg Ala Ser Gln Asp Ile Ser Ile Arg Leu Asn
 1               5                  10

<210> SEQ ID NO 12
<211> LENGTH: 15
<212> TYPE: PRT
<213> ORGANISM: Pan troglodytes

<400> SEQUENCE: 12

Trp Tyr Gln Gln Lys Pro Gly Lys Ala Pro Lys Leu Leu Ile Tyr
 1               5                  10                  15

<210> SEQ ID NO 13
<211> LENGTH: 7
<212> TYPE: PRT
<213> ORGANISM: Pan troglodytes

<400> SEQUENCE: 13

Asp Ala Ser Thr Leu Glu Ser
 1               5

<210> SEQ ID NO 14
<211> LENGTH: 31
<212> TYPE: PRT
<213> ORGANISM: Pan troglodytes

<400> SEQUENCE: 14

Gly Val Pro Ser Arg Phe Ser Gly Ser Gly Ser Gly Thr Asp Phe Thr
 1               5                  10                  15

Leu Thr Ile Ser Ser Leu Gln Pro Glu Asp Phe Ala Thr Tyr Tyr
            20                  25                  30

<210> SEQ ID NO 15
<211> LENGTH: 10
<212> TYPE: PRT
<213> ORGANISM: Pan troglodytes

<400> SEQUENCE: 15

Cys Gln Gln Phe Asn Ser Tyr Pro Leu Thr
 1               5                  10

<210> SEQ ID NO 16
<211> LENGTH: 12
<212> TYPE: PRT
<213> ORGANISM: Pan troglodytes

<400> SEQUENCE: 16

Phe Gly Gly Gly Thr Lys Val Glu Ile Lys Arg Thr
 1               5                  10

<210> SEQ ID NO 17
```

```
<211> LENGTH: 129
<212> TYPE: PRT
<213> ORGANISM: Pan troglodytes

<400> SEQUENCE: 17

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Val Thr Phe Ser Ser Tyr
            20                  25                  30

Trp Met His Trp Val Arg Gln Ala Pro Gly Lys Gly Leu Glu Trp Val
        35                  40                  45

Ser Arg Ile Asn Ser Asp Gly Ser Ser Thr Asn Tyr Ala Asp Ser Val
    50                  55                  60

Glu Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ser Arg Gly Gly Leu Trp Asp Trp Ser Pro Arg Arg Ile Glu Glu Thr
            100                 105                 110

Lys Thr Pro Phe Asp Tyr Trp Gly Gln Gly Thr Leu Val Thr Val Ser
        115                 120                 125

Ser

<210> SEQ ID NO 18
<211> LENGTH: 30
<212> TYPE: PRT
<213> ORGANISM: Pan troglodytes

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Val Thr Phe Ser
            20                  25                  30

<210> SEQ ID NO 19
<211> LENGTH: 5
<212> TYPE: PRT
<213> ORGANISM: Pan troglodytes

<400> SEQUENCE: 19

Ser Tyr Trp Met His
 1               5

<210> SEQ ID NO 20
<211> LENGTH: 13
<212> TYPE: PRT
<213> ORGANISM: Pan troglodytes

<400> SEQUENCE: 20

Trp Val Arg Gln Ala Pro Gly Lys Gly Leu Glu Trp Val
 1               5                  10

<210> SEQ ID NO 21
<211> LENGTH: 18
<212> TYPE: PRT
<213> ORGANISM: Pan troglodytes

<400> SEQUENCE: 21

Ser Arg Ile Asn Ser Asp Gly Ser Ser Thr Asn Tyr Ala Asp Ser Val
 1               5                  10                  15
```

Glu Gly

```
<210> SEQ ID NO 22
<211> LENGTH: 30
<212> TYPE: PRT
<213> ORGANISM: Pan troglodytes

<400> SEQUENCE: 22

Arg Phe Thr Ile Ser Arg Asp Asn Ala Lys Asn Thr Leu Tyr Leu Gln
1               5                   10                  15

Met Asn Ser Leu Arg Ala Glu Asp Thr Ala Val Tyr Tyr Cys
            20                  25                  30

<210> SEQ ID NO 23
<211> LENGTH: 22
<212> TYPE: PRT
<213> ORGANISM: Pan troglodytes

<400> SEQUENCE: 23

Ser Arg Gly Gly Leu Trp Asp Trp Ser Pro Arg Arg Ile Glu Glu Thr
1               5                   10                  15

Lys Thr Pro Phe Asp Tyr
            20

<210> SEQ ID NO 24
<211> LENGTH: 11
<212> TYPE: PRT
<213> ORGANISM: Pan troglodytes

<400> SEQUENCE: 24

Trp Gly Gln Gly Thr Leu Val Thr Val Ser Ser
1               5                   10

<210> SEQ ID NO 25
<211> LENGTH: 108
<212> TYPE: PRT
<213> ORGANISM: Pan troglodytes

<400> SEQUENCE: 25

Glu Leu Thr Gln Gly Pro Ala Thr Leu Ser Leu Ser Pro Gly Glu Arg
1               5                   10                  15

Ala Thr Leu Ser Cys Arg Ala Gly Gln Ser Leu Asp Ser Ser Leu Leu
            20                  25                  30

Ser Trp Tyr Gln Gln Lys Pro Gly Gln Ala Pro Arg Leu Leu Met Tyr
        35                  40                  45

Asp Ala Ser Thr Arg Ala Pro Gly Val Pro Ala Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Val Tyr Tyr Cys Gln Gln His Tyr Asn Leu Pro Arg Thr
                85                  90                  95

Phe Gly Gln Gly Thr Lys Leu Glu Ile Lys Arg Thr
            100                 105

<210> SEQ ID NO 26
<211> LENGTH: 21
<212> TYPE: PRT
<213> ORGANISM: Pan troglodytes

<400> SEQUENCE: 26

Glu Leu Thr Gln Gly Pro Ala Thr Leu Ser Leu Ser Pro Gly Glu Arg
```

```
                1               5                  10                  15

Ala Thr Leu Ser Cys
            20

<210> SEQ ID NO 27
<211> LENGTH: 12
<212> TYPE: PRT
<213> ORGANISM: Pan troglodytes

<400> SEQUENCE: 27

Arg Ala Gly Gln Ser Leu Asp Ser Ser Leu Leu Ser
 1               5                  10

<210> SEQ ID NO 28
<211> LENGTH: 15
<212> TYPE: PRT
<213> ORGANISM: Pan troglodytes

<400> SEQUENCE: 28

Trp Tyr Gln Gln Lys Pro Gly Gln Ala Pro Arg Leu Leu Met Tyr
 1               5                  10                  15

<210> SEQ ID NO 29
<211> LENGTH: 7
<212> TYPE: PRT
<213> ORGANISM: Pan troglodytes

<400> SEQUENCE: 29

Asp Ala Ser Thr Arg Ala Pro
 1               5

<210> SEQ ID NO 30
<211> LENGTH: 31
<212> TYPE: PRT
<213> ORGANISM: Pan troglodytes

<400> SEQUENCE: 30

Gly Val Pro Ala Arg Phe Ser Gly Ser Gly Ser Gly Thr Asp Phe Thr
 1               5                  10                  15

Leu Thr Ile Ser Ser Leu Gln Pro Glu Asp Phe Ala Val Tyr Tyr
            20                  25                  30

<210> SEQ ID NO 31
<211> LENGTH: 10
<212> TYPE: PRT
<213> ORGANISM: Pan troglodytes

<400> SEQUENCE: 31

Cys Gln Gln His Tyr Asn Leu Pro Arg Thr
 1               5                  10

<210> SEQ ID NO 32
<211> LENGTH: 12
<212> TYPE: PRT
<213> ORGANISM: Pan troglodytes

<400> SEQUENCE: 32

Phe Gly Gln Gly Thr Lys Leu Glu Ile Lys Arg Thr
 1               5                  10

<210> SEQ ID NO 33
<211> LENGTH: 122
<212> TYPE: PRT
<213> ORGANISM: Pan troglodytes
```

<400> SEQUENCE: 33

Glu Val Gln Leu Leu Glu Ser Gly Ala Glu Val Lys Lys Pro Gly Gly
1               5                   10                  15

Ser Val Lys Val Ser Cys Lys Val Ser Gly Gly Thr Leu Ser Ser Tyr
            20                  25                  30

Gly Ile Ser Trp Val Arg Gln Ala Pro Gly Gln Gly Pro Glu Trp Met
        35                  40                  45

Gly Val Ile Ile Pro Ile Arg Gly Thr Ala Asn Tyr Ala Gln Lys Phe
    50                  55                  60

Gln Gly Arg Val Thr Tyr Thr Ala Asp Glu Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Gly Arg Arg Gly Arg Tyr Pro Thr Gly Ser Phe Asp Tyr Trp
            100                 105                 110

Gly Gln Gly Ala Leu Val Thr Val Ser Ser
        115                 120

<210> SEQ ID NO 34
<211> LENGTH: 30
<212> TYPE: PRT
<213> ORGANISM: Pan troglodytes

<400> SEQUENCE: 34

Glu Val Gln Leu Leu Glu Ser Gly Ala Glu Val Lys Lys Pro Gly Gly
1               5                   10                  15

Ser Val Lys Val Ser Cys Lys Val Ser Gly Gly Thr Leu Ser
            20                  25                  30

<210> SEQ ID NO 35
<211> LENGTH: 5
<212> TYPE: PRT
<213> ORGANISM: Pan troglodytes

<400> SEQUENCE: 35

Ser Tyr Gly Ile Ser
1               5

<210> SEQ ID NO 36
<211> LENGTH: 13
<212> TYPE: PRT
<213> ORGANISM: Pan troglodytes

<400> SEQUENCE: 36

Trp Val Arg Gln Ala Pro Gly Gln Gly Pro Glu Trp Met
1               5                   10

<210> SEQ ID NO 37
<211> LENGTH: 18
<212> TYPE: PRT
<213> ORGANISM: Pan troglodytes

<400> SEQUENCE: 37

Gly Val Ile Ile Pro Ile Arg Gly Thr Ala Asn Tyr Ala Gln Lys Phe
1               5                   10                  15

Gln Gly

<210> SEQ ID NO 38
<211> LENGTH: 30

```
<212> TYPE: PRT
<213> ORGANISM: Pan troglodytes

<400> SEQUENCE: 38

Arg Val Thr Tyr Thr Ala Asp Glu Ser Thr Ser Thr Val Tyr Met Glu
 1               5                  10                  15

Leu Ser Ser Leu Arg Ser Glu Asp Thr Ala Val Tyr Tyr Cys
            20                  25                  30

<210> SEQ ID NO 39
<211> LENGTH: 15
<212> TYPE: PRT
<213> ORGANISM: Pan troglodytes

<400> SEQUENCE: 39

Ala Thr Gly Arg Arg Gly Arg Tyr Pro Thr Gly Ser Phe Asp Tyr
 1               5                  10                  15

<210> SEQ ID NO 40
<211> LENGTH: 11
<212> TYPE: PRT
<213> ORGANISM: Pan troglodytes

<400> SEQUENCE: 40

Trp Gly Gln Gly Ala Leu Val Thr Val Ser Ser
 1               5                  10

<210> SEQ ID NO 41
<211> LENGTH: 109
<212> TYPE: PRT
<213> ORGANISM: Pan troglodytes

<400> SEQUENCE: 41

Glu Leu Gln Met Thr Gln Ser Pro Ser Thr Leu Ser Ala Ser Val Gly
 1               5                  10                  15

Asp Arg Val Thr Val Thr Cys Arg Ala Ser Glu Asp Leu Asn Lys Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ser Tyr Pro Tyr
                85                  90                  95

Thr Phe Gly Pro Gly Thr Lys Leu Glu Ile Lys Arg Thr
            100                 105

<210> SEQ ID NO 42
<211> LENGTH: 23
<212> TYPE: PRT
<213> ORGANISM: Pan troglodytes

<400> SEQUENCE: 42

Glu Leu Gln Met Thr Gln Ser Pro Ser Thr Leu Ser Ala Ser Val Gly
 1               5                  10                  15

Asp Arg Val Thr Val Thr Cys
            20

<210> SEQ ID NO 43
<211> LENGTH: 11
```

```
<212> TYPE: PRT
<213> ORGANISM: Pan troglodytes

<400> SEQUENCE: 43

Arg Ala Ser Glu Asp Leu Asn Lys Trp Leu Ala
1               5                   10

<210> SEQ ID NO 44
<211> LENGTH: 15
<212> TYPE: PRT
<213> ORGANISM: Pan troglodytes

<400> SEQUENCE: 44

Trp Tyr Gln Gln Lys Pro Gly Lys Ala Pro Lys Leu Leu Ile Tyr
1               5                   10                  15

<210> SEQ ID NO 45
<211> LENGTH: 7
<212> TYPE: PRT
<213> ORGANISM: Pan troglodytes

<400> SEQUENCE: 45

Lys Ala Ser Ser Leu Glu Ser
1               5

<210> SEQ ID NO 46
<211> LENGTH: 31
<212> TYPE: PRT
<213> ORGANISM: Pan troglodytes

<400> SEQUENCE: 46

Gly Val Pro Ser Arg Phe Ser Gly Ser Gly Ser Gly Thr Glu Phe Thr
1               5                   10                  15

Leu Thr Ile Ser Ser Leu Gln Pro Asp Asp Phe Ala Thr Tyr Tyr
            20                  25                  30

<210> SEQ ID NO 47
<211> LENGTH: 10
<212> TYPE: PRT
<213> ORGANISM: Pan troglodytes

<400> SEQUENCE: 47

Cys Gln Gln Tyr Gln Ser Tyr Pro Tyr Thr
1               5                   10

<210> SEQ ID NO 48
<211> LENGTH: 12
<212> TYPE: PRT
<213> ORGANISM: Pan troglodytes

<400> SEQUENCE: 48

Phe Gly Pro Gly Thr Lys Leu Glu Ile Lys Arg Thr
1               5                   10

<210> SEQ ID NO 49
<211> LENGTH: 123
<212> TYPE: PRT
<213> ORGANISM: Pan troglodytes

<400> SEQUENCE: 49

Glu Val Gln Leu Leu Glu Gln Ser Gly Ala Glu Val Lys Lys Pro Gly
1               5                   10                  15

Gly Ser Val Lys Val Ser Cys Lys Val Ser Gly Gly Thr Phe Ser Arg
            20                  25                  30
```

```
Asn Pro Ile Ser Trp Val Arg Gln Ala Pro Gly Gln Gly Leu Glu Trp
        35                  40                  45

Met Ser Val Ile Val Pro Ile Val Gly Thr Thr Lys His Ala Gln Lys
 50                  55                  60

Phe Gln Gly Arg Val Thr Ile Thr Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Thr Tyr Arg Arg Tyr Ala Asp Val Ser Ser Tyr Ser Glu Tyr
                100                 105                 110

Trp Gly Gln Gly Thr Leu Val Thr Val Ser Ser
        115                 120

<210> SEQ ID NO 50
<211> LENGTH: 31
<212> TYPE: PRT
<213> ORGANISM: Pan troglodytes

<400> SEQUENCE: 50

Glu Val Gln Leu Leu Glu Gln Ser Gly Ala Glu Val Lys Lys Pro Gly
1               5                   10                  15

Gly Ser Val Lys Val Ser Cys Lys Val Ser Gly Gly Thr Phe Ser
            20                  25                  30

<210> SEQ ID NO 51
<211> LENGTH: 5
<212> TYPE: PRT
<213> ORGANISM: Pan troglodytes

<400> SEQUENCE: 51

Arg Asn Pro Ile Ser
1               5

<210> SEQ ID NO 52
<211> LENGTH: 13
<212> TYPE: PRT
<213> ORGANISM: Pan troglodytes

<400> SEQUENCE: 52

Trp Val Arg Gln Ala Pro Gly Gln Gly Leu Glu Trp Met
1               5                   10

<210> SEQ ID NO 53
<211> LENGTH: 18
<212> TYPE: PRT
<213> ORGANISM: Pan troglodytes

<400> SEQUENCE: 53

Ser Val Ile Val Pro Ile Val Gly Thr Thr Lys His Ala Gln Lys Phe
1               5                   10                  15

Gln Gly

<210> SEQ ID NO 54
<211> LENGTH: 30
<212> TYPE: PRT
<213> ORGANISM: Pan troglodytes

<400> SEQUENCE: 54

Arg Val Thr Ile Thr Ala Asp Glu Ser Thr Ser Thr Ala Tyr Met Glu
1               5                   10                  15
```

-continued

```
Leu Ser Ser Leu Arg Ser Glu Asp Thr Ala Val Tyr Tyr Cys
          20                  25                  30
```

<210> SEQ ID NO 55
<211> LENGTH: 15
<212> TYPE: PRT
<213> ORGANISM: Pan troglodytes

<400> SEQUENCE: 55

```
Ala Thr Tyr Arg Arg Tyr Ala Asp Val Ser Tyr Ser Glu Tyr
 1               5                  10                  15
```

<210> SEQ ID NO 56
<211> LENGTH: 11
<212> TYPE: PRT
<213> ORGANISM: Pan troglodytes

<400> SEQUENCE: 56

```
Trp Gly Gln Gly Thr Leu Val Thr Val Ser Ser
 1               5                  10
```

<210> SEQ ID NO 57
<211> LENGTH: 112
<212> TYPE: PRT
<213> ORGANISM: Pan troglodytes

<400> SEQUENCE: 57

```
Glu Leu Thr Gln Ser Pro Leu Ser Leu Pro Val Thr Leu Gly Gln Pro
 1               5                  10                  15

Ala Ser Ile Ser Cys Arg Ser Ser Gln Asn Leu Val His Ser Asp Gly
             20                  25                  30

Asn Thr Tyr Leu Ser Trp Ile Gln Gln Arg Pro Gly Gln Pro Pro Arg
         35                  40                  45

Leu Leu Ile Tyr Lys Val Ser Asn Arg Asp Ser Gly Val Pro Asp Arg
     50                  55                  60

Phe Ser Gly Ser Gly Ala Gly Thr Asp Phe Thr Leu Lys Ile Thr Arg
65                  70                  75                  80

Val Glu Ala Glu Asp Val Gly Leu Tyr Tyr Cys Val Gln Gly Val Gln
                 85                  90                  95

Phe Pro Ile Thr Phe Gly Gln Gly Thr Lys Leu Glu Ile Lys Arg Thr
            100                 105                 110
```

<210> SEQ ID NO 58
<211> LENGTH: 21
<212> TYPE: PRT
<213> ORGANISM: Pan troglodytes

<400> SEQUENCE: 58

```
Glu Leu Thr Gln Ser Pro Leu Ser Leu Pro Val Thr Leu Gly Gln Pro
 1               5                  10                  15

Ala Ser Ile Ser Cys
             20
```

<210> SEQ ID NO 59
<211> LENGTH: 16
<212> TYPE: PRT
<213> ORGANISM: Pan troglodytes

<400> SEQUENCE: 59

```
Arg Ser Ser Gln Asn Leu Val His Ser Asp Gly Asn Thr Tyr Leu Ser
 1               5                  10                  15
```

```
<210> SEQ ID NO 60
<211> LENGTH: 15
<212> TYPE: PRT
<213> ORGANISM: Pan troglodytes

<400> SEQUENCE: 60

Trp Ile Gln Gln Arg Pro Gly Gln Pro Pro Arg Leu Leu Ile Tyr
1               5                   10                  15

<210> SEQ ID NO 61
<211> LENGTH: 7
<212> TYPE: PRT
<213> ORGANISM: Pan troglodytes

<400> SEQUENCE: 61

Lys Val Ser Asn Arg Asp Ser
1               5

<210> SEQ ID NO 62
<211> LENGTH: 31
<212> TYPE: PRT
<213> ORGANISM: Pan troglodytes

<400> SEQUENCE: 62

Gly Val Pro Asp Arg Phe Ser Gly Ser Gly Ala Gly Thr Asp Phe Thr
1               5                   10                  15

Leu Lys Ile Thr Arg Val Glu Ala Glu Asp Val Gly Leu Tyr Tyr
            20                  25                  30

<210> SEQ ID NO 63
<211> LENGTH: 10
<212> TYPE: PRT
<213> ORGANISM: Pan troglodytes

<400> SEQUENCE: 63

Cys Val Gln Gly Val Gln Phe Pro Ile Thr
1               5                   10

<210> SEQ ID NO 64
<211> LENGTH: 12
<212> TYPE: PRT
<213> ORGANISM: Pan troglodytes

<400> SEQUENCE: 64

Phe Gly Gln Gly Thr Lys Leu Glu Ile Lys Arg Thr
1               5                   10

<210> SEQ ID NO 65
<211> LENGTH: 123
<212> TYPE: PRT
<213> ORGANISM: Pan troglodytes

<400> SEQUENCE: 65

Glu Val Gln Leu Leu Glu Ser Gly Gly Gly Leu Val Gln Pro Gly Gly
1               5                   10                  15

Ser Leu Thr Leu Ser Cys Ala Ala Ser Gly Phe Thr Phe Ser Ser Tyr
            20                  25                  30

Trp Met His Trp Val Arg Gln Ala Pro Gly Lys Gly Pro Glu Trp Val
        35                  40                  45

Ala Leu Ile Lys Lys Asp Gly Ser Glu Lys Tyr Tyr Ala Glu Ser Val
    50                  55                  60

Lys Gly Arg Phe Thr Ile Ser Arg Asp Asn Ala Lys Asn Ser Leu Tyr
```

```
                65                  70                  75                  80
Leu Gln Met Asn Ser Leu Arg Ala Glu Asp Thr Ala Val Tyr Tyr Cys
                    85                  90                  95

Thr Arg Arg Ile Thr Thr Leu Thr Val Ile Ser Asp Ala Phe Asp Ile
                    100                 105                 110

Trp Gly Gln Gly Thr Met Val Thr Val Ser Ser
            115                 120

<210> SEQ ID NO 66
<211> LENGTH: 30
<212> TYPE: PRT
<213> ORGANISM: Pan troglodytes

<400> SEQUENCE: 66

Glu Val Gln Leu Leu Glu Ser Gly Gly Gly Leu Val Gln Pro Gly Gly
1               5                   10                  15

Ser Leu Thr Leu Ser Cys Ala Ala Ser Gly Phe Thr Phe Ser
            20                  25                  30

<210> SEQ ID NO 67
<211> LENGTH: 5
<212> TYPE: PRT
<213> ORGANISM: Pan troglodytes

<400> SEQUENCE: 67

Ser Tyr Trp Met His
1               5

<210> SEQ ID NO 68
<211> LENGTH: 13
<212> TYPE: PRT
<213> ORGANISM: Pan troglodytes

<400> SEQUENCE: 68

Trp Val Arg Gln Ala Pro Gly Lys Gly Pro Glu Trp Val
1               5                   10

<210> SEQ ID NO 69
<211> LENGTH: 18
<212> TYPE: PRT
<213> ORGANISM: Pan troglodytes

<400> SEQUENCE: 69

Ala Leu Ile Lys Lys Asp Gly Ser Glu Lys Tyr Tyr Ala Glu Ser Val
1               5                   10                  15

Lys Gly

<210> SEQ ID NO 70
<211> LENGTH: 30
<212> TYPE: PRT
<213> ORGANISM: Pan troglodytes

<400> SEQUENCE: 70

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys
            20                  25                  30

<210> SEQ ID NO 71
<211> LENGTH: 16
<212> TYPE: PRT
<213> ORGANISM: Pan troglodytes
```

```
<400> SEQUENCE: 71

Thr Arg Arg Ile Thr Thr Leu Thr Val Ile Ser Asp Ala Phe Asp Ile
 1               5                  10                  15

<210> SEQ ID NO 72
<211> LENGTH: 11
<212> TYPE: PRT
<213> ORGANISM: Pan troglodytes

<400> SEQUENCE: 72

Trp Gly Gln Gly Thr Met Val Thr Val Ser Ser
 1               5                  10

<210> SEQ ID NO 73
<211> LENGTH: 107
<212> TYPE: PRT
<213> ORGANISM: Pan troglodytes

<400> SEQUENCE: 73

Glu Leu Thr Gln Ser Pro Ser Thr Leu Ser Ala Ser Val Gly Asp Arg
 1               5                  10                  15

Val Thr Ile Thr Cys Arg Ala Ser Gln Gly Ile Ser Ser Trp Leu Ala
            20                  25                  30

Trp Tyr Gln Gln Lys Pro Gly Lys Ala Pro Lys Phe Leu Ile Tyr Lys
        35                  40                  45

Ala Ser Ser Leu Glu Ser Gly Val Pro Ser Arg Phe Ser Gly Ser Gly
    50                  55                  60

Ser Gly Thr Glu Phe Thr Leu Thr Ile Ser Ser Leu Gln Pro Asp Asp
65                  70                  75                  80

Phe Ala Thr Tyr Tyr Cys Gln Gln Tyr Gly Ser Tyr Pro Leu Thr Phe
                85                  90                  95

Gly Pro Gly Thr Lys Val Asp Ile Lys Arg Thr
            100                 105

<210> SEQ ID NO 74
<211> LENGTH: 21
<212> TYPE: PRT
<213> ORGANISM: Pan troglodytes

<400> SEQUENCE: 74

Glu Leu Thr Gln Ser Pro Ser Thr Leu Ser Ala Ser Val Gly Asp Arg
 1               5                  10                  15

Val Thr Ile Thr Cys
            20

<210> SEQ ID NO 75
<211> LENGTH: 11
<212> TYPE: PRT
<213> ORGANISM: Pan troglodytes

<400> SEQUENCE: 75

Arg Ala Ser Gln Gly Ile Ser Ser Trp Leu Ala
 1               5                  10

<210> SEQ ID NO 76
<211> LENGTH: 15
<212> TYPE: PRT
<213> ORGANISM: Pan troglodytes

<400> SEQUENCE: 76
```

```
Trp Tyr Gln Gln Lys Pro Gly Lys Ala Pro Lys Phe Leu Ile Tyr
 1               5                  10                  15

<210> SEQ ID NO 77
<211> LENGTH: 7
<212> TYPE: PRT
<213> ORGANISM: Pan troglodytes

<400> SEQUENCE: 77

Lys Ala Ser Ser Leu Glu Ser
 1               5

<210> SEQ ID NO 78
<211> LENGTH: 31
<212> TYPE: PRT
<213> ORGANISM: Pan troglodytes

<400> SEQUENCE: 78

Gly Val Pro Ser Arg Phe Ser Gly Ser Gly Ser Gly Thr Glu Phe Thr
 1               5                  10                  15

Leu Thr Ile Ser Ser Leu Gln Pro Asp Asp Phe Ala Thr Tyr Tyr
                20                  25                  30

<210> SEQ ID NO 79
<211> LENGTH: 10
<212> TYPE: PRT
<213> ORGANISM: Pan troglodytes

<400> SEQUENCE: 79

Cys Gln Gln Tyr Gly Ser Tyr Pro Leu Thr
 1               5                  10

<210> SEQ ID NO 80
<211> LENGTH: 12
<212> TYPE: PRT
<213> ORGANISM: Pan troglodytes

<400> SEQUENCE: 80

Phe Gly Pro Gly Thr Lys Val Asp Ile Lys Arg Thr
 1               5                  10

<210> SEQ ID NO 81
<211> LENGTH: 123
<212> TYPE: PRT
<213> ORGANISM: Pan troglodytes

<400> SEQUENCE: 81

Glu Val Gln Leu Leu Glu Ser Gly Pro Gly Leu Val Lys Pro Ser Glu
 1               5                  10                  15
Thr Leu Ser Leu Thr Cys Thr Val Ser Gly Gly Ser Ile Ser Asp Phe
                20                  25                  30
Tyr Trp Ser Trp Leu Arg Gln Ser Pro Gly Lys Gly Leu Glu Trp Ile
            35                  40                  45
Gly Val Ala His Ser Arg Val Ser Ala Tyr Tyr Asn Pro Ser Leu Lys
        50                  55                  60
Ser Arg Val Thr Ile Ser Val Asp Thr Ser Lys Asn Gln Leu Ser Leu
 65                  70                  75                  80
Arg Leu Ser Ala Val Thr Ala Ala Asp Ala Ala Leu Tyr Tyr Cys Ala
                85                  90                  95
Arg Gln Gly Thr Gly Thr Thr Gly Val Ser Glu Asp Pro Phe Asp Leu
            100                 105                 110
Trp Gly Gln Gly Thr Lys Val Ile Val Ser Leu
        115                 120

<210> SEQ ID NO 82
<211> LENGTH: 30
<212> TYPE: PRT
```

<213> ORGANISM: Pan troglodytes

<400> SEQUENCE: 82

Glu Val Gln Leu Leu Glu Ser Gly Pro Gly Leu Val Lys Pro Ser Glu
1               5                   10                  15
Thr Leu Ser Leu Thr Cys Thr Val Ser Gly Gly Ser Ile Ser
            20                  25                  30

<210> SEQ ID NO 83
<211> LENGTH: 5
<212> TYPE: PRT
<213> ORGANISM: Pan troglodytes

<400> SEQUENCE: 83

Asp Phe Tyr Trp Ser
1               5

<210> SEQ ID NO 84
<211> LENGTH: 13
<212> TYPE: PRT
<213> ORGANISM: Pan troglodytes

<400> SEQUENCE: 84

Trp Leu Arg Gln Ser Pro Gly Lys Gly Leu Glu Trp Ile
1               5                   10

<210> SEQ ID NO 85
<211> LENGTH: 17
<212> TYPE: PRT
<213> ORGANISM: Pan troglodytes

<400> SEQUENCE: 85

Gly Val Ala His Ser Arg Val Ser Ala Tyr Tyr Asn Pro Ser Leu Lys
1               5                   10                  15
Ser

<210> SEQ ID NO 86
<211> LENGTH: 30
<212> TYPE: PRT
<213> ORGANISM: Pan troglodytes

<400> SEQUENCE: 86

Arg Val Thr Ile Ser Val Asp Thr Ser Lys Asn Gln Leu Ser Leu Arg
1               5                   10                  15
Leu Ser Ala Val Thr Ala Ala Asp Ala Ala Leu Tyr Tyr Cys
            20                  25                  30

<210> SEQ ID NO 87
<211> LENGTH: 17
<212> TYPE: PRT
<213> ORGANISM: Pan troglodytes

<400> SEQUENCE: 87

Ala Arg Gln Gly Thr Gly Thr Thr Gly Val Ser Glu Asp Pro Phe Asp
1               5                   10                  15
Leu

<210> SEQ ID NO 88
<211> LENGTH: 11
<212> TYPE: PRT
<213> ORGANISM: Pan troglodytes

<400> SEQUENCE: 88

Trp Gly Gln Gly Thr Lys Val Ile Val Ser Leu
1               5                   10

<210> SEQ ID NO 89
<211> LENGTH: 107
<212> TYPE: PRT
<213> ORGANISM: Pan troglodytes

<400> SEQUENCE: 89

Glu Leu Thr Gln Ser Pro Ser Ser Leu Ser Ala Ser Val Gly Asp Arg
1               5                   10                  15

Val Thr Ile Thr Cys Arg Ala Ser Gln Gly Ile Ser Asn Arg Leu Asn
            20                  25                  30

Trp Tyr Gln Gln Lys Pro Gly Gln Gly Pro Lys Phe Leu Met Tyr Asp
        35                  40                  45

Ala Ser Ser Leu Val Ser Gly Val Pro Ser Arg Phe Ser Gly Ser Gly
    50                  55                  60

Ser Gly Thr Asp Phe Thr Leu Thr Ile Ser Ser Leu Gln Pro Glu Asp
65                  70                  75                  80

Phe Ala Val Tyr Tyr Cys Gln Gln Phe Asn Ser Tyr Pro Leu Thr Phe
                85                  90                  95

Gly Gly Gly Thr Lys Leu Glu Ile Lys Arg Thr
            100                 105

<210> SEQ ID NO 90
<211> LENGTH: 21
<212> TYPE: PRT
<213> ORGANISM: Pan troglodytes

<400> SEQUENCE: 90

Glu Leu Thr Gln Ser Pro Ser Ser Leu Ser Ala Ser Val Gly Asp Arg
1               5                   10                  15

Val Thr Ile Thr Cys
            20

<210> SEQ ID NO 91
<211> LENGTH: 11
<212> TYPE: PRT
<213> ORGANISM: Pan troglodytes

<400> SEQUENCE: 91

Arg Ala Ser Gln Gly Ile Ser Asn Arg Leu Asn
1               5                   10

<210> SEQ ID NO 92
<211> LENGTH: 15
<212> TYPE: PRT
<213> ORGANISM: Pan troglodytes

<400> SEQUENCE: 92

Trp Tyr Gln Gln Lys Pro Gly Gln Gly Pro Lys Phe Leu Met Tyr
1               5                   10                  15

<210> SEQ ID NO 93
<211> LENGTH: 7
<212> TYPE: PRT
<213> ORGANISM: Pan troglodytes

<400> SEQUENCE: 93

Asp Ala Ser Ser Leu Val Ser
1               5

<210> SEQ ID NO 94
<211> LENGTH: 31
<212> TYPE: PRT
<213> ORGANISM: Pan troglodytes

<400> SEQUENCE: 94

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Val Tyr Tyr
            20                  25                  30

<210> SEQ ID NO 95
<211> LENGTH: 10
<212> TYPE: PRT
<213> ORGANISM: Pan troglodytes

<400> SEQUENCE: 95

Cys Gln Gln Phe Asn Ser Tyr Pro Leu Thr
1               5                   10

<210> SEQ ID NO 96
<211> LENGTH: 12
<212> TYPE: PRT
<213> ORGANISM: Pan troglodytes

<400> SEQUENCE: 96

Phe Gly Gly Gly Thr Lys Leu Glu Ile Lys Arg Thr
1               5                   10

<210> SEQ ID NO 97
<211> LENGTH: 122
<212> TYPE: PRT
<213> ORGANISM: Pan troglodytes

<400> SEQUENCE: 97

Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Ile Ser Asp Asn
            20                  25                  30

Val Met His Trp Val Arg Gln Ala Pro Gly Lys Gly Leu Glu Trp Val
        35                  40                  45

Ala Leu Ile Tyr Ser Ala Asp Thr Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asp Ser Leu Arg Pro Glu Asp Thr Ala Val Tyr Tyr Cys Ala
                85                  90                  95

Arg Glu Tyr Cys Thr Gly Asp Thr Cys Phe Ala His Phe Asp Tyr Trp
            100                 105                 110

Gly Gln Gly Thr Leu Val Ser Val Ser Ser
        115                 120

<210> SEQ ID NO 98
<211> LENGTH: 30
<212> TYPE: PRT
<213> ORGANISM: Pan troglodytes

<400> SEQUENCE: 98

Glu Val Gln Leu Leu Glu Ser Gly Gly Gly Leu Val Gln Pro Gly Gly
1               5                   10                  15

```
Ser Arg Arg Leu Ser Cys Ala Ala Ser Gly Phe Thr Ile Ser
            20                  25                  30

<210> SEQ ID NO 99
<211> LENGTH: 5
<212> TYPE: PRT
<213> ORGANISM: Pan troglodytes

<400> SEQUENCE: 99

Asp Asn Val Met His
1               5

<210> SEQ ID NO 100
<211> LENGTH: 13
<212> TYPE: PRT
<213> ORGANISM: Pan troglodytes

<400> SEQUENCE: 100

Trp Val Arg Gln Ala Pro Gly Lys Gly Leu Glu Trp Val
1               5                   10

<210> SEQ ID NO 101
<211> LENGTH: 17
<212> TYPE: PRT
<213> ORGANISM: Pan troglodytes

<400> SEQUENCE: 101

Ala Leu Ile Tyr Ser Ala Asp Thr Thr His Tyr Ala Asp Ser Val Lys
1               5                   10                  15

Gly

<210> SEQ ID NO 102
<211> LENGTH: 30
<212> TYPE: PRT
<213> ORGANISM: Pan troglodytes

<400> SEQUENCE: 102

Arg Phe Thr Ile Ser Arg Asp Asn Ser Lys Asn Thr Leu Tyr Leu Gln
1               5                   10                  15

Met Asp Ser Leu Arg Pro Glu Asp Thr Ala Val Tyr Tyr Cys
            20                  25                  30

<210> SEQ ID NO 103
<211> LENGTH: 16
<212> TYPE: PRT
<213> ORGANISM: Pan troglodytes

<400> SEQUENCE: 103

Ala Arg Glu Tyr Cys Thr Gly Asp Thr Cys Phe Ala His Phe Asp Tyr
1               5                   10                  15

<210> SEQ ID NO 104
<211> LENGTH: 11
<212> TYPE: PRT
<213> ORGANISM: Pan troglodytes

<400> SEQUENCE: 104

Trp Gly Gln Gly Thr Leu Val Ser Val Ser Ser
1               5                   10

<210> SEQ ID NO 105
<211> LENGTH: 108
<212> TYPE: PRT
```

<213> ORGANISM: Pan troglodytes

<400> SEQUENCE: 105

Glu Leu Gln Met Thr Gln Ser Pro Ser Ser Val Ser Ala Ser Val Gly
1               5                   10                  15
Asp Thr Val Thr Ile Ala Cys Arg Ala Ser Gln Ser Ile Thr Asn Tyr
            20                  25                  30
Leu Ser Trp Tyr Gln Gln Lys Pro Gly Lys Ala Pro Lys Leu Leu Ile
        35                  40                  45
Tyr His Ala Ser Thr Leu Gln Ser Gly Ile Pro Ser Arg Phe Ser Gly
    50                  55                  60
Ser Gly Ser Gly Thr Asp Phe Thr Leu Thr Ile Ser Ser Leu Gln Pro
65                  70                  75                  80
Asp Asp Phe Ala Thr Tyr Tyr Cys His Tyr Gly Tyr Gly Thr His Thr
                85                  90                  95
Phe Gly Gln Gly Thr Lys Leu Glu Ile Lys Arg Thr
            100                 105

<210> SEQ ID NO 106
<211> LENGTH: 23
<212> TYPE: PRT
<213> ORGANISM: Pan troglodytes

<400> SEQUENCE: 106

Glu Leu Gln Met Thr Gln Ser Pro Ser Ser Val Ser Ala Ser Val Gly
1               5                   10                  15
Asp Thr Val Thr Ile Ala Cys
            20

<210> SEQ ID NO 107
<211> LENGTH: 11
<212> TYPE: PRT
<213> ORGANISM: Pan troglodytes

<400> SEQUENCE: 107

Arg Ala Ser Gln Ser Ile Thr Asn Tyr Leu Ser
1               5                   10

<210> SEQ ID NO 108
<211> LENGTH: 15
<212> TYPE: PRT
<213> ORGANISM: Pan troglodytes

<400> SEQUENCE: 108

Trp Tyr Gln Gln Lys Pro Gly Lys Ala Pro Lys Leu Leu Ile Tyr
1               5                   10                  15

<210> SEQ ID NO 109
<211> LENGTH: 7
<212> TYPE: PRT
<213> ORGANISM: Pan troglodytes

<400> SEQUENCE: 109

His Ala Ser Thr Leu Gln Ser
1               5

<210> SEQ ID NO 110
<211> LENGTH: 31
<212> TYPE: PRT
<213> ORGANISM: Pan troglodytes

<400> SEQUENCE: 110

```
Gly Ile Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr
            20                  25                  30
```

<210> SEQ ID NO 111
<211> LENGTH: 9
<212> TYPE: PRT
<213> ORGANISM: Pan troglodytes

<400> SEQUENCE: 111

```
Cys His Tyr Gly Tyr Gly Thr His Thr
1               5
```

<210> SEQ ID NO 112
<211> LENGTH: 12
<212> TYPE: PRT
<213> ORGANISM: Pan troglodytes

<400> SEQUENCE: 112

```
Phe Gly Gln Gly Thr Lys Leu Glu Ile Lys Arg Thr
1               5                   10
```

<210> SEQ ID NO 113
<211> LENGTH: 122
<212> TYPE: PRT
<213> ORGANISM: Pan troglodytes

<400> SEQUENCE: 113

```
Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Ile Ser Asp Asn
            20                  25                  30

Val Met His Trp Val Arg Gln Ala Pro Gly Lys Gly Leu Glu Trp Val
        35                  40                  45

Ala Leu Ile Tyr Ser Ala Asp Ser Thr His Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asp Gly Leu Arg Pro Glu Asp Thr Ala Val Tyr Tyr Cys Ala
                85                  90                  95

Arg Glu Tyr Cys Thr Gly Gly Thr Cys Phe Ala His Phe Asp Tyr Trp
            100                 105                 110

Gly Gln Gly Thr Leu Val Thr Val Ser Ser
        115                 120
```

<210> SEQ ID NO 114
<211> LENGTH: 30
<212> TYPE: PRT
<213> ORGANISM: Pan troglodytes

<400> SEQUENCE: 114

```
Glu Val Gln Leu Leu Glu Ser Gly Gly Gly Leu Val Gln Pro Gly Gly
1               5                   10                  15

Ser Arg Arg Leu Ser Cys Ala Ala Ser Gly Phe Thr Ile Ser
            20                  25                  30
```

<210> SEQ ID NO 115
<211> LENGTH: 5
<212> TYPE: PRT

<213> ORGANISM: Pan troglodytes

<400> SEQUENCE: 115

Asp Asn Val Met His
1               5

<210> SEQ ID NO 116
<211> LENGTH: 13
<212> TYPE: PRT
<213> ORGANISM: Pan troglodytes

<400> SEQUENCE: 116

Trp Val Arg Gln Ala Pro Gly Lys Gly Leu Glu Trp Val
1               5                   10

<210> SEQ ID NO 117
<211> LENGTH: 17
<212> TYPE: PRT
<213> ORGANISM: Pan troglodytes

<400> SEQUENCE: 117

Ala Leu Ile Tyr Ser Ala Asp Ser Thr His Tyr Ala Asp Ser Val Lys
1               5                   10                  15

Gly

<210> SEQ ID NO 118
<211> LENGTH: 30
<212> TYPE: PRT
<213> ORGANISM: Pan troglodytes

<400> SEQUENCE: 118

Arg Phe Thr Ile Ser Arg Asp Asn Ser Lys Asn Thr Leu Tyr Leu Gln
1               5                   10                  15

Met Asp Gly Leu Arg Pro Glu Asp Thr Ala Val Tyr Tyr Cys
            20                  25                  30

<210> SEQ ID NO 119
<211> LENGTH: 16
<212> TYPE: PRT
<213> ORGANISM: Pan troglodytes

<400> SEQUENCE: 119

Ala Arg Glu Tyr Cys Thr Gly Gly Thr Cys Phe Ala His Phe Asp Tyr
1               5                   10                  15

<210> SEQ ID NO 120
<211> LENGTH: 11
<212> TYPE: PRT
<213> ORGANISM: Pan troglodytes

<400> SEQUENCE: 120

Trp Gly Gln Gly Thr Leu Val Thr Val Ser Ser
1               5                   10

<210> SEQ ID NO 121
<211> LENGTH: 108
<212> TYPE: PRT
<213> ORGANISM: Pan troglodytes

<400> SEQUENCE: 121

Glu Leu Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Thr Asn Tyr

```
                20                  25                  30
Leu Ser Trp Tyr Gln Gln Lys Pro Gly Lys Ala Pro Lys Leu Ile
            35                  40                  45

Ser Tyr Ser Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys His Tyr Gly Tyr Gly Thr His Thr
                85                  90                  95

Phe Gly Pro Gly Thr Lys Val Asp Ile Lys Arg Thr
            100                 105

<210> SEQ ID NO 122
<211> LENGTH: 23
<212> TYPE: PRT
<213> ORGANISM: Pan troglodytes

<400> SEQUENCE: 122

Glu Leu Gln Met Thr Gln Ser Pro Ser Ser Leu Ser Ala Ser Val Gly
1               5                   10                  15

Asp Arg Val Thr Ile Thr Cys
            20

<210> SEQ ID NO 123
<211> LENGTH: 11
<212> TYPE: PRT
<213> ORGANISM: Pan troglodytes

<400> SEQUENCE: 123

Arg Ala Ser Gln Ser Ile Thr Asn Tyr Leu Ser
1               5                   10

<210> SEQ ID NO 124
<211> LENGTH: 15
<212> TYPE: PRT
<213> ORGANISM: Pan troglodytes

<400> SEQUENCE: 124

Trp Tyr Gln Gln Lys Pro Gly Lys Ala Pro Lys Leu Leu Ile Ser
1               5                   10                  15

<210> SEQ ID NO 125
<211> LENGTH: 7
<212> TYPE: PRT
<213> ORGANISM: Pan troglodytes

<400> SEQUENCE: 125

Tyr Ser Ser Thr Leu Gln Ser
1               5

<210> SEQ ID NO 126
<211> LENGTH: 31
<212> TYPE: PRT
<213> ORGANISM: Pan troglodytes

<400> SEQUENCE: 126

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr
            20                  25                  30
```

```
<210> SEQ ID NO 127
<211> LENGTH: 9
<212> TYPE: PRT
<213> ORGANISM: Pan troglodytes

<400> SEQUENCE: 127

Cys His Tyr Gly Tyr Gly Thr His Thr
 1               5

<210> SEQ ID NO 128
<211> LENGTH: 12
<212> TYPE: PRT
<213> ORGANISM: Pan troglodytes

<400> SEQUENCE: 128

Phe Gly Pro Gly Thr Lys Val Asp Ile Lys Arg Thr
 1               5                  10

<210> SEQ ID NO 129
<211> LENGTH: 122
<212> TYPE: PRT
<213> ORGANISM: Pan troglodytes

<400> SEQUENCE: 129

Glu Val Gln Leu Leu Glu Ser Gly Gly Gly Leu Val Gln Pro Gly Gly
 1               5                  10                  15

Ser Arg Arg Leu Ser Cys Ala Ala Ser Gly Phe Thr Ile Ser Asp Asn
                20                  25                  30

Val Met His Trp Val Arg Gln Ala Pro Gly Lys Gly Leu Glu Trp Val
            35                  40                  45

Ala Leu Ile Tyr Ser Ala Asp Thr Thr His Tyr Ala Asp Ser Val Lys
        50                  55                  60

Gly Arg Phe Thr Ile Ser Arg Asp Asn Ser Lys Asn Thr Leu Tyr Leu
 65                  70                  75                  80

Gln Met Asp Ser Leu Arg Pro Glu Asp Thr Ala Val Tyr Tyr Cys Ala
                85                  90                  95

Arg Glu Tyr Cys Thr Gly Asp Thr Cys Phe Ala His Phe Asp Tyr Trp
            100                 105                 110

Gly Gln Gly Thr Leu Val Ser Val Ser Ser
        115                 120

<210> SEQ ID NO 130
<211> LENGTH: 30
<212> TYPE: PRT
<213> ORGANISM: Pan troglodytes

<400> SEQUENCE: 130

Glu Val Gln Leu Leu Glu Ser Gly Gly Gly Leu Val Gln Pro Gly Gly
 1               5                  10                  15

Ser Arg Arg Leu Ser Cys Ala Ala Ser Gly Phe Thr Ile Ser
                20                  25                  30

<210> SEQ ID NO 131
<211> LENGTH: 5
<212> TYPE: PRT
<213> ORGANISM: Pan troglodytes

<400> SEQUENCE: 131

Asp Asn Val Met His
 1               5
```

```
<210> SEQ ID NO 132
<211> LENGTH: 13
<212> TYPE: PRT
<213> ORGANISM: Pan troglodytes

<400> SEQUENCE: 132

Trp Val Arg Gln Ala Pro Gly Lys Gly Leu Glu Trp Val
1               5                   10

<210> SEQ ID NO 133
<211> LENGTH: 17
<212> TYPE: PRT
<213> ORGANISM: Pan troglodytes

<400> SEQUENCE: 133

Ala Leu Ile Tyr Ser Ala Asp Thr Thr His Tyr Ala Asp Ser Val Lys
1               5                   10                  15

Gly

<210> SEQ ID NO 134
<211> LENGTH: 30
<212> TYPE: PRT
<213> ORGANISM: Pan troglodytes

<400> SEQUENCE: 134

Arg Phe Thr Ile Ser Arg Asp Asn Ser Lys Asn Thr Leu Tyr Leu Gln
1               5                   10                  15

Met Asp Ser Leu Arg Pro Glu Asp Thr Ala Val Tyr Tyr Cys
            20                  25                  30

<210> SEQ ID NO 135
<211> LENGTH: 16
<212> TYPE: PRT
<213> ORGANISM: Pan troglodytes

<400> SEQUENCE: 135

Ala Arg Glu Tyr Cys Thr Gly Asp Thr Cys Phe Ala His Phe Asp Tyr
1               5                   10                  15

<210> SEQ ID NO 136
<211> LENGTH: 11
<212> TYPE: PRT
<213> ORGANISM: Pan troglodytes

<400> SEQUENCE: 136

Trp Gly Gln Gly Thr Leu Val Ser Val Ser Ser
1               5                   10

<210> SEQ ID NO 137
<211> LENGTH: 106
<212> TYPE: PRT
<213> ORGANISM: Pan troglodytes

<400> SEQUENCE: 137

Glu Leu Thr Gln Ser Pro Ser Ser Val Ser Ala Ser Val Gly Asp Arg
1               5                   10                  15

Val Thr Ile Thr Cys Arg Ala Ser Gln Thr Ile Thr Asn Tyr Val Ser
            20                  25                  30

Trp Tyr Gln Gln Lys Pro Gly Lys Ala Pro Asn Leu Leu Ile Tyr Phe
        35                  40                  45

Ala Ser Thr Leu His Ser Gly Val Pro Ser Arg Phe Ser Gly Ser Gly
    50                  55                  60
```

```
Ser Gly Thr Asp Phe Thr Leu Thr Ile Asn Ser Leu Gln Pro Asp Asp
 65                  70                  75                  80

Phe Ala Thr Tyr Tyr Cys Gln Tyr Gly Tyr Gly Thr Gln Thr Phe Gly
                 85                  90                  95

Gln Gly Thr Lys Leu Glu Val Lys Arg Thr
            100                 105

<210> SEQ ID NO 138
<211> LENGTH: 21
<212> TYPE: PRT
<213> ORGANISM: Pan troglodytes

<400> SEQUENCE: 138

Glu Leu Thr Gln Ser Pro Ser Ser Val Ser Ala Ser Val Gly Asp Arg
  1               5                  10                  15

Val Thr Ile Thr Cys
             20

<210> SEQ ID NO 139
<211> LENGTH: 11
<212> TYPE: PRT
<213> ORGANISM: Pan troglodytes

<400> SEQUENCE: 139

Arg Ala Ser Gln Thr Ile Thr Asn Tyr Val Ser
  1               5                  10

<210> SEQ ID NO 140
<211> LENGTH: 15
<212> TYPE: PRT
<213> ORGANISM: Pan troglodytes

<400> SEQUENCE: 140

Trp Tyr Gln Gln Lys Pro Gly Lys Ala Pro Asn Leu Leu Ile Tyr
  1               5                  10                  15

<210> SEQ ID NO 141
<211> LENGTH: 7
<212> TYPE: PRT
<213> ORGANISM: Pan troglodytes

<400> SEQUENCE: 141

Phe Ala Ser Thr Leu His Ser
  1               5

<210> SEQ ID NO 142
<211> LENGTH: 31
<212> TYPE: PRT
<213> ORGANISM: Pan troglodytes

<400> SEQUENCE: 142

Gly Val Pro Ser Arg Phe Ser Gly Ser Gly Ser Gly Thr Asp Phe Thr
  1               5                  10                  15

Leu Thr Ile Asn Ser Leu Gln Pro Asp Asp Phe Ala Thr Tyr Tyr
             20                  25                  30

<210> SEQ ID NO 143
<211> LENGTH: 9
<212> TYPE: PRT
<213> ORGANISM: Pan troglodytes

<400> SEQUENCE: 143

Cys Gln Tyr Gly Tyr Gly Thr Gln Thr
```

```
<210> SEQ ID NO 144
<211> LENGTH: 12
<212> TYPE: PRT
<213> ORGANISM: Pan troglodytes

<400> SEQUENCE: 144

Phe Gly Gln Gly Thr Lys Leu Glu Val Lys Arg Thr
 1               5                  10

<210> SEQ ID NO 145
<211> LENGTH: 123
<212> TYPE: PRT
<213> ORGANISM: Pan troglodytes

<400> SEQUENCE: 145

Glu Val Gln Leu Leu Glu Gln Ser Gly Gly Gly Leu Val Gln Pro Gly
 1               5                  10                  15

Gly Ser Arg Arg Leu Ser Cys Ala Val Ser Gly Phe Thr Ile Ser Asp
            20                  25                  30

Asn Val Met His Trp Val Arg Gln Ala Pro Gly Lys Gly Leu Glu Trp
        35                  40                  45

Val Ala Leu Ile Tyr Ser Ala Asp Thr Thr His Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asp Ser Leu Arg Pro Glu Asp Thr Ala Val Tyr Tyr Cys
                85                  90                  95

Ala Arg Glu Tyr Cys Thr Gly Gly Thr Cys Phe Ala His Phe Asp Tyr
            100                 105                 110

Trp Gly Gln Gly Thr Leu Val Thr Val Ser Ser
        115                 120

<210> SEQ ID NO 146
<211> LENGTH: 31
<212> TYPE: PRT
<213> ORGANISM: Pan troglodytes

<400> SEQUENCE: 146

Glu Val Gln Leu Leu Glu Gln Ser Gly Gly Gly Leu Val Gln Pro Gly
 1               5                  10                  15

Gly Ser Arg Arg Leu Ser Cys Ala Val Ser Gly Phe Thr Ile Ser
            20                  25                  30

<210> SEQ ID NO 147
<211> LENGTH: 5
<212> TYPE: PRT
<213> ORGANISM: Pan troglodytes

<400> SEQUENCE: 147

Asp Asn Val Met His
 1               5

<210> SEQ ID NO 148
<211> LENGTH: 13
<212> TYPE: PRT
<213> ORGANISM: Pan troglodytes

<400> SEQUENCE: 148

Trp Val Arg Gln Ala Pro Gly Lys Gly Leu Glu Trp Val
 1               5                  10
```

<210> SEQ ID NO 149
<211> LENGTH: 17
<212> TYPE: PRT
<213> ORGANISM: Pan troglodytes

<400> SEQUENCE: 149

Ala Leu Ile Tyr Ser Ala Asp Thr Thr His Tyr Ala Asp Ser Val Lys
1               5                   10                  15

Gly

<210> SEQ ID NO 150
<211> LENGTH: 30
<212> TYPE: PRT
<213> ORGANISM: Pan troglodytes

<400> SEQUENCE: 150

Arg Phe Thr Ile Ser Arg Asp Asn Ser Lys Asn Thr Leu Tyr Leu Gln
1               5                   10                  15

Met Asp Ser Leu Arg Pro Glu Asp Thr Ala Val Tyr Tyr Cys
            20                  25                  30

<210> SEQ ID NO 151
<211> LENGTH: 16
<212> TYPE: PRT
<213> ORGANISM: Pan troglodytes

<400> SEQUENCE: 151

Ala Arg Glu Tyr Cys Thr Gly Gly Thr Cys Phe Ala His Phe Asp Tyr
1               5                   10                  15

<210> SEQ ID NO 152
<211> LENGTH: 11
<212> TYPE: PRT
<213> ORGANISM: Pan troglodytes

<400> SEQUENCE: 152

Trp Gly Gln Gly Thr Leu Val Thr Val Ser Ser
1               5                   10

<210> SEQ ID NO 153
<211> LENGTH: 106
<212> TYPE: PRT
<213> ORGANISM: Pan troglodytes

<400> SEQUENCE: 153

Glu Leu Thr Gln Ser Pro Ser Ser Val Ser Ala Ser Val Gly Asp Thr
1               5                   10                  15

Val Thr Ile Ala Cys Arg Ala Ser Gln Ser Ile Thr Asn Tyr Leu Ser
            20                  25                  30

Trp Tyr Gln Gln Lys Pro Gly Lys Ala Pro Lys Leu Leu Ile Tyr His
        35                  40                  45

Ala Ser Thr Leu Gln Ser Gly Ile Pro Ser Arg Phe Ser Gly Ser Gly
    50                  55                  60

Ser Gly Thr Asp Phe Thr Leu Thr Ile Ser Ser Leu Gln Pro Asp Asp
65                  70                  75                  80

Phe Ala Thr Tyr Tyr Cys His Tyr Gly Tyr Gly Thr His Thr Phe Gly
                85                  90                  95

Gln Gly Thr Lys Leu Glu Ile Lys Arg Thr
            100                 105

<210> SEQ ID NO 154
<211> LENGTH: 21
<212> TYPE: PRT
<213> ORGANISM: Pan troglodytes

<400> SEQUENCE: 154

Glu Leu Thr Gln Ser Pro Ser Ser Val Ser Ala Ser Val Gly Asp Thr
1               5                   10                  15

Val Thr Ile Ala Cys
            20

<210> SEQ ID NO 155
<211> LENGTH: 11
<212> TYPE: PRT
<213> ORGANISM: Pan troglodytes

<400> SEQUENCE: 155

Arg Ala Ser Gln Ser Ile Thr Asn Tyr Leu Ser
1               5                   10

<210> SEQ ID NO 156
<211> LENGTH: 15
<212> TYPE: PRT
<213> ORGANISM: Pan troglodytes

<400> SEQUENCE: 156

Trp Tyr Gln Gln Lys Pro Gly Lys Ala Pro Lys Leu Leu Ile Tyr
1               5                   10                  15

<210> SEQ ID NO 157
<211> LENGTH: 7
<212> TYPE: PRT
<213> ORGANISM: Pan troglodytes

<400> SEQUENCE: 157

His Ala Ser Thr Leu Gln Ser
1               5

<210> SEQ ID NO 158
<211> LENGTH: 31
<212> TYPE: PRT
<213> ORGANISM: Pan troglodytes

<400> SEQUENCE: 158

Gly Ile Pro Ser Arg Phe Ser Gly Ser Gly Ser Gly Thr Asp Phe Thr
1               5                   10                  15

Leu Thr Ile Ser Ser Leu Gln Pro Asp Asp Phe Ala Thr Tyr Tyr
            20                  25                  30

<210> SEQ ID NO 159
<211> LENGTH: 9
<212> TYPE: PRT
<213> ORGANISM: Pan troglodytes

<400> SEQUENCE: 159

Cys His Tyr Gly Tyr Gly Thr His Thr
1               5

<210> SEQ ID NO 160
<211> LENGTH: 12
<212> TYPE: PRT
<213> ORGANISM: Pan troglodytes

```
<400> SEQUENCE: 160

Phe Gly Gln Gly Thr Lys Leu Glu Ile Lys Arg Thr
1               5                   10

<210> SEQ ID NO 161
<211> LENGTH: 125
<212> TYPE: PRT
<213> ORGANISM: Pan troglodytes

<400> SEQUENCE: 161

Glu Val Gln Leu Leu Glu Ser Gly Pro Gly Leu Val Lys Pro Ser Gln
1               5                   10                  15

Thr Leu Ser Leu Thr Cys Ala Val Ser Gly Gly Ser Ile Thr Ser Asp
            20                  25                  30

His Tyr Phe Trp Ser Trp Met Arg Gln Ala Pro Gly Arg Gly Leu Glu
        35                  40                  45

Trp Ile Gly Tyr Ile Ser Tyr Arg Gly Thr Thr Tyr Tyr Asn Pro Ser
    50                  55                  60

Leu Lys Ser Arg Val Thr Met Ser Val Thr Ala Ala Lys Asn Thr Leu
65                  70                  75                  80

Tyr Leu Gln Met Asp Gly Leu Arg Pro Glu Asp Thr Ala Val Tyr Tyr
                85                  90                  95

Cys Ala Arg Ala Ser Val Thr Ala Gly Met Pro Ala Ala Gly Thr Leu
            100                 105                 110

Asp His Trp Gly Gln Gly Thr Leu Val Thr Val Ser Ser
        115                 120                 125

<210> SEQ ID NO 162
<211> LENGTH: 32
<212> TYPE: PRT
<213> ORGANISM: Pan troglodytes

<400> SEQUENCE: 162

Glu Val Gln Leu Leu Glu Ser Gly Pro Gly Leu Val Lys Pro Ser Gln
1               5                   10                  15

Thr Leu Ser Leu Thr Cys Ala Val Ser Gly Gly Ser Ile Thr Ser Asp
            20                  25                  30

<210> SEQ ID NO 163
<211> LENGTH: 5
<212> TYPE: PRT
<213> ORGANISM: Pan troglodytes

<400> SEQUENCE: 163

His Tyr Phe Trp Ser
1               5

<210> SEQ ID NO 164
<211> LENGTH: 13
<212> TYPE: PRT
<213> ORGANISM: Pan troglodytes

<400> SEQUENCE: 164

Trp Met Arg Gln Ala Pro Gly Arg Gly Leu Glu Trp Ile
1               5                   10

<210> SEQ ID NO 165
<211> LENGTH: 17
<212> TYPE: PRT
<213> ORGANISM: Pan troglodytes
```

```
<400> SEQUENCE: 165

Gly Tyr Ile Ser Tyr Arg Gly Thr Thr Tyr Tyr Asn Pro Ser Leu Lys
 1               5                  10                  15

Ser

<210> SEQ ID NO 166
<211> LENGTH: 30
<212> TYPE: PRT
<213> ORGANISM: Pan troglodytes

<400> SEQUENCE: 166

Arg Val Thr Met Ser Val Thr Ala Ala Lys Asn Thr Leu Tyr Leu Gln
 1               5                  10                  15

Met Asp Gly Leu Arg Pro Glu Asp Thr Ala Val Tyr Tyr Cys
            20                  25                  30

<210> SEQ ID NO 167
<211> LENGTH: 17
<212> TYPE: PRT
<213> ORGANISM: Pan troglodytes

<400> SEQUENCE: 167

Ala Arg Ala Ser Val Thr Ala Gly Met Pro Ala Ala Gly Thr Leu Asp
 1               5                  10                  15

His

<210> SEQ ID NO 168
<211> LENGTH: 11
<212> TYPE: PRT
<213> ORGANISM: Pan troglodytes

<400> SEQUENCE: 168

Trp Gly Gln Gly Thr Leu Val Thr Val Ser Ser
 1               5                  10

<210> SEQ ID NO 169
<211> LENGTH: 109
<212> TYPE: PRT
<213> ORGANISM: Pan troglodytes

<400> SEQUENCE: 169

Glu Leu Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Glu
            20                  25                  30

Leu Asn Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Asn Ser Phe Pro Trp
                85                  90                  95

Thr Phe Gly Gln Gly Thr Lys Leu Glu Ile Lys Arg Thr
            100                 105

<210> SEQ ID NO 170
<211> LENGTH: 23
<212> TYPE: PRT
<213> ORGANISM: Pan troglodytes
```

-continued

```
<400> SEQUENCE: 170

Glu Leu Gln Met Thr Gln Ser Pro Ser Ser Leu Ser Ala Ser Val Gly
1               5                   10                  15

Asp Arg Val Thr Ile Thr Cys
            20

<210> SEQ ID NO 171
<211> LENGTH: 11
<212> TYPE: PRT
<213> ORGANISM: Pan troglodytes

<400> SEQUENCE: 171

Arg Ala Ser Gln Gly Ile Ser Ser Glu Leu Asn
1               5                   10

<210> SEQ ID NO 172
<211> LENGTH: 15
<212> TYPE: PRT
<213> ORGANISM: Pan troglodytes

<400> SEQUENCE: 172

Trp Tyr Gln Gln Lys Pro Gly Lys Ala Pro Lys Leu Leu Ile Tyr
1               5                   10                  15

<210> SEQ ID NO 173
<211> LENGTH: 7
<212> TYPE: PRT
<213> ORGANISM: Pan troglodytes

<400> SEQUENCE: 173

Asp Ala Ser Ser Leu Glu Ser
1               5

<210> SEQ ID NO 174
<211> LENGTH: 31
<212> TYPE: PRT
<213> ORGANISM: Pan troglodytes

<400> SEQUENCE: 174

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr
            20                  25                  30

<210> SEQ ID NO 175
<211> LENGTH: 10
<212> TYPE: PRT
<213> ORGANISM: Pan troglodytes

<400> SEQUENCE: 175

Cys Gln His Phe Asn Ser Phe Pro Trp Thr
1               5                   10

<210> SEQ ID NO 176
<211> LENGTH: 12
<212> TYPE: PRT
<213> ORGANISM: Pan troglodytes

<400> SEQUENCE: 176

Phe Gly Gln Gly Thr Lys Leu Glu Ile Lys Arg Thr
1               5                   10
```

```
<210> SEQ ID NO 177
<211> LENGTH: 121
<212> TYPE: PRT
<213> ORGANISM: Pan troglodytes

<400> SEQUENCE: 177

Glu Val Gln Leu Leu Glu Glu Ser Gly Ala Glu Val Lys Lys Pro Gly
 1               5                  10                  15

Ser Ser Val Lys Val Ser Cys Lys Val Ser Gly Gly Thr Phe Ser Arg
            20                  25                  30

Asn Pro Ile Ser Trp Val Arg Gln Ala Pro Gly Gln Gly Leu Glu Trp
        35                  40                  45

Met Gly Val Ile Val Pro Ile Val Gly Thr Thr Lys His Ala Gln Lys
    50                  55                  60

Phe Gln Gly Arg Val Thr Ile Ile Ala Asp Glu Ser Thr Ser Thr Ala
65                  70                  75                  80

Tyr Met Glu Leu Ser Ser Leu Arg Ser Glu Asp Thr Ala Val Tyr Tyr
                85                  90                  95

Cys Ala Thr Tyr Tyr Ala Asp Gly Ser Ser Tyr Ser Glu Tyr Trp Gly
            100                 105                 110

Gln Gly Thr Leu Val Thr Val Ser Ser
        115                 120

<210> SEQ ID NO 178
<211> LENGTH: 31
<212> TYPE: PRT
<213> ORGANISM: Pan troglodytes

<400> SEQUENCE: 178

Glu Val Gln Leu Leu Glu Glu Ser Gly Ala Glu Val Lys Lys Pro Gly
 1               5                  10                  15

Ser Ser Val Lys Val Ser Cys Lys Val Ser Gly Gly Thr Phe Ser
            20                  25                  30

<210> SEQ ID NO 179
<211> LENGTH: 5
<212> TYPE: PRT
<213> ORGANISM: Pan troglodytes

<400> SEQUENCE: 179

Arg Asn Pro Ile Ser
 1               5

<210> SEQ ID NO 180
<211> LENGTH: 13
<212> TYPE: PRT
<213> ORGANISM: Pan troglodytes

<400> SEQUENCE: 180

Trp Val Arg Gln Ala Pro Gly Gln Gly Leu Glu Trp Met
 1               5                  10

<210> SEQ ID NO 181
<211> LENGTH: 18
<212> TYPE: PRT
<213> ORGANISM: Pan troglodytes

<400> SEQUENCE: 181

Gly Val Ile Val Pro Ile Val Gly Thr Thr Lys His Ala Gln Lys Phe
 1               5                  10                  15

Gln Gly
```

<210> SEQ ID NO 182
<211> LENGTH: 30
<212> TYPE: PRT
<213> ORGANISM: Pan troglodytes

<400> SEQUENCE: 182

Arg Val Thr Ile Ile Ala Asp Glu Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 183
<211> LENGTH: 13
<212> TYPE: PRT
<213> ORGANISM: Pan troglodytes

<400> SEQUENCE: 183

Ala Thr Tyr Tyr Ala Asp Gly Ser Ser Tyr Ser Glu Tyr
1               5                   10

<210> SEQ ID NO 184
<211> LENGTH: 11
<212> TYPE: PRT
<213> ORGANISM: Pan troglodytes

<400> SEQUENCE: 184

Trp Gly Gln Gly Thr Leu Val Thr Val Ser Ser
1               5                   10

<210> SEQ ID NO 185
<211> LENGTH: 114
<212> TYPE: PRT
<213> ORGANISM: Pan troglodytes

<400> SEQUENCE: 185

Glu Leu Gln Met Thr Gln Ser Pro Leu Ser Leu Ser Val Ala Pro Gly
1               5                   10                  15

Gln Pro Ala Ser Ile Ser Cys Lys Ser Ser Gln Ser Leu Leu His Ser
            20                  25                  30

Asp Gly Asn Thr Tyr Leu Phe Trp Tyr Leu Gln Lys Ser Gly Gln Ser
        35                  40                  45

Pro Gln Leu Leu Ile Tyr Gly Leu Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Gln Val Glu Ala Glu Asp Val Gly Val Phe Tyr Cys Met Gln Gly
                85                  90                  95

Thr Gln Leu Pro Tyr Thr Phe Gly Gln Gly Thr Lys Leu Glu Ile Lys
            100                 105                 110

Arg Thr

<210> SEQ ID NO 186
<211> LENGTH: 23
<212> TYPE: PRT
<213> ORGANISM: Pan troglodytes

<400> SEQUENCE: 186

Glu Leu Gln Met Thr Gln Ser Pro Leu Ser Leu Ser Val Ala Pro Gly
1               5                   10                  15

Gln Pro Ala Ser Ile Ser Cys
            20

<210> SEQ ID NO 187
<211> LENGTH: 16
<212> TYPE: PRT
<213> ORGANISM: Pan troglodytes

<400> SEQUENCE: 187

Lys Ser Ser Gln Ser Leu Leu His Ser Asp Gly Asn Thr Tyr Leu Phe
1               5                   10                  15

<210> SEQ ID NO 188
<211> LENGTH: 15
<212> TYPE: PRT
<213> ORGANISM: Pan troglodytes

<400> SEQUENCE: 188

Trp Tyr Leu Gln Lys Ser Gly Gln Ser Pro Gln Leu Leu Ile Tyr
1               5                   10                  15

<210> SEQ ID NO 189
<211> LENGTH: 7
<212> TYPE: PRT
<213> ORGANISM: Pan troglodytes

<400> SEQUENCE: 189

Gly Leu Ser Asn Arg Ala Ser
1               5

<210> SEQ ID NO 190
<211> LENGTH: 31
<212> TYPE: PRT
<213> ORGANISM: Pan troglodytes

<400> SEQUENCE: 190

Gly Val Pro Asp Arg Phe Ser Gly Ser Gly Ser Gly Thr Asp Phe Thr
1               5                   10                  15

Leu Lys Ile Ser Gln Val Glu Ala Glu Asp Val Gly Val Phe Tyr
            20                  25                  30

<210> SEQ ID NO 191
<211> LENGTH: 10
<212> TYPE: PRT
<213> ORGANISM: Pan troglodytes

<400> SEQUENCE: 191

Cys Met Gln Gly Thr Gln Leu Pro Tyr Thr
1               5                   10

<210> SEQ ID NO 192
<211> LENGTH: 12
<212> TYPE: PRT
<213> ORGANISM: Pan troglodytes

<400> SEQUENCE: 192

Phe Gly Gln Gly Thr Lys Leu Glu Ile Lys Arg Thr
1               5                   10

<210> SEQ ID NO 193
<211> LENGTH: 21
<212> TYPE: DNA
<213> ORGANISM: Artificial Sequence
<220> FEATURE:
<223> OTHER INFORMATION: primer for sequencing VL segment

```
<400> SEQUENCE: 193
acagctatcg cgattgcagt g                                          21

<210> SEQ ID NO 194
<211> LENGTH: 21
<212> TYPE: DNA
<213> ORGANISM: Artificial Sequence
<220> FEATURE:
<223> OTHER INFORMATION: primer for sequencing VL segment

<400> SEQUENCE: 194
cacctgatcc tcagatggcg g                                          21

<210> SEQ ID NO 195
<211> LENGTH: 21
<212> TYPE: DNA
<213> ORGANISM: Artificial Sequence
<220> FEATURE:
<223> OTHER INFORMATION: primer for sequencing VH segment

<400> SEQUENCE: 195
attgcctacg gcagccgctg g                                          21

<210> SEQ ID NO 196
<211> LENGTH: 21
<212> TYPE: DNA
<213> ORGANISM: Artificial Sequence
<220> FEATURE:
<223> OTHER INFORMATION: primer for sequencing VH segment

<400> SEQUENCE: 196
ggaagtagtc cttgaccagg c                                          21

<210> SEQ ID NO 197
<211> LENGTH: 30
<212> TYPE: DNA
<213> ORGANISM: Artificial Sequence
<220> FEATURE:
<223> OTHER INFORMATION: primer

<400> SEQUENCE: 197
gacaaaactc acacatgtcc accgtgccca                                 30

<210> SEQ ID NO 198
<211> LENGTH: 23
<212> TYPE: DNA
<213> ORGANISM: Artificial Sequence
<220> FEATURE:
<223> OTHER INFORMATION: primer

<400> SEQUENCE: 198
agtcttgtta ctgagcggat tcc                                        23

<210> SEQ ID NO 199
<211> LENGTH: 25
<212> TYPE: DNA
<213> ORGANISM: Artificial Sequence
<220> FEATURE:
<223> OTHER INFORMATION: primer

<400> SEQUENCE: 199
gtttgacagc ttatcatcga taagc                                      25

<210> SEQ ID NO 200
```

```
<211> LENGTH: 14
<212> TYPE: PRT
<213> ORGANISM: Artificial Sequence
<220> FEATURE:
<223> OTHER INFORMATION: control peptide

<400> SEQUENCE: 200

Gly Ala Met His Ser Ala Leu Ala Gly Ala Thr Glu Val Asp
1               5                   10

<210> SEQ ID NO 201
<211> LENGTH: 9
<212> TYPE: PRT
<213> ORGANISM: Artificial Sequence
<220> FEATURE:
<223> OTHER INFORMATION: control peptide

<400> SEQUENCE: 201

Trp Trp Trp Gln Thr Phe Asp Ala Arg
1               5

<210> SEQ ID NO 202
<211> LENGTH: 15
<212> TYPE: PRT
<213> ORGANISM: Artificial Sequence
<220> FEATURE:
<223> OTHER INFORMATION: fusion peptide

<400> SEQUENCE: 202

Asp Arg Gly Trp Gly Asn Gly Ser Gly Leu Phe Gly Lys Gly Gly
1               5                   10                  15

<210> SEQ ID NO 203
<211> LENGTH: 32
<212> TYPE: PRT
<213> ORGANISM: Flavivirus DENV-2

<400> SEQUENCE: 203

Arg Phe Val Cys Lys His Ser Met Val Asp Arg Gly Trp Gly Asn Gly
1               5                   10                  15
    Cys Gly Leu Phe Gly Lys Gly Gly Ile Val Thr Cys Ala Met Phe Thr
            20                  25                  30

<210> SEQ ID NO 204
<211> LENGTH: 32
<212> TYPE: PRT
<213> ORGANISM: Flavivirus DENV-2

<400> SEQUENCE: 204

Arg Phe Val Cys Lys His Ser Met Val Asp Arg Gly Trp Gly Asn Gly
1               5                   10                  15
Cys Val Leu Phe Gly Lys Gly Gly Ile Val Thr Cys Ala Met Phe Thr
            20                  25                  30

<210> SEQ ID NO 205
<211> LENGTH: 32
<212> TYPE: PRT
<213> ORGANISM: Flavivirus DENV-1

<400> SEQUENCE: 205

Asn Phe Val Cys Arg Arg Thr Phe Val Asp Arg Gly Trp Gly Asn Gly
1               5                   10                  15
Cys Gly Leu Phe Gly Lys Gly Ser Leu Ile Thr Cys Ala Lys Phe Lys
            20                  25                  30
```

<210> SEQ ID NO 206
<211> LENGTH: 32
<212> TYPE: PRT
<213> ORGANISM: Flavivirus DENV-3

<400> SEQUENCE: 206

Asn Tyr Val Cys Lys His Thr Tyr Val Asp Arg Gly Trp Gly Asn Gly
1               5                   10                  15

Cys Gly Leu Phe Gly Lys Gly Ser Leu Val Thr Cys Ala Lys Phe Gln
            20                  25                  30

<210> SEQ ID NO 207
<211> LENGTH: 32
<212> TYPE: PRT
<213> ORGANISM: Flavivirus DENV-4

<400> SEQUENCE: 207

Gln Tyr Ile Cys Arg Arg Asp Val Val Asp Arg Gly Trp Gly Asn Gly
1               5                   10                  15

Cys Gly Leu Phe Gly Lys Gly Gly Val Val Thr Cys Ala Lys Phe Ser
            20                  25                  30

<210> SEQ ID NO 208
<211> LENGTH: 32
<212> TYPE: PRT
<213> ORGANISM: Flavivirus WNV

<400> SEQUENCE: 208

Ala Phe Val Cys Arg Gln Gly Val Val Asp Arg Gly Trp Gly Asn Gly
1               5                   10                  15

Cys Gly Leu Phe Gly Lys Gly Ser Ile Asp Thr Cys Ala Lys Phe Ala
            20                  25                  30

<210> SEQ ID NO 209
<211> LENGTH: 32
<212> TYPE: PRT
<213> ORGANISM: Flavivirus JEV

<400> SEQUENCE: 209

Ser Tyr Val Cys Lys Gln Gly Phe Thr Asp Arg Gly Trp Gly Asn Gly
1               5                   10                  15

Cys Gly Leu Phe Gly Lys Gly Ser Ile Asp Thr Cys Ala Lys Phe Ser
            20                  25                  30

<210> SEQ ID NO 210
<211> LENGTH: 32
<212> TYPE: PRT
<213> ORGANISM: Flavivirus JEV SA14-14-2

<400> SEQUENCE: 210

Ser Tyr Val Cys Lys Gln Gly Phe Thr Asp Arg Gly Trp Gly Asn Gly
1               5                   10                  15

Cys Gly Phe Phe Gly Lys Gly Ser Ile Asp Thr Cys Ala Lys Phe Ser
            20                  25                  30

<210> SEQ ID NO 211
<211> LENGTH: 32
<212> TYPE: PRT
<213> ORGANISM: Flavivirus SLEV

<400> SEQUENCE: 211

Thr Phe Val Cys Lys Arg Asp Val Val Asp Arg Gly Trp Gly Asn Gly
1               5                   10                  15

Cys Gly Leu Phe Gly Lys Gly Ser Ile Asp Thr Cys Ala Lys Phe Thr
            20                  25                  30

<210> SEQ ID NO 212
<211> LENGTH: 32
<212> TYPE: PRT
<213> ORGANISM: Flavivirus YFV Asibi

<400> SEQUENCE: 212

Asp Asn Ala Cys Lys Arg Thr Tyr Ser Asp Arg Gly Trp Gly Asn Gly
1               5                   10                  15

Cys Gly Leu Phe Gly Lys Gly Ser Ile Val Ala Cys Ala Lys Phe Thr
            20                  25                  30

<210> SEQ ID NO 213
<211> LENGTH: 32
<212> TYPE: PRT
<213> ORGANISM: Flavivirus YFV 17d

<400> SEQUENCE: 213

Asp Asn Ala Cys Lys Arg Thr Tyr Ser Asp Arg Gly Trp Gly Asn Gly
1               5                   10                  15

Cys Gly Leu Phe Gly Lys Gly Ser Ile Val Ala Cys Ala Lys Phe Thr
            20                  25                  30

<210> SEQ ID NO 214
<211> LENGTH: 32
<212> TYPE: PRT
<213> ORGANISM: Flavivirus LGTV

<400> SEQUENCE: 214

Gly Thr Val Cys Lys Arg Asp Gln Ser Asp Arg Gly Trp Gly Asn His
1               5                   10                  15

Cys Gly Leu Phe Gly Lys Gly Ser Ile Val Thr Cys Val Lys Phe Thr
            20                  25                  30

<210> SEQ ID NO 215
<211> LENGTH: 32
<212> TYPE: PRT
<213> ORGANISM: Flavivirus TBEV

<400> SEQUENCE: 215

Gly Thr Val Cys Lys Arg Asp Gln Ser Asp Arg Gly Trp Gly Asn His
1               5                   10                  15

Cys Gly Leu Phe Gly Lys Gly Ser Ile Val Ala Cys Val Lys Ala Ala
            20                  25                  30

<210> SEQ ID NO 216
<211> LENGTH: 21
<212> TYPE: PRT
<213> ORGANISM: Flavivirus DENV-2

<400> SEQUENCE: 216

Phe Lys Val Val Lys Glu Ile Ala Glu Thr Gln His Gly Thr Ile Val
1               5                   10                  15

Ile Arg Val Gln Tyr
            20

<210> SEQ ID NO 217
<211> LENGTH: 21
<212> TYPE: PRT
<213> ORGANISM: Flavivirus DENV-2

```
<400> SEQUENCE: 217

Phe Lys Val Val Lys Glu Ile Ala Glu Thr Gln Gln Gly Thr Ile Val
1               5                   10                  15

Ile Arg Val Gln Tyr
            20

<210> SEQ ID NO 218
<211> LENGTH: 21
<212> TYPE: PRT
<213> ORGANISM: Flavivirus DENV-1

<400> SEQUENCE: 218

Phe Lys Leu Glu Lys Glu Val Ala Glu Thr Gln His Gly Thr Val Leu
1               5                   10                  15

Val Gln Val Lys Tyr
            20

<210> SEQ ID NO 219
<211> LENGTH: 21
<212> TYPE: PRT
<213> ORGANISM: Flavivirus DENV-3

<400> SEQUENCE: 219

Phe Val Leu Lys Lys Glu Val Ser Glu Thr Gln His Gly Thr Ile Leu
1               5                   10                  15

Ile Lys Val Glu Tyr
            20

<210> SEQ ID NO 220
<211> LENGTH: 21
<212> TYPE: PRT
<213> ORGANISM: Flavivirus DENV-4

<400> SEQUENCE: 220

Phe Ser Ile Asp Lys Glu Met Ala Glu Thr Gln His Gly Thr Thr Val
1               5                   10                  15

Val Lys Val Lys Tyr
            20

<210> SEQ ID NO 221
<211> LENGTH: 21
<212> TYPE: PRT
<213> ORGANISM: Flavivirus WNV

<400> SEQUENCE: 221

Phe Lys Phe Leu Gly Thr Pro Ala Asp Thr Gly His Gly Thr Val Val
1               5                   10                  15

Leu Glu Leu Gln Tyr
            20

<210> SEQ ID NO 222
<211> LENGTH: 21
<212> TYPE: PRT
<213> ORGANISM: Flavivirus JEV

<400> SEQUENCE: 222

Phe Ser Phe Ala Lys Asn Pro Ala Asp Thr Gly His Gly Thr Val Val
1               5                   10                  15

Ile Glu Leu Thr Tyr
            20
```

-continued

<210> SEQ ID NO 223
<211> LENGTH: 21
<212> TYPE: PRT
<213> ORGANISM: Flavivirus JEV SA14-14-2

<400> SEQUENCE: 223

Phe Ser Phe Ala Lys Asn Pro Ala Asp Thr Gly His Gly Thr Val Val
1               5                   10                  15

Ile Glu Leu Thr Tyr
            20

<210> SEQ ID NO 224
<211> LENGTH: 21
<212> TYPE: PRT
<213> ORGANISM: Flavivirus SLEV

<400> SEQUENCE: 224

Phe Thr Phe Ser Lys Asn Pro Thr Asp Thr Gly His Gly Thr Val Ile
1               5                   10                  15

Val Glu Leu Gln Tyr
            20

<210> SEQ ID NO 225
<211> LENGTH: 21
<212> TYPE: PRT
<213> ORGANISM: Flavivirus YFV Asibi

<400> SEQUENCE: 225

Met Phe Phe Val Lys Asn Pro Asp Thr Thr Gly His Gly Thr Val Val
1               5                   10                  15

Met Gln Val Lys Val
            20

<210> SEQ ID NO 226
<211> LENGTH: 21
<212> TYPE: PRT
<213> ORGANISM: Flavivirus YFV 17d

<400> SEQUENCE: 226

Met Phe Phe Val Lys Asn Pro Asp Thr Thr Gly His Gly Thr Val Val
1               5                   10                  15

Met Gln Val Lys Val
            20

<210> SEQ ID NO 227
<211> LENGTH: 21
<212> TYPE: PRT
<213> ORGANISM: Flavivirus LGTV

<400> SEQUENCE: 227

Phe Thr Trp Lys Arg Ala Pro Thr Asp Ser Gly His Asp Thr Val Val
1               5                   10                  15

Met Glu Val Gly Phe
            20

<210> SEQ ID NO 228
<211> LENGTH: 21
<212> TYPE: PRT
<213> ORGANISM: Flavivirus TBEV

<400> SEQUENCE: 228

Phe Thr Trp Lys Arg Ala Pro Thr Asp Ser Gly His Asp Thr Val Val

```
                1               5              10              15
Met Glu Val Thr Phe
                        20
```

MONOCLONAL ANTIBODIES THAT BIND OR NEUTRALIZE DENGUE VIRUS

RELATED APPLICATIONS

This application is a U.S. National Phase of International Application No. PCT/US2004/040674, filed Dec. 3, 2004, designating the U.S. and published in English on Jun. 23, 2005 as WO 2005/056600, which claims the benefit of U.S. Provisional Application No. 60/624,261, filed Nov. 1, 2004; U.S. Provisional Application No. 60/574,492, filed May 26, 2004; U.S. Provisional Application No. 60/552,528, filed Mar. 12, 2004; U.S. Provisional application No. 60/541,676, filed Feb. 4, 2004; and U.S. Provisional Application No. 60/528,161, filed Dec. 8, 2003, all of which are hereby expressly incorporated by reference in their entireties.

FIELD OF THE INVENTION

This invention relates generally to the field of immunology and specifically to monoclonal antibodies that bind or neutralize dengue virus.

BACKGROUND OF THE INVENTION

Among the arthropod-borne flaviviruses, the four dengue virus serotypes, dengue type 1 virus (DENV-1), dengue type 2 virus (DENV-2), dengue type 3 virus (DENV-3), and dengue type 4 virus (DENV-4), which constitute a serologically distinct subgroup are most important in terms of human morbidity and geographic distribution. Dengue viruses cause dengue outbreaks and major epidemics in most tropical and subtropical areas where *Aedes albopictus* and *Aedes aegypti* mosquitos are abundant. Dengue infection produces fever, rash, and joint pain in humans. A more severe and life-threatening form of dengue, characterized by hemorrhagic fever and hemorrhagic shock, has occurred with increasing frequency in Southeast Asia and Central and South America, where all four dengue virus serotypes circulate. The underlying cause of severe dengue remains controversial (Halstead, S. 1982 *Progress in Allergy.* 31:301-364; Rosen, L 1986 *Am. J. Trop. Med. Hyg.* 35:642-653). An association of severe dengue with increased viral replication has been reported recently (Wang, W. K. et al. 2002 *J. Virol.* 76:4662-4665). A safe and effective vaccine against dengue is currently not available.

The dengue virus contains a positive strand RNA genome, coding for a polyprotein that is cleaved co- and post-translationally by a combination of cellular and viral proteases to generate the individual viral proteins (Markoff, L. 1989 *J. Virol.* 63:3345-3352; Chambers, T. J. et al. 1990. *Ann. Rev. Microbiol.* 44:649-688; Falgout, B. et al. 1991 *J. Virol.* 65:2467-2475). Dengue virus prM and E structural proteins and nonstructural NS1 protein are glycosylated. The prM glycoprotein is further cleaved by the cellular enzyme furin following viral assembly, generating M, which is present in the mature virus (Stadler, K. et al. 1997 *J. Virol.* 71:8475-8481). Flavivirus prM and E form heterodimers, which are assembled into viral particles during infection (Wengler, G. and G. Wengler 1989 *J. Virol.* 63:2521-2526). In this manner, the prM serves to protect the functional integrity of E from acid-induced conformational change (Heinz, F. X. et al. 1994 *Virology* 198:109-117; Holzmann, H. et al. 1995 *Arch. Virol.* 140:213-221). The E glycoprotein is responsible for cell attachment, possibly mediated by a receptor, and for fusion with the cell membranes following viral entry.

Mouse monoclonal antibodies against the dengue viruses have been valuable for dengue virus serotype determination (Gentry, M. K. et al. 1982 *Am. J. Trop. Med. Hyg.* 31:548-555; Henchal, E. A. et al. 1982 *Am. J. Trop. Med. Hyg.* 31:830-836). Studies in which monoclonal antibodies were used against dengue virus and other flaviviruses have also provided valuable information concerning the antigenic structure of the major viral antigen E (Heinz, F. X. et al 1983 *Virology* 126:525-537; Henchal, E. A. et al. 1985 *Am. J. Trop. Med. Hyg.* 34:162-169; Heinz, F. X. 1986 *Adv. Virus Res.* 31:103-168; Mandl, C. W. et al. 1989 *J. Virol.* 63:564-571; Roehrig, J. T. et al. 1998 *Virology* 246:317-328). The three-dimensional structure of the E glycoprotein has been determined at 2 Å resolution for tick-borne encephalitis virus and recently for dengue type 2 virus (Rey, P. A. et al. 1995 *Nature* 375: 291-298; Modis, Y. et al. 2003 *Proc. Natl. Acad. Sci. USA* 100:6986-6991). These studies showed that the monomeric E polypeptide is folded into three distinct domains and that the E glycoprotein consists of a flat, elongated dimer structure with an interdomain ligand-binding pocket.

Monoclonal antibodies reactive to flavivirus envelope proteins have been shown to mediate protection against homologous virus challenge in animal models (Mathews, J. H. and J. T. Roehrig 1984 *J. Immunol.* 132:1533-1537; Brandriss, M. W. et al. 1986 *J. Gen. Virol.* 67:229-234; Gould, E. A. et al. 1986 *J. Gen. Virol.* 67:591-595; Kaufman, B. M. et al. 1987 *Am. J. Trop. Med. Hyg.* 36:427-434; Kimura-Kuroda, J., and K. Yasui 1988 *J. Virol.* 141:3606-3610). In most cases, protection by passive immunization has been correlated with the ability of these antibodies to neutralize the virus in vitro. Protection against dengue virus challenge was also demonstrated in mice following passive immunization with monoclonal or polyclonal antibodies specific to prM (Bray, M., and C. J. Lai. 1991 *Virology* 185:505-508; Kaufman, B M et al. 1987 *Am. J. Trop. Med. Hyg.* 36:427-434) or NS1 (Falgout, B. et al. 1990. *J. Virol.* 64:4356-4363; Henchal, E. A. et al. 1988 *J. Gen. Virol.* 69:2101-2107).

Most research efforts directed to the development of an attenuated live dengue vaccine have not yielded a satisfactory result. Recently, clinical evaluation was conducted on a genetically engineered DENV-4 mutant containing a 30-nucleotide deletion in the 3' non-coding region that exhibited reduced replicative capacity in simian cell culture and in primates (Durbin, A. P. et al. 2001 *Am. J. Trop. Med. Hyg.* 65:405-413; Men R., et al. 1996 *J. Virol.* 70:3930-3937). Following a single-dose inoculation, a total of 20 volunteers remained afebrile and exhibited very few clinical signs. Each of the vaccinees developed a high titer of DENV-4 neutralizing antibodies four to six weeks after immunization. However, five vaccinees showed an elevation of serum levels of the liver enzyme alanine transaminase (ALT). The ALT elevations were mostly transient and eventually subsided, but there remains a concern about the safety of a live dengue virus vaccine. Passive immunization with clinically acceptable dengue virus neutralizing antibodies provides an attractive alternative to prevention of dengue virus infection. Highly efficient neutralizing antibodies might also be useful for consideration as a possible therapy for severe dengue virus infection. Recently, a phage display of combinatorial antibody libraries has allowed for the isolation of antibodies against important viral pathogens from human or non-human primates (Persson, M. A. et al. 1991 *Proc. Natl. Acad. Sci.* 88:2432-2436; Williamson, R. A. et al. 1993 *Proc. Nat. Acad. Sci.* 90:41413-4145 [Erratum 91:1193, 1994]; Burton, D. R. et al. 1994 *Science* 266:1024-1027; Crowe, J. E. Jr. et al.

1994. Proc. Natl. Acad. Sci. 91:1386-1390; Maruyama, T. et al. 1999 J. Virol. 73:6024-6030; Schofield, D. J. et al. 2000 J. Virol. 74:5548-5555).

SEGUE TO THE INVENTION

In the current study, we employed this technique to identify a panel of chimpanzee Fab antibodies against DENV-4. One of these Fab antibodies neutralized DENV-4 efficiently by an in vitro assay and was combined with human sequences to convert it to the whole immunoglobulin G1 (IgG1) antibody. The humanized chimpanzee IgG1 antibody produced in CHO cells neutralized DENV-4 efficiently.

SUMMARY OF THE INVENTION

The present invention relates to monoclonal antibodies that bind or neutralize dengue type 1, 2, 3, and/or 4 virus. The invention provides such antibodies, fragments of such antibodies retaining dengue virus-binding ability, fully human or humanized antibodies retaining dengue virus-binding ability, and pharmaceutical compositions including such antibodies. The invention further provides for isolated nucleic acids encoding the antibodies of the invention and host cells transformed therewith. Additionally, the invention provides for prophylactic, therapeutic, and diagnostic methods employing the antibodies and nucleic acids of the invention.

BRIEF DESCRIPTION OF THE DRAWINGS

FIG. 2. Alignment of amino acid sequences among DENV-4-specific and cross-reactive Fab monoclonal antibodies. The amino acid sequences of the six chimpanzee Fab monoclonal antibodies recovered by repertoire cloning were compared. (A) Sequences of $V_L$ light chain segments (5A7-SEQ ID NO: 25; 3C1-SEQ ID NO: 41; 3E4-SEQ ID NO: 57; 7G4-SEQ ID NO: 73; 5H2-SEQ ID NO: 9; 5D9-SEQ ID NO: 89). (B) $V_H$ heavy chain segments (5A7-SEQ ID NO: 17; 3C1-SEQ ID NO: 33; 3E4-SEQ ID NO: 49; 7G4-SEQ ID NO: 65; 5H2-SEQ ID NO: 1; 5D9-SEQ ID NO: 81). The framework regions (FR1 to FR4) and complementarity determining regions (CDR1 to CDR3) are shown. A dash symbol indicates where an amino acid deletion occurred, and an identical amino acid is represented by a comma.

FIG. 6. Amino acid sequences of Fabs. (A) sequences of the $V_L$ κ light chain segments (2H7-SEQ ID NO: 121; 2H5-SEQ ID NO: 137; 3A2-SEQ ID NO: 153; 1A5-SEQ ID NO: 105; 1B2-SEQ ID NO: 169; 1A10-SEQ ID NO: 185; 3E4-SEQ ID NO: 57); (B) sequences of the VH γ1 heavy chain segments (2H7-SEQ ID NO: 113; 2H5-SEQ ID NO: 129; 3A2-SEQ ID NO: 145; 1A5-SEQ ID NO: 97; 1B2-SEQ ID NO: 161; 1A10-SEQ ID NO: 177; 3E4-SEQ ID NO: 49). FR, framework region; CDR, complementarity-determining region. The dash symbol represents an amino acid deletion and an identical amino acid is indicated by a dot. The sequence of Fab 3E4 was included for comparison with that of Fab 1A10.

FIG. 10. In vitro neutralization of dengue viruses and other flaviviruses by humanized IgG1 1A5. The neutralizing activity of IgG1 1A5 against DENV-1, Hawaii strain; DENV-2, New Guinea B strain; DENV-3, H87 strain; DENV-4, strain 814669; JEV, vaccine strain SA14-14-2; LGTV, strain TP 21; WNV/DENV-4 chimera was analyzed by PRNT.

FIG. 11. Neutralization of DENV-2 parental viruses and their variants using Fab 1A5. (A) NGB-P, DENV-2 NGB parent; DENV-2 variant NGB-V1; DENV2 variant NGB-V2. (B) NGC-P, DENV-2 NGC parent; DENV-2 variant NGC-V2. PRNT was performed using approximately 50 pfu of each virus for incubation with serially diluted Fab 1A5 at 37° C. for 1 h. The reaction mixture was used to infect Vero cells. Foci of infected cells were detected by immuno-staining.

FIG. 12. Alignment of amino acid sequences among flaviviruses. (A) shows the sequences surrounding $Val_{106}$ found in DENV-2 variants NGB-V2 and NGC-V2. The fusion sequence (loop) between c and d β-strands is underlined (DENV-2P-SEQ ID NO: 203; DENV-2V2-SEQ ID NO: 204; DENV-1-SEQ ID NO: 205; DENV-3-SEQ ID NO: 206; DENV-4-SEQ ID NO: 207; WNV-SEQ ID NO: 208; JEV-SEQ ID NO: 209; JEV SA14-14-2-SEQ ID NO: 210; SLEV-SEQ ID NO: 211; YFV Asibi-SEQ ID NO: 212; YFV 17D-SEQ ID NO: 213; LGTV-SEQ ID NO: 214; TBEV-SEQ ID NO: 215). (B) shows the sequences surrounding $Gln_{317}$ present in DENV-2 variant NGB-V1. The sequence between A and B β-strands is underlined (DENV-2P-SEQ ID NO: 216; DENV-2V1-SEQ ID NO: 217; DENV-1-SEQ ID NO: 218; DENV-3-SEQ ID NO: 219; DENV-4-SEQ ID NO: 220; WNV-SEQ ID NO: 221; JEV-SEQ ID NO: 222; JEV SA14-14-2-SEQ ID NO: 223; SLEV-SEQ ID NO: 224; YFV Asibi-SEQ ID NO: 225; YFV 17D-SEQ ID NO: 226; LGTV-SEQ ID NO: 227; TBEV-SEQ ID NO: 228). The references of the flavivirus sequences are as follows: DENV-1 (Mason, P. W. et al. 1987 *Virology* 161:262-267); DENV-2 (Hahn, Y. S. et al. 1988 *Virology* 162:167-180); DENV-3 (Osatomi, K. and H. Sumiyoshi. 1990 *Virology* 176:643-647); DENV-4 (Zhao, B. et al. 1986 *Virology* 155:77-88); WNV (Lanciotti, R. S. et al. 1999 *Science.* 286:2333-2337; Wengler, G. et al. 1985 *Virology* 147:264-274); St. Louis encephalitis virus (SLEV) (Trent, D. et al. 1987 *Virology* 156:293-304); JEV JaOAr S982 (Sumiyoshi, H. et al. 1987 *Virology* 161:497-510); JEV SA14-14-2 (Nitayaphan, S. et al. 1990 *Virology* 177:541-552); YFV 17D (Rice, C. M. et al. 1985 *Science* 229:726-733); YFV Asibi (Hahn, C. S. et al. 1987 *Proc. Nati. Acad. Sci. USA* 84:2019-2023); Langat virus (LGTV) (Mandl, C. W. et al. 1991 *Virology* 185:891-895); TBEV (Mandl, C. W. et al. 1988 *Virology* 166:197-205).

FIG. 13. Localization of Fab 1A5 epitope determinants in 3-D structure of DENV-2 E. (A) shows positions of $Gly_{106}$ and $His_{317}$ as viewed from the top of the dimeric E structure with domain I, domain II and domain III using the published coordinates (Modis, Y. et al. 2003 *Proc. Natl. Acad. Sci. USA* 100:6986-6991). (B) shows the expanded area of the insert above.

FIG. 14. Reactivity of Fab 1A5 to DENV-2 NGB parent and its antigenic variants. Panel A (top) shows binding of control Mab 3H5 (which does not bind to the fusion peptide) to various viruses by Western blot analysis as control. Gel lanes; 1, DENV-2, NGB parent; 2, DENV-2 NGB-V1; 3, DENV-2 NGB-V2; 4, NGB-parent/DENV-4 chimera; 5, NGB V1/DENV-4 chimera; 6, NGB-V2/DENV-4 chimera. Panel A (bottom) shows binding of Fab 1A5 to the viruses listed above by Western blot analysis. Boiled dengue virus samples in the absence of β-mercaptoethanol were separated on SDS-polyacrylamide gels by electrophoresis for Western blot analysis. Note that the electrophoretic mobility of the DENV-2 E bands that reacted with Mab 3H5 and with Fab 1A5 varied on the gel blot, presumably reflecting the E protein species glycosylated differently. Panel B shows binding of Fab 1A5 to the DENV-2 NGB parent and its antigenic variants by ELISA.

FIG. 16. Growth analysis of antigenic variants, chimeras, and the DENV-2 NGB parent in cultured cells. The DENV-2 NGB parent and its antigenic variants were analyzed for growth in C6/36 cells (A) and in Vero cells (B). Chimeras that contained C-prM-E of the parental NGB, variant NGB V-1 or NGB V-2 on the DENV-4 background were similarly analyzed for growth in C6/36 cells (C) and in Vero cells (D). Cells were infected each virus at 0.01 moi and the culture medium was collected daily for titer determination by focus assay on Vero cells.

FIG. 18. Binding activity of Fab 1A5 to DENV-4 parent and DENV-4 mutants containing a substitution of $Gly_{106}Val$ or $Leu_{107}Phe$ in the fusion loop (panel A) and neutralizing activity of Fab 1A5 against these viruses (panel B). The binding activity of Fab 1A5 to the DENV-4 parent and its derived mutants was determined by ELISA. PRNT was performed to determine the neutralizing activity.

Figure 1A:
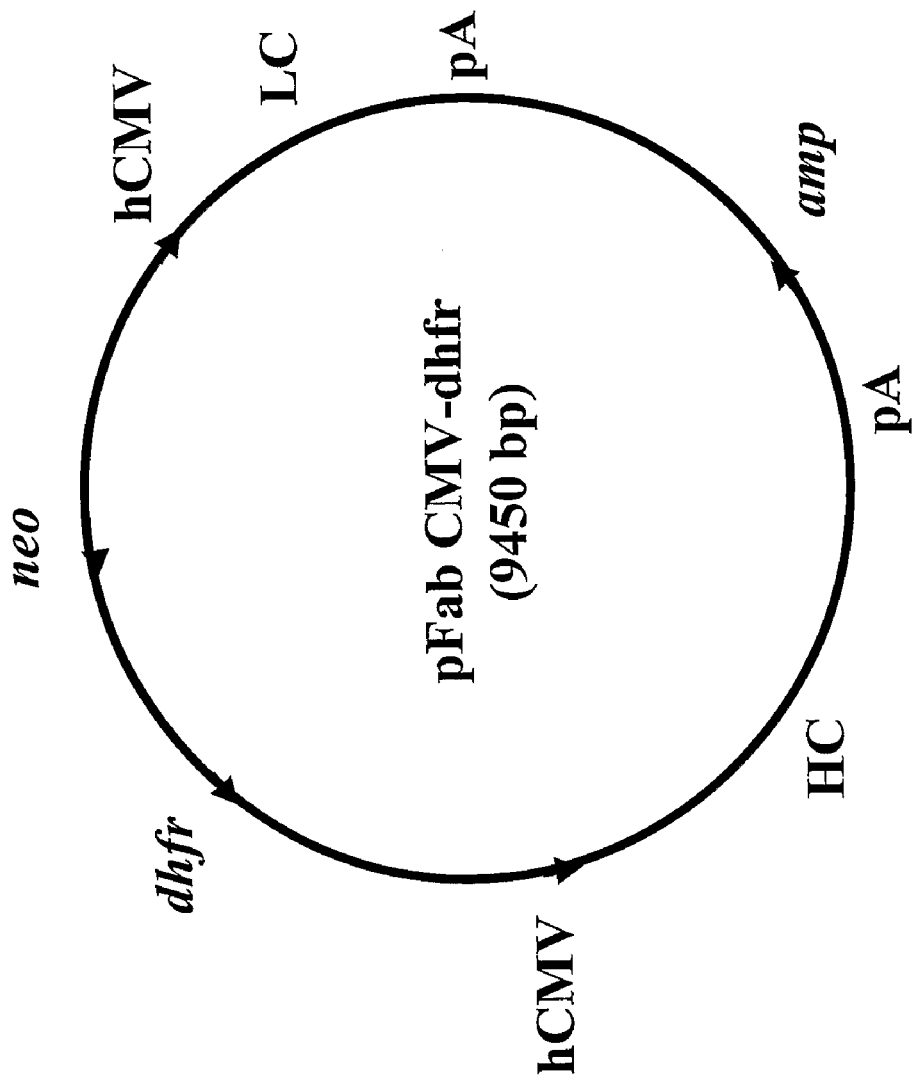
FIG. 1. A map of pFab CMV-dhfr vector for expression of full-length IgG1 in CHO cells and structure of the IgG1 light chain and heavy chain DNA inserts. (A) Locations of the various genes present in the expression vector. LC, light chain DNA; pA, polyA addition signal; HC, heavy chain DNA. The arrows indicate transcription direction. (B) Structure of the humanized IgG1 light chain and heavy chain genes under the control of an hCMV early promoter. $V_L$ and $C_L$ are the light chain hypervariable region and constant region, respectively. $V_H$, heavy chain hypervariable region; $C_H1$, constant region 1; hg, hinge; int-1, intron 1 (118 nucleotides); $C_H2$, constant region 2; int-2, intron 2 (97 nucleotides); $C_H3$, constant region 3. The dark-shaded regions are human IgG1 sequences and the medium-shaded regions represent chimpanzee IgG1 sequences. The selectable neo and dhfr genes (light-shaded) are flanked by a β-globin promoter (β-glo) and a poly (A) addition site (pA).

PART 1
Brief Description of the SEQ ID NOs.

| Region | Heavy Chain 5H2 Sequence SEQ ID NO: 1 | Light Chain 5H2 Sequence SEQ. ID. NO: 9 | Heavy Chain 5A7 Sequence SEQ. ID. NO: 17 | Light Chain 5A7 Sequence SEQ. ID. NO: 25 | Heavy Chain 3C1 Sequence SEQ. ID. NO: 33 | Light Chain 3C1 Sequence SEQ. ID. NO: 41 | Heavy Chain 3E4 Sequence SEQ. ID. NO: 49 | Light Chain 3E4 Sequence SEQ. ID. NO: 57 | Heavy Chain 7G4 Sequence SEQ. ID. NO: 65 | Light Chain 7G4 Sequence SEQ. ID. NO: 73 | Heavy Chain 5D9 Sequence SEQ. ID. NO: 81 | Light Chain 5D9 Sequence SEQ. ID. NO: 89 |
|---|---|---|---|---|---|---|---|---|---|---|---|---|
| FR1 | SEQ ID NO: 2 | SEQ ID NO: 10 | SEQ ID NO: 18 | SEQ ID NO: 26 | SEQ ID NO: 34 | SEQ ID NO: 42 | SEQ ID NO: 50 | SEQ ID NO: 58 | SEQ ID NO: 66 | SEQ ID NO: 74 | SEQ ID NO: 82 | SEQ ID NO: 90 |

-continued

PART 1
Brief Description of the SEQ ID NOs.

| Region | Heavy Chain 5H2 Sequence SEQ ID NO: 1 | Light Chain 5H2 Sequence SEQ. ID. NO: 9 | Heavy Chain 5A7 Sequence SEQ. ID. NO: 17 | Light Chain 5A7 Sequence SEQ. ID. NO: 25 | Heavy Chain 3C1 Sequence SEQ. ID. NO: 33 | Light Chain 3C1 Sequence SEQ. ID. NO: 41 | Heavy Chain 3E4 Sequence SEQ. ID. NO: 49 | Light Chain 3E4 Sequence SEQ. ID. NO: 57 | Heavy Chain 7G4 Sequence SEQ. ID. NO: 65 | Light Chain 7G4 Sequence SEQ. ID. NO: 73 | Heavy Chain 5D9 Sequence SEQ. ID. NO: 81 | Light Chain 5D9 Sequence SEQ. ID. NO: 89 |
|---|---|---|---|---|---|---|---|---|---|---|---|---|
| CDR1 | SEQ ID NO: 3 | SEQ ID NO: 11 | SEQ ID NO: 19 | SEQ ID NO: 27 | SEQ ID NO: 35 | SEQ ID NO: 43 | SEQ ID NO: 51 | SEQ ID NO: 59 | SEQ ID NO: 67 | SEQ ID NO: 75 | SEQ ID NO: 83 | SEQ ID NO: 91 |
| FR2 | SEQ ID NO: 4 | SEQ ID NO: 12 | SEQ ID NO: 20 | SEQ ID NO: 28 | SEQ ID NO: 36 | SEQ ID NO: 44 | SEQ ID NO: 52 | SEQ ID NO: 60 | SEQ ID NO: 68 | SEQ ID NO: 76 | SEQ ID NO: 84 | SEQ ID NO: 92 |
| CDR2 | SEQ ID NO: 5 | SEQ ID NO: 13 | SEQ ID NO: 21 | SEQ ID NO: 29 | SEQ ID NO: 37 | SEQ ID NO: 45 | SEQ ID NO: 53 | SEQ ID NO: 61 | SEQ ID NO: 69 | SEQ ID NO: 77 | SEQ ID NO: 85 | SEQ ID NO: 93 |
| FR3 | SEQ ID NO: 6 | SEQ ID NO: 14 | SEQ ID NO: 22 | SEQ ID NO: 30 | SEQ ID NO: 38 | SEQ ID NO: 46 | SEQ ID NO: 54 | SEQ ID NO: 62 | SEQ ID NO: 70 | SEQ ID NO: 78 | SEQ ID NO: 86 | SEQ ID NO: 94 |
| CDR3 | SEQ ID NO: 7 | SEQ ID NO: 15 | SEQ ID NO: 23 | SEQ ID NO: 31 | SEQ ID NO: 39 | SEQ ID NO: 47 | SEQ ID NO: 55 | SEQ ID NO: 63 | SEQ ID NO: 71 | SEQ ID NO: 79 | SEQ ID NO: 87 | SEQ ID NO: 95 |
| FR4 | SEQ ID NO: 8 | SEQ ID NO: 16 | SEQ ID NO: 24 | SEQ ID NO: 32 | SEQ ID NO: 40 | SEQ ID NO: 48 | SEQ ID NO: 56 | SEQ ID NO: 64 | SEQ ID NO: 72 | SEQ ID NO: 80 | SEQ ID NO: 88 | SEQ ID NO: 96 |

Deposit of Biological Material

The following biological material has been deposited in accordance with the terms of the Budapest Treaty with the American Type Culture Collection (ATCC), Manassas, Va., on the date indicated:

| Biological material | Designation No. | Date |
|---|---|---|
| Plasmid: Humanized IgG1 5H2 | PTA-5662 | Nov. 26, 2003 |

The Plasmid: Humanized IgG1 5H2 was deposited as ATCC Accession No. PTA-5662 on Nov. 26, 2003 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited biological material is not to be construed as a license to practice the invention in contravention of the rights granted under the authority of any government in accordance with its patent laws.

DETAILED DESCRIPTION OF THE PREFERRED EMBODIMENT

A safe and effective dengue vaccine is still not available. Passive immunization using monoclonal antibodies from humans or non-human primates represents an attractive alternative for prevention of dengue virus infection. Fab monoclonal antibodies to dengue type 4 virus (DENV-4) were recovered by repertoire cloning of bone marrow mRNAs from an immune chimpanzee and analyzed for antigen binding specificity, $V_H$ and $V_L$ sequences, and neutralizing activity against DENV-4 in vitro. Fabs 5A7, 3C1, 3E4 and 7G4 were isolated from a library constructed from a chimpanzee following intrahepatic transfection with infectious DENV-4 RNA. Fabs 5H2 and 5D9, which had nearly identical $V_H$ sequences, but varied in their $V_L$ sequences, were recovered from a library constructed from the same chimpanzee after superinfection with a mixture of DENV-1, DENV-2 and DENV-3. In radioimmunoprecipitation, Fab 5A7 precipitated only DENV-4 prM, and Fabs 3E4, 7G4, 5D9 and 5H2 precipitated DENV-4 E but little or no prM. Fab 3E4 and Fab 7G4 competed with each other for binding to DENV-4 in and enzyme-linked immunosorbent assay (ELISA), as did Fab 3C1 and Fab 5A7. Fab 5H2 recognized an epitope on DENV-4 that was separate from the epitope(s) recognized by other Fabs. Both Fab 5H2 and Fab 5D9 neutralized DENV-4 efficiently with a titer of 0.24-0.58 µg/ml by plaque reduction neutralization test (PRNT), whereas DENV-4 neutralizing activity of other Fabs was low or not detected. Fab 5H2 was converted to full-length IgG1 by combining it with human sequences. The humanized chimpanzee antibody IgG1 5H2 produced in CHO cells neutralized DENV-4 strains from different geographical origins at a similar 50% plaque reduction ($PRNT_{50}$) titer of 0.03-0.05 µg/ml. The DENV-4 binding affinities were 0.42 nM for Fab 5H2 and 0.24 nM for full-length IgG1 5H2. Monoclonal antibody IgG1 5H2 is predicted to be invaluable for prophylactic and therapeutic application against dengue virus in humans.

Definitions

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and ill vivo. In particular, as used herein, the term "antibody" means not only full-length immunoglobulin molecules but also antigen binding active fragments such as the well-known active fragments $F(ab')_2$, Fab, Fv, and Fd.

As used herein, the term "dengue virus disease" means any disease caused, directly or indirectly, by one of the four serotypes of a dengue virus, which is a flavivirus. Dengue is an acute febrile disease characterized by sudden onset, with headache, fever, prostration, joint and muscle pain, lymphadenopathy, and a rash that appears simultaneously with a temperature rise. A second phase of temperature rise may appear following an afebrile period. Dengue hemorrhagic fever/dengue shock syndrome is an acute disease occurring primarily in children characterized by an abrupt febrile onset followed by hemorrhagic manifestations and circulatory collapse.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their host cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (1) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., B-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-DENV-4 Monoclonal Antibodies

The present invention derives, in part, from the isolation and characterization of a novel chimpanzee Fab fragment and its humanized monoclonal antibody that selectively binds and neutralizes dengue type 4 virus and that we have designated 5H2. As described more fully herein, this new monoclonal antibody has been shown to bind and neutralize the dengue type 4 virus. The paratope of the 5H2 Fab fragment associated with the neutralization epitope on the dengue type 4 virus is defined by the amino acid (aa) sequences of the immunoglobulin heavy and light chain V-regions depicted in FIG. 2 and SEQ ID NO: 1 and SEQ ID NO: 9. The nucleic acid sequences coding for these aa sequences were identified as described in Protocol 1, by sequencing the Fab heavy chain and light chain fragments. Due to the degeneracy of the DNA code, the paratope is more properly defined by the derived aa sequences depicted in FIG. 2 and SEQ ID NO: 1 and SEQ ID NO: 9.

The present invention derives, additionally in part, from the isolation and characterization of novel chimpanzee Fab monoclonal antibodies that selectively bind and precipitate dengue type 4 virus prM or E glycoproteins that we have designated 5A7, 3C1, 3E4, 7G4, 5H2, and 5D9. As described more fully herein, these new monoclonal antibodies have been shown to bind and precipitate the dengue type 4 virus prM or E glycoproteins. The paratopes of the 5A7, 3C1, 3E4, 7G4, 5H2, and 5D9 Fab fragments associated with the epitopes on the dengue type 4 virus are defined by the amino acid (aa) sequences of the immunoglobulin heavy and light chain V-regions depicted in FIG. 2 and, for 5A7, SEQ ID NO: 17 and SEQ ID NO: 25;

for 3C1, SEQ ID NO: 33 and SEQ ID NO: 41;

for 3E4, SEQ ID NO: 49 and SEQ ID NO: 57;

for 7G4, SEQ ID NO: 65 and SEQ ID NO: 73; and for 5D9, SEQ ID NO: 81 and SEQ ID NO: 89.

In one set of embodiments, the present invention provides the full-length, humanized monoclonal antibody of the 5H2 antibody, or the 5A7, 3C1, 3E4, 7G4, or 5D9 antibody or other dengue type 4 virus antibody in isolated form and in pharmaceutical preparations. Similarly, as described herein, the present invention provides isolated nucleic acids, host cells transformed with nucleic acids, and pharmaceutical preparations including isolated nucleic acids, encoding the full-length, humanized monoclonal antibody of the 5H2 antibody, or the 5A7, 3C1, 3E4, 7G4, or 5D9 antibody or other dengue type 4 virus antibody. Finally, the present invention provides methods, as described more fully herein, employing these antibodies and nucleic acids in the in vitro and in vivo diagnosis, prevention and therapy of dengue virus disease.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology,* 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of a full-length antibody. Similarly, an antibody from which the Fc region has been enzymatically cleaved, or which has been produced without the Fc region, designated an Fab fragment, retains one of the antigen binding sites of a full-length antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986, supra; Roitt, 1991, supra). In both the heavy chain Fd fragment and the light chain of IgG immunoglobulins, there are four framework regions (FRI through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding Fab portion of the 5H2 monoclonal antibody as well as the relevant FR and CDR regions are disclosed herein. SEQ ID NO: 1 discloses the amino acid sequence of the Fd fragment of 5H2. The amino acid sequences of the heavy chain FR1, CDR1, FR2, CDR2, FR3, CDR3 and FR4 regions are disclosed as SEQ ID NO: 2 through SEQ ID NO: 8, respectively. SEQ ID NO: 9 discloses the amino acid sequence of the light chain of 5H2. The amino acid sequences of the light chain FR1, CDR1, FR2, CDR2, FR3, CDR3 and FR4 regions are disclosed as SEQ ID NO: 10 through SEQ ID NO: 16, respectively.

The complete amino acid sequences of the antigen-binding Fab portion of the 5A7 monoclonal antibody as well as the relevant FR and CDR regions are disclosed herein. SEQ ID NO: 17 discloses the amino acid sequence of the Fd fragment of 5A7. The amino acid sequences of the heavy chain FR1, CDR1, FR2, CDR2, FR3, CDR3 and FR4 regions are disclosed as SEQ ID NO: 18 through SEQ ID NO: 24, respectively. SEQ ID NO: 25 discloses the amino acid sequence of the light chain of 5A7. The amino acid sequences of the light chain FR1, CDR1, FR2, CDR2, FR3, CDR3 and FR4 regions are disclosed as SEQ ID NO: 26 through SEQ ID NO: 32, respectively.

The complete amino acid sequences of the antigen-binding Fab portion of the 3C1 monoclonal antibody as well as the relevant FR and CDR regions are disclosed herein. SEQ ID NO: 33 discloses the amino acid sequence of the Fd fragment of 3C1. The amino acid sequences of the heavy chain FR1, CDR1, FR2, CDR2, FR3, CDR3 and FR4 regions are disclosed as SEQ ID NO: 34 through SEQ ID NO: 40, respectively. SEQ ID NO: 41 discloses the amino acid sequence of the light chain of 3C1. The amino acid sequences of the light chain FR1, CDR1, FR2, CDR2, FR3, CDR3 and FR4 regions are disclosed as SEQ ID NO: 42 through SEQ ID NO: 48, respectively.

The complete amino acid sequences of the antigen-binding Fab portion of the 3E4 monoclonal antibody as well as the relevant FR and CDR regions are disclosed herein. SEQ ID NO: 49 discloses the amino acid sequence of the Fd fragment of 3E4. The amino acid sequences of the heavy chain FR1, CDR1, FR2, CDR2, FR3, CDR3 and FR4 regions are disclosed as SEQ ID NO: 50 through SEQ ID NO: 56, respectively. SEQ ID NO: 57 discloses the amino acid sequence of the light chain of 3E4. The amino acid sequences of the light chain FR1, CDR1, FR2, CDR2, FR3, CDR3 and FR4 regions are disclosed as SEQ ID NO: 58 through SEQ ID NO: 64, respectively.

The complete amino acid sequences of the antigen-binding Fab portion of the 7G4 monoclonal antibody as well as the relevant FR and CDR regions are disclosed herein. SEQ ID NO: 65 discloses the amino acid sequence of the Fd fragment of 7G4. The amino acid sequences of the heavy chain FR1, CDR1, FR2, CDR2, FR3, CDR3 and FR4 regions are disclosed as SEQ ID NO: 66 through SEQ ID NO: 72, respectively. SEQ ID NO: 73 discloses the amino acid sequence of the light chain of 7G4. The amino acid sequences of the light chain FR1, CDR1, FR2, CDR2, FR3, CDR3 and FR4 regions are disclosed as SEQ ID NO: 74 through SEQ ID NO: 80, respectively.

The complete amino acid sequences of the antigen-binding Fab portion of the 5D9 monoclonal antibody as well as the relevant FR and CDR regions are disclosed herein. SEQ ID NO: 81 discloses the amino acid sequence of the Fd fragment of 5D9. The amino acid sequences of the heavy chain FR1, CDR1, FR2, CDR2, FR3, CDR3 and FR4 regions are disclosed as SEQ ID NO: 82 through SEQ ID NO: 88, respectively. SEQ ID NO: 89 discloses the amino acid sequence of the light chain of 5D9. The amino acid sequences of the light chain FR1, CDR1, FR2, CDR2, FR3, CDR3 and FR4 regions are disclosed as SEQ ID NO: 90 through SEQ ID NO: 96, respectively.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies.

Thus, as will be apparent to one of ordinary skill in the art, the present invention also provides for F(ab')$_2$, Fab, Fv and Fd fragments of the 5H2 antibody, or the 5A7, 3C1, 3E4, 7G4, or 5D9 antibody or other dengue type 4 virus antibody; chimeric antibodies in which the Fc and/or FR and/or CDR1 and/or CDR2 and/or light chain CDR3 regions of the 5H2 antibody, or the 5A7, 3C1, 3E4, 7G4, or 5D9 antibody or other dengue type 4 virus antibody, have been replaced by homologous human or non-human sequences; chimeric F(ab')$_2$ fragment antibodies in which the FR and/or CDR1 and/or CDR2 and/or light chain CDR3 regions of the 5H2 antibody, or the 5A7, 3C1, 3E4, 7G4, or 5D9 antibody or other dengue type 4 virus antibody, have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the 5H2 antibody, or the 5A7, 3C1, 3E4, 7G4, or 5D9 antibody or other dengue type 4 virus antibody, by the construction of CDR grafted or chimeric antibodies or antibody fragments containing all, or part thereof, of the disclosed heavy and light chain V-region CDR aa sequences (Jones, P. T. et al. 1986. *Nature* 321:522; Verhoeyen, M. et al. 1988 *Science* 39:1534; and Tempest, P. R. et al. 1991 *Bio/Technology* 9:266), without destroying the specificity of the antibodies for the dengue type 4 virus epitope. Such CDR grafted or chimeric antibodies or antibody fragments can be effective in prevention and treatment of dengue infection in animals (e.g. cattle) and man.

In preferred embodiments, the chimeric antibodies of the invention are fully human or humanized chimpanzee monoclonal antibodies including at least the heavy chain CDR3 region of the 5H2 antibody, or the 5A7, 3C1, 3E4, 7G4, or 5D9 antibody or other dengue type 4 virus antibody. As noted above, such chimeric antibodies may be produced in which some or all of the FR regions of the 5H2 antibody, or the 5A7, 3C1, 3E4, 7G4, or 5D9 antibody or other dengue type 4 virus antibody, have been replaced by other homologous human FR regions. In addition, the Fc portions may be replaced so as to produce IgA or IgM as well as IgG antibodies bearing some or all of the CDRs of the 5H2 antibody, or the 5A7, 3C1, 3E4, 7G4, or 5D9 antibody or other dengue type 4 virus antibody. Of particular importance is the inclusion of the heavy chain CDR3 region and, to a lesser extent, the other CDRs of the 5H2 antibody, or the 5A7, 3C1, 3E4, 7G4, or 5D9 antibody or other dengue type 4 virus antibody. Such fully human or humanized chimpanzee monoclonal antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the 5H2 antibody, or the 5A7, 3C1, 3E4, 7G4, or 5D9 antibody or other dengue type 4 virus antibody. Some of the CDRs may be replaced as well. Again, however, it is preferred that at least the heavy chain CDR3 of the 5H2 antibody, or the 5A7, 3C1, 3E4, 7G4, or 5D9 antibody or other dengue type 4 virus antibody, be included in such chimeric antibodies and, to a lesser extent, it is also preferred that some or all of the other CDRs of the 5H2 antibody, or the 5A7, 3C1, 3E4, 7G4, or 5D9 antibody or other dengue type 4 virus antibody, be included. Such chimeric antibodies bearing non-human immunoglobulin sequences admixed with the CDRs of the 5H2 antibody, or the 5A7, 3C1, 3E4, 7G4, or 5D9 antibody or other dengue type 4 virus antibody, are not preferred for use in humans and are particularly not preferred for extended use because they may evoke an immune response against the non-human sequences. They may, of course, be used for brief periods or in immunosuppressed individuals but, again, fully human or humanized chimpanzee monoclonal antibodies are preferred. Because such antibodies may be used for brief periods or in immunosuppressed subjects, chimeric antibodies bearing non-human mammalian Fc and FR sequences but including at least the heavy chain CDR3 of the 5H2 antibody, or the 5A7, 3C1, 3E4, 7G4, or 5D9 antibody or other dengue type 4 virus antibody, are contemplated as alternative embodiments of the present invention.

For inoculation or prophylactic uses, the antibodies of the present invention are preferably full-length antibody molecules including the Fc region. Such full-length antibodies will have longer half-lives than smaller fragment antibodies (e.g. Fab) and are more suitable for intravenous, intraperitoneal, intramuscular, intracavity, subcutaneous, or transdermal administration.

In some embodiments, Fab fragments, including chimeric Fab fragments, are preferred. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ s and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fabs, smaller antibody fragments and epitope-binding peptides having binding specificity for the epitope defined by the 5H2 antibody, or the 5A7, 3C1, 3E4, 7G4, or 5D9 antibody or other dengue type 4 virus antibody, are also contemplated by the present invention and can also be used to bind or neutralize the virus. For example, single chain antibodies can be constructed according to the method of U.S. Pat. No. 4,946,778, to Ladner et al. Single chain antibodies comprise the variable regions of the light and heavy chains joined by a flexible linker moiety. Yet smaller is the antibody fragment known as the single domain antibody or Fd, which comprises an isolated VH single domain. Techniques for obtaining a single domain antibody with at least some of the binding specificity of the full-length antibody from which they are derived are known in the art.

It is possible to determine, without undue experimentation, if an altered or chimeric antibody has the same specificity as the antibody of the 5H2 antibody, or the 5A7, 3C1, 3E4, 7G4, or 5D9 antibody or other dengue type 4 virus antibody, of the invention by ascertaining whether the former blocks the latter from binding to dengue type 4 virus. If the monoclonal antibody being tested competes with the 5H2 antibody, or the 5A7, 3C1, 3E4, 7G4, or 5D9 antibody or other dengue type 4 virus antibody, as shown by a decrease in binding of the 5H2 antibody, or the 5A7, 3C1, 3E4, 7G4, or 5D9 antibody or other dengue type 4 virus antibody, then it is likely that the two monoclonal antibodies bind to the same, or a closely spaced, epitope. Still another way to determine whether a monoclonal antibody has the specificity of the 5H2 antibody, or the 5A7, 3C1, 3E4, 7G4, or 5D9 antibody or other dengue type 4 virus antibody, of the invention is to pre-incubate the 5H2 antibody, or the 5A7, 3C1, 3E4, 7G4, or 5D9 antibody or other dengue type 4 virus antibody, with dengue type 4 virus with which it is normally reactive, and then add the monoclonal antibody being tested to determine if the monoclonal antibody being tested is inhibited in its ability to bind dengue type 4 virus. If the monoclonal antibody being tested is inhibited then, in all likelihood, it has the same, or a functionally equivalent, epitope and specificity as the 5H2 antibody, or the 5A7, 3C1, 3E4, 7G4, or 5D9 antibody or other dengue type 4 virus antibody, of the invention. Screening of monoclonal antibodies of the invention also can be carried out utilizing dengue type 4 virus and determining whether the monoclonal antibody neutralizes dengue type 4 virus.

By using the antibodies of the invention, it is now possible to produce anti-idiotypic antibodies which can be used to screen other monoclonal antibodies to identify whether the antibody has the same binding specificity as an antibody of the invention. In addition, such antiidiotypic antibodies can be used for active immunization (Herlyn, D. et al. 1986 *Science* 232:100). Such anti-idiotypic antibodies can be produced using well-known hybridoma techniques (Kohler, G. and Milstein, C. 1975 *Nature* 256:495). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody.

An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Nucleic Acids Encoding Anti-DENV-4 Antibodies

Given the disclosure herein of the amino acid sequences of the heavy chain Fd and light chain variable domains of the 5H2 antibody, or the 5A7, 3C1, 3E4, 7G4, or 5D9 antibody or other dengue type 4 virus antibody, one of ordinary skill in the art is now enabled to produce nucleic acids which encode this antibody or which encode the various fragment antibodies or chimeric antibodies described above. It is contemplated that such nucleic acids will be operably joined to other nucleic acids forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the 5H2 antibody, or the 5A7, 3C1, 3E4, 7G4, or 5D9 antibody or other dengue type 4 virus antibody, including framework and CDRs or parts thereof, and a suitable promoter either with (Whittle, N. et al. 1987 *Protein Eng.* 1:499 and Burton, D. R. et al. 1994 *Science* 266:1024) or without (Marasco, W. A. et al. 1993 *Proc. Natl. Acad. Sci.* (*USA*) 90:7889 and Duan, L. et al. 1994 *Proc. Natl. Acad, Sci.* (*USA*) 91:5075) a signal sequence for export or secretion. Such vectors may be transformed or transfected into prokaryotic (Huse, W. D. et al. 1989 *Science* 246:1275; Ward, S. et al. 1989 *Nature* 341:544; Marks, J. D. et al 1991 *J. Mol. Biol.* 222:581; and Barbas, C. F. et al. 1991 *Proc. Natl. Acad. Sci.* (*USA*) 88:7987) or eukaryotic (Whittle, N. et al. 1987 *Protein Eng.* 1:499 and Burton, D. R. et al. 1994 *Science* 266:1024) cells or used for gene therapy (Marasco, W. A. et al. 1993 *Proc. Natl. Acad, Sci.* (*USA*) 90:7889 and Duan, L. et al. 1994 *Proc. Natl. Acad, Sci.* (*USA*) 91:5075) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

A preferred vector for screening monoclonal antibodies, but not necessarily preferred for the mass production of the antibodies of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic, regulatory sequences. Such vectors can be constructed by those with skill in the art and have been described by Smith, G. P. et al. (1985 *Science* 228:1315); Clackson, T. et al. (1991 *Nature* 352:624); Kang et al. (1991 in "Methods: A Companion to Methods in Enzymology: Vol. 2"; R. A. Lerner and D. R. Burton, ed. Academic Press, NY, pp 111-118); Barbas, C. F. et al. (1991 *Proc, Natl. Acad. Sci.* (*USA*) 88:7978), Roberts, B. L. et al. (1992 *Proc. Natl. Acad. Sci.* (*USA*) 89:2429).

A fusion polypeptide may be useful for purification of the antibodies of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein to the membrane of the host cell, such as the periplasmic membrane of Gram-negative bacteria. A preferred secretion signal for *E. coli* is a pelB secretion signal. The leader sequence of the pelB protein has previously been used as a secretion signal for fusion proteins (Better, M. et al. 1988 *Science* 240:1041; Sastry, L. et al. 1989 *Proc, Natl. Acad. Sci* (*USA*) 86:5728; and Mullinax, R. L. et al., 1990 *Proc. Natl. Acad. Sci. USA* 87:8095). Amino acid residue sequences for other secretion signal polypeptide domains from *E. coli* useful in this invention can be found in Neidhard, F. C. (ed.), 1987 *Escherichia coli and Salmonella Typhimurium: Typhimurium Cellular and Molecular Biology*, American Society for Microbiology, Washington, D.C.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine et al. 1975 *Nature* 254:34). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColEI found in pBR322 and a variety of other common plasmids. Also preferred is the p15A origin of replication found on pACYC and its derivatives. The ColEI and p15A replicons have been extensively utilized in molecular biology, are available on a variety of plasmids and are described by Sambrook. et al. 1989 *Molecular Cloning: A Laboratory Manual,* 2nd edition, Cold Spring Harbor Laboratory Press.

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those commercially available from suppliers such as Invitrogen, (San Diego, Calif.).

When the antibodies of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the full-length antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a di-cistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies of the present invention may additionally, of course, be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

The antibodies of the present invention may furthermore, of course, be produced in plants. In 1989, Hiatt et al. 1989 *Nature* 342:76 first demonstrated that functional antibodies could be produced in transgenic plants. Since then, a considerable amount of effort has been invested in developing plants for antibody (or "plantibody") production (for reviews see Giddings, G. et al., 2000 *Nat Biotechnol* 18:1151; Fischer, R. and Emans, N., 2000, *Transgenic Res* 9:279). Recombinant antibodies can be targeted to seeds, tubers, or fruits, making administration of antibodies in such plant tissues advantageous for immunization programs in developing countries and worldwide.

In another embodiment, the present invention provides host cells, both prokaryotic and eukaryotic, transformed or transfected with, and therefore including, the vectors of the present invention.

Diagnostic and Pharmaceutical Anti-DENV-4 Antibody Preparations

The invention also relates to a method for preparing diagnostic or pharmaceutical compositions comprising the monoclonal antibodies of the invention or polynucleotide sequences encoding the antibodies of the invention or part thereof, the pharmaceutical compositions being used for immunoprophylaxis or immunotherapy of dengue virus disease. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

A preferred embodiment of the invention relates to monoclonal antibodies whose heavy chains comprise in CDR3 the polypeptide having SEQ ID NO: 7, and/or whose light chains comprise in CDR3 the polypeptide having SEQ ID NO: 15; whose heavy chains comprise in CDR3 the polypeptide having SEQ ID NO: 23, and/or whose light chains comprise in CDR3 the polypeptide having SEQ ID NO: 31; whose heavy chains comprise in CDR3 the polypeptide having SEQ ID NO: 39, and/or whose light chains comprise in CDR3 the polypeptide having SEQ ID NO: 47; whose heavy chains comprise in CDR3 the polypeptide having SEQ ID NO: 55, and/or whose light chains comprise in CDR3 the polypeptide having SEQ ID NO: 63; whose heavy chains comprise in CDR3 the polypeptide having SEQ ID NO: 71, and/or whose light chains comprise in CDR3 the polypeptide having SEQ ID NO: 79; whose heavy chains comprise in CDR3 the polypeptide having SEQ ID NO: 87, and/or whose light chains comprise in CDR3 the polypeptide having SEQ ID NO: 95; and conservative variations of these peptides. Also encompassed by the present invention are certain amino acid sequences that bind to epitopic sequences in prM or E of dengue type 4 virus and that confer neutralization of dengue type 4 virus when bound thereto. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also bind or neutralize dengue type 4 virus. Analogously, another preferred embodiment of the invention relates to polynucleotides which encode the above noted heavy chain polypeptides and to polynucleotide sequences which are complementary to these polynucleotide sequences. Complementary polynucleotide sequences include those sequences that hybridize to the polynucleotide sequences of the invention under stringent hybridization conditions.

The anti-dengue type 4 virus antibodies of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific antihapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of dengue type 4 virus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of the invention, dengue type 4 virus may be detected by the monoclonal antibodies of the invention when present in biological fluids and tissues. Any sample containing a detectable amount of dengue type 4 virus can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of DENV-4

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the dengue type 4 virus antigen for which the monoclonal antibodies are specific.

The concentration of detectably labeled monoclonal antibody which is administered should be sufficient such that the binding to dengue type 4 virus is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/kg to about 50 mg/kg, preferably 0.1 mg/kg to about 20 mg/kg, most preferably about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The monoclonal antibodies of the invention can be used in vitro and in vivo to monitor the course of dengue virus disease therapy. Thus, for example, by measuring the increase or decrease in the number of cells infected with dengue type 4 virus or changes in the concentration of dengue type 4 virus present in the body or in various body fluids, it would be possible to determine whether a particular therapeutic regimen aimed at ameliorating dengue virus disease is effective.

Prophylaxis and Therapy of Dengue Virus Disease

The monoclonal antibodies can also be used in prophylaxis and as therapy for dengue virus disease in humans. The terms, "prophylaxis" and "therapy" as used herein in conjunction with the monoclonal antibodies of the invention denote both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of dengue virus disease or administered to subjects already evidencing active dengue virus infection. In the present invention, Fab fragments also bind or neutralize dengue type 4 virus and therefore may be used to treat dengue virus infection but full-length antibody molecules are otherwise preferred.

As used herein, a "prophylactically effective amount" of the monoclonal antibodies of the invention is a dosage large enough to produce the desired effect in the protection of individuals against dengue virus infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, preferably from about 0.1 mg/kg to about 20 mg/kg, most preferably from about 0.2 mg/kg to about 2 mg/kg, in one or more administrations (priming and boosting).

As used herein, a "therapeutically effective amount" of the monoclonal antibodies of the invention is a dosage large enough to produce the desired effect in which the symptoms of dengue virus disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, preferably from about 0.1 mg/kg to about 20 mg/kg, most preferably from about 0.2 mg/kg to about 2 mg/kg, in one or more dose administrations daily, for one or several days. Preferred is administration of the antibody for 2 to 5 or more consecutive days in order to avoid "rebound" of virus replication from occurring.

The monoclonal antibodies of the invention can be administered by injection or by gradual infusion over time. The administration of the monoclonal antibodies of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, *Remington's Pharmaceutical Sciences*, 18th edition, 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and the like.

Monoclonal Antibodies That Bind or Neutralize Dengue Type 4 Virus

Two chimpanzees (#1616 and #1618) were intrahepatically transfected with the full-length RNA transcripts of cloned DENV-4 cDNA (Lai, C. J. et al. 1991 *Proc. Natl. Acad. Sci. USA*. 88:5139-5143). Four weeks after inoculation, these chimpanzees showed transient mild serum ALT elevations and became sero-positive for DENV-4, indicating that both animals were infected. At 9 weeks, the antibodies against DENV-4 reached a 50% plaque reduction ($PRNT_{50}$) titer of 1/992 and 1/1065, respectively. This level of neutralizing antibodies was comparable to that in rhesus monkeys infected with DENV-4 by a subcutaneous route (Men R., et al. 1996 *J. Virol.* 70:3930-3937). To increase the repertoire of dengue virus-specific antibodies, both chimpanzees were inoculated with a mixture of DENV-1, DENV-2 and DENV-3, each at 106 PFU/dose, 9.5 months after DENV-4 RNA transfection. Both chimpanzees developed moderate to high $PRNT_{50}$ titers of antibodies against DENV-1, DENV-2 and DENV-3 (Table 1), indicating that the chimpanzees were infected with each of these viruses. Meanwhile, the $PRNT_{50}$ antibody titer against DENV-4 increased approximately 2 fold following infection with DENV-1, DENV-2 and DENV-3.

Chimpanzee Combinatorial Fab Antibody Libraries.

Two phagemid libraries were constructed from bone marrow mRNA of chimpanzee #1618 as follows: (i) library D4 was prepared from the chimpanzee after intrahepatic inoculation with DENV-4 RNA, and (ii) library D1-4 was prepared from the same animal after infection with a mixture of the other three dengue serotype viruses. Phage library D4 was panned three successive rounds against DENV-4 virions immobilized directly on an ELISA plate. After the third panning cycle, plasmid was isolated and cleaved with SpeI and NheI for the expression of soluble Fabs. Library D1-4 was panned for three successive rounds against DENV-4 virions captured by chimpanzee antibodies that were used to coat an ELISA plate. In this manner, possible conformational distortions of the DENV-4 virion surface due to direct coating on a solid phase might be minimized. Similarly, after the third panning, plasmid was isolated and cleaved with SpeI and NheI for the expression of soluble Fabs.

Identification and Characterization of Chimpanzee Fabs Specific to DENV-4.

*E. coli* transformants were screened for production of soluble Fabs capable of binding to DENV-4. Plasmid containing the Fab insert was analyzed by digestion with BstNI in order to select distinct clones. Sequence analysis of the $V_H$ and $V_L$ DNA inserts identified Fabs 5A7, 3C1, 3E4, and 7G4 in library D4. Fabs 5H2 and 5D9, which varied in the $V_L$ sequences but had a nearly identical $V_H$ sequence (a single amino acid difference in the FR3 region), were recovered from library D1-4 (FIG. 2). The sequences in the heavy chain complementarity-determining region 3 (CDR3) (Wu, T. et al. 1993 *Proteins: Structure, Functions and Genetics* 16:1-7), critical for antigen binding, showed a greater diversity than the sequences in other regions among these Fabs. A sequence similarity search of the available human immunoglobulin genes was conducted to determine the specific germ line origin of these chimpanzee Fab fragments. The chimpanzee $V_H$ and $V_L$ sequences and their most related human immunoglobulin genes of the germ line VH or Vκ families are shown (Table 2). These chimpanzee $V_H$ or $V_L$ sequences and their human homologues shared 88-95% identity, excluding the CDR3 region.

Antigenic Specificity of Chimpanzee Fab Monoclonal Antibodies.

First, the binding activity of the Fab antibodies to DENV-4 was analyzed by ELISA. All six selected Fabs showed strong binding to DENV-4 virions (Table 3). Chimpanzee Fab 1F2, which was selected from library D4 for its ability to bind anti-human F(ab)'$_2$ but not DENV-4, was used as the control.

Figure 3A:
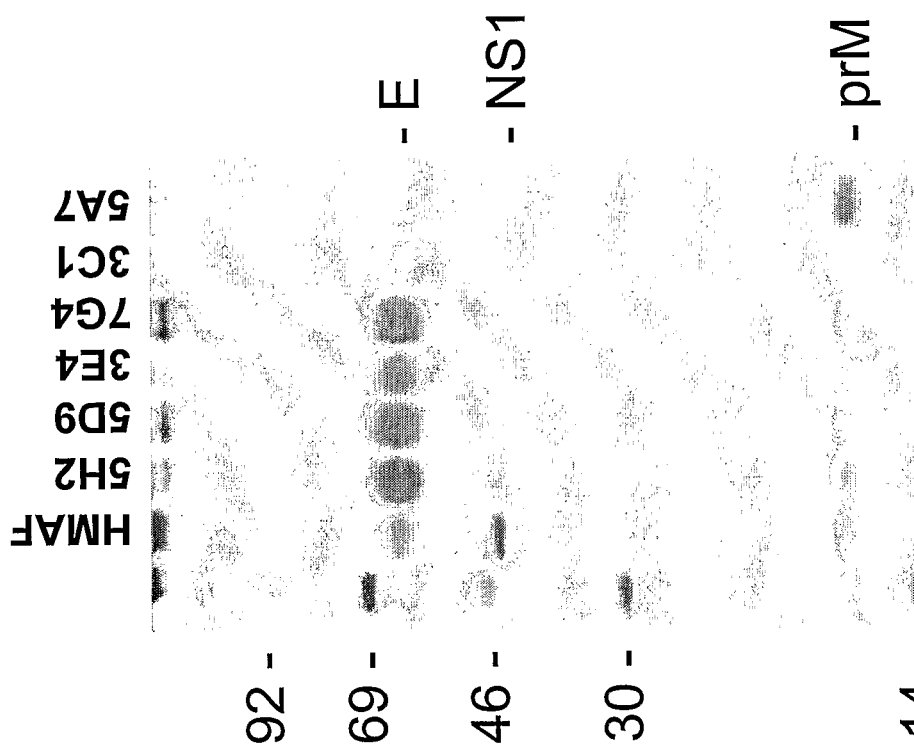
FIG. 3. Analysis of antigenic specificity by radioimmunoprecipitation. (A) $^{35}$S-methionine labeled lysates of DENV-4-infected Vero cells were precipitated with the various Fab preparations indicated. (B) $^{35}$S-methionine labeled lysates were prepared from CV-1 cells infected with vaccinia virus recombinant vDENV-4 prM or vDENV-E containing the full length coding sequence of prM or E, respectively. E+prM, precipitations with a mixture of both lysates; HMAF, precipitation using HMAF raised against DENV-4.
Figure 3B:
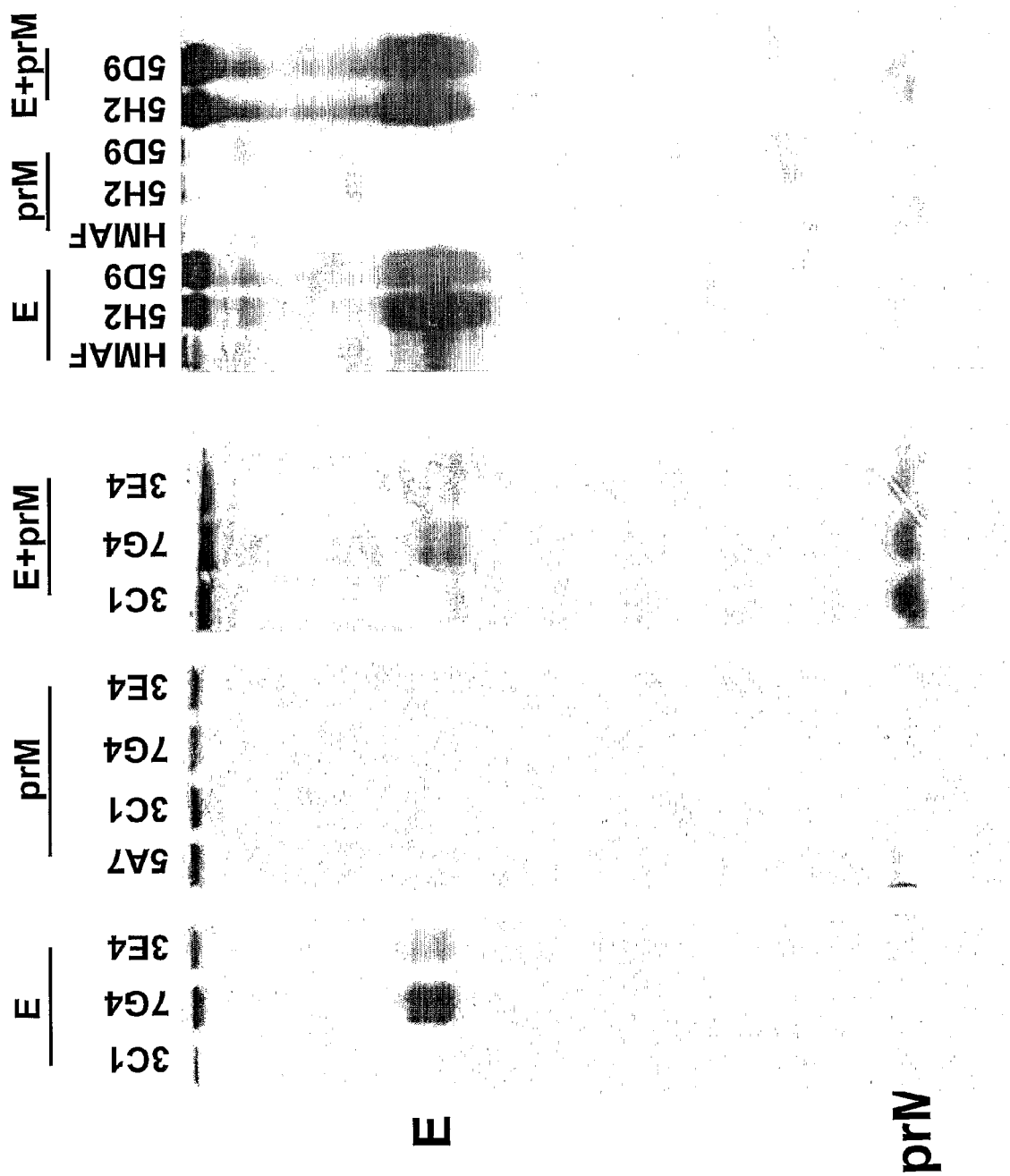

A cross-reactivity to DENV-1, DENV-2 or DENV-3 was detected for Fabs 3E4, 7G4 and 5A7. Fab 3C1 also cross-reacted with DENV-2 at a low titer. Fabs 5H2 and 5D9 showed no detectible cross-reactivity to DENV-1, DENV-2 or DENV-3 virus. Radioimmunoprecipitation using a lysate of DENV-4 infected Vero cells was then performed to determine the antigen-binding specificity (FIG. 3A). Fab 5A7 selectively precipitated prM. All other Fabs precipitated both E and prM. The amount of prM relative to E precipitated varied, depending on the Fab. Radioimmunoprecipitation was again performed by using labeled E or prM prepared individually in recombinant vaccinia virus-infected cells (FIG. 3B). Fabs 3E4 and 7G4 precipitated E but not prM. Fab 3C1 precipitated neither E nor prM. Fab 5D9 precipitated E but not prM, whereas Fab 5H2 precipitated E and a trace of prM. When the labeled antigens were mixed, coprecipitation of prM and E was again detected for Fabs 3E4, 7G4, 3C1 and 5H2.

Mapping Fab Antibody-binding Sites on DENV-4 Virions by Competition ELISA.

Figure 4:
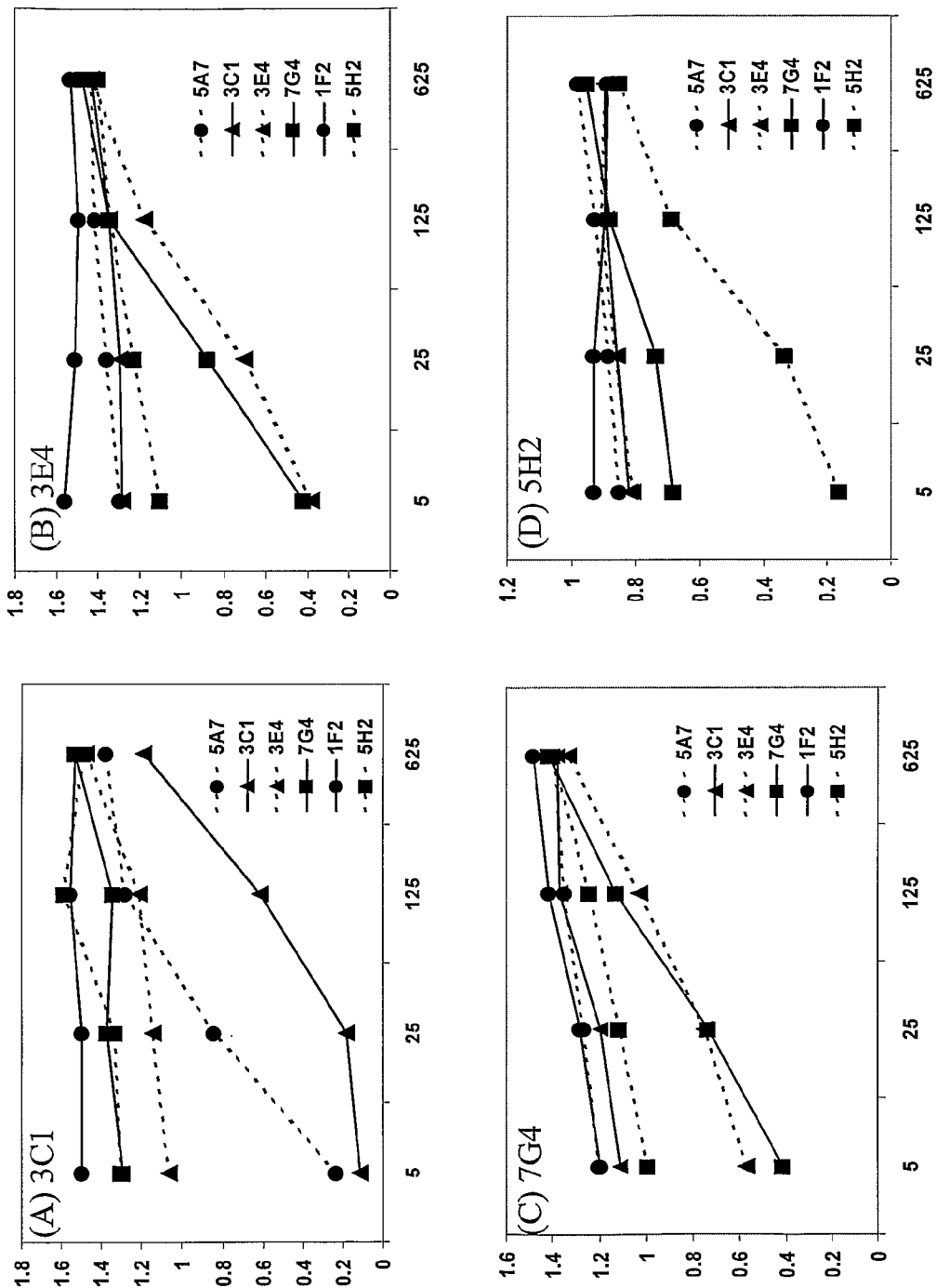
FIG. 4. Epitope analysis of chimpanzee Fab antibodies against DENV-4 by competition ELISA. Selected Fabs were affinity purified, biotinylated and used for analysis of binding reactivity to DENV-4 virions by competition ELISA in the presence of competing, unlabeled Fabs. (A) Biotinylated Fab 3C1; (B) Biotinylated Fab 3E4; (C) Biotinylated Fab 7G4; (D) Biotinylated Fab 5H2. Chimpanzee Fab 1F2, which did not bind to DENV-4, was used as a negative control. The numbers on the Y-axis are OD readings and the X-coordinate represents reciprocal dilutions of the competing Fabs.

Biotinylated Fabs 3C1, 3E4, 7G4 and 5H2 were each tested for binding to DENV-4 in the presence of an unlabeled, competing Fab. Chimpanzee Fab 1F2, which did not bind DENV-4, was analyzed in parallel. Fab 5D9, which was nearly identical to Fab 5H2, was not tested. The result (FIG. 4) showed that binding of Fab 3C1 to DENV-4 was competed by Fab 5A7, but not by Fab 3E4, 7G4, 5H2 or 1F2. Thus, the binding site on prM for Fab 3C1 overlapped with that for Fab 5A7. Fab 3E4 and Fab 7G4 also competed with each other for binding to DENV-4, indicating that their binding sites on E overlapped. The binding site on E for Fab 5H2 was unique, as binding competition with other Fabs was not observed.

DENV-4 and Cross-serotype Neutralizing Activity of Fab Antibodies.

Affinity-purified Fabs were used for $PRNT_{50}$ determination (Table 4). Similar to the Fab 1F2 control, prM-specific Fab 5A7 or 3C1 did not neutralize DENV-4. Fabs 3E4 and 7G4 exhibited a low DENV-4-neutralizing activity with a $PRNT_{50}$ titer at 91 µg/ml or greater. Fab 3E4, which was most cross-reactive to DENV-1, DENV-2 or DENV-3, was used in a cross-serotype neutralization assay. The cross-neutralizing activity against DENV-1, DENV-2 or DENV-3 was lower than that detected for DENV-4. Importantly, Fab 5H2 and Fab 5D9 neutralized DENV-4 efficiently, with a $PRNT_{50}$ titer of 0.24 and 0.58 µg/ml, respectively.

Humanized Chimpanzee Full-length IgG1 Antibodies Produced in CHO Cells.

Figure 1B:
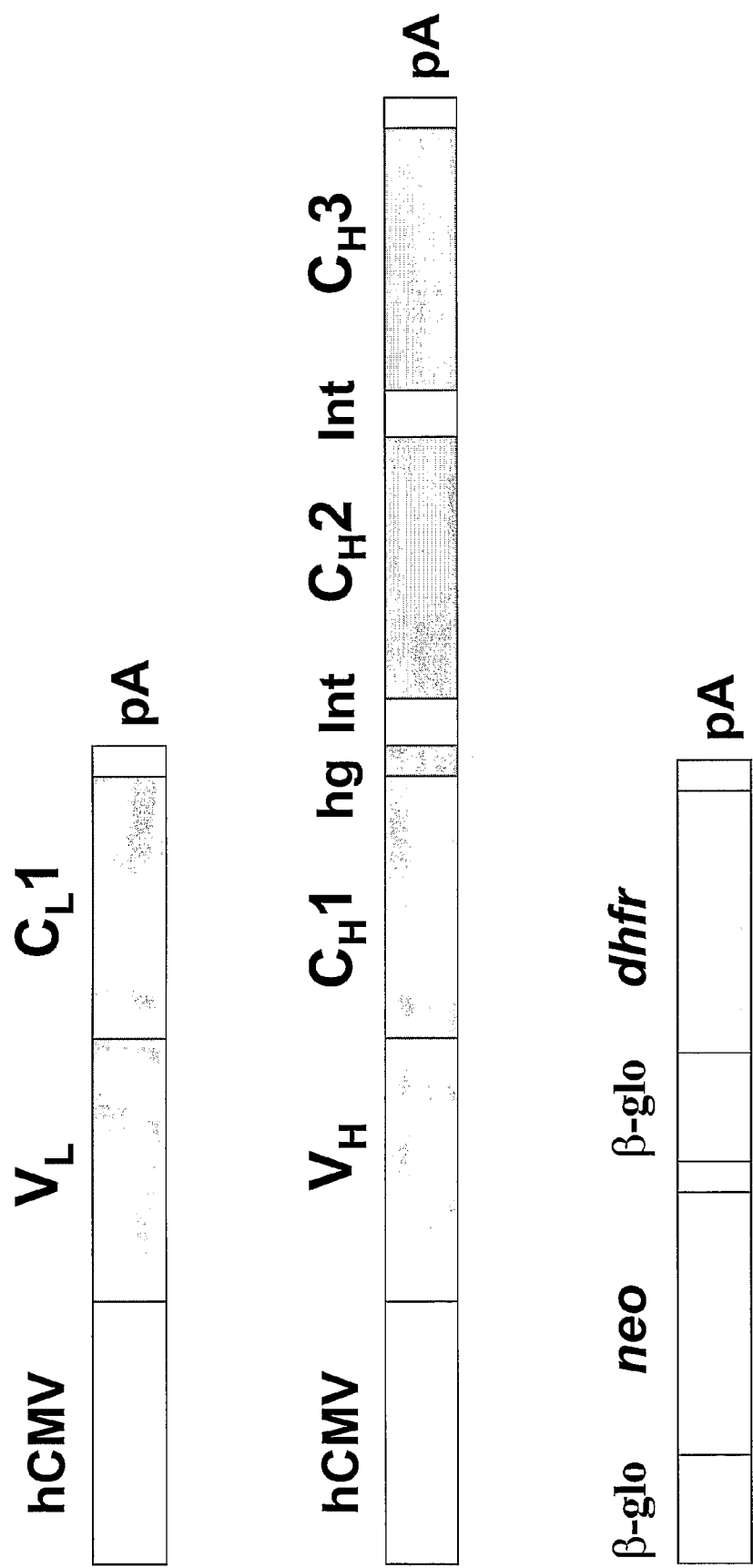
Figure 5:
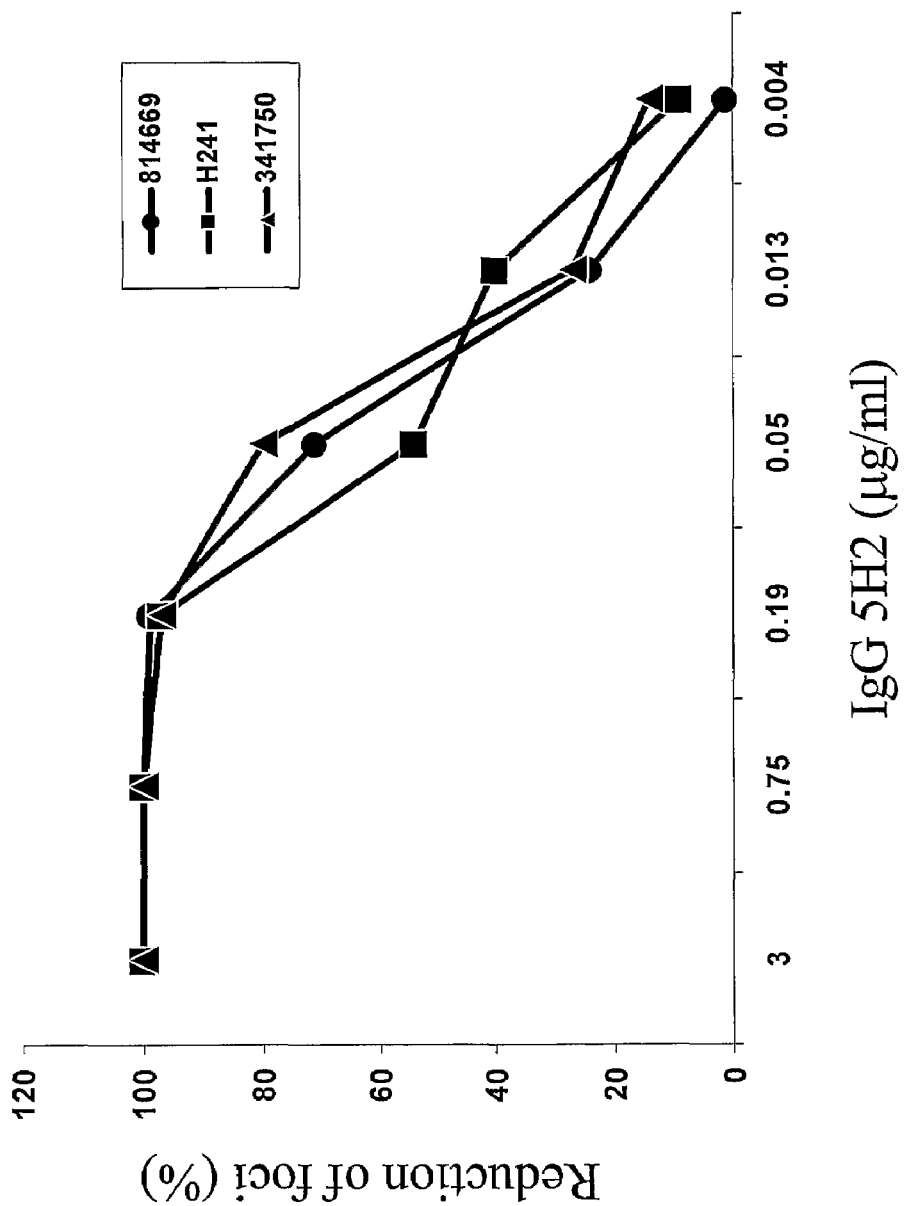
FIG. 5. In vitro neutralization of DENV-4 strains by humanized chimpanzee antibody IgG1 5H2. Full-length antibody IgG1 5H2 was concentrated from the culture medium of transformed CHO cells selected with $2\times10^{-7}$ M methotrexate and then affinity purified through a protein A column. The neutralizing activity of the antibody preparation was tested by PRNT against DENV-4 H241, isolated in the Philippines, and DENV-4 814669 and DEV-4 341750, isolated in the Caribbean.

Production of full-length antibodies from the Fab γ1/κ sequences was achieved with expression vector pFab CMV dhfr, which provides a portion of the hinge and the entire $C_H2$ and $C_H3$ sequences of the human gamma-1 heavy chain (FIG. 1). A dhfr gene was inserted into the vector for selection of antibody-producing CHO cells with methotrexate and for gene copy amplification. Other modifications of the expression vector included conversion of the chimpanzee-specific hinge sequence to the human counterpart and an A to G substitution at the last nucleotide of the intron between $CH_2$ and $CH_3$ exons of the heavy chain sequence. Thus, the product was a full-length, chimeric human-chimpanzee (humanized) IgG1 antibody. Fab 5H2 was chosen for conversion to the whole IgG1 antibody. The full-length IgG1 5H2 was secreted into the culture medium of the transformed CHO cells, and the yield of the affinity-purified product was approximately 1.8 mg per liter. Affinity-purified IgG1 5H2 was compared with Fab 5H2 for binding affinity to DENV-4 by ELISA. The IgG1 5H2 and Fab 5H2 had equilibrium affinity constants (Kd) of 0.24 nM and 0.42 nM, respectively. IgG1 5H2 neutralized three DENV-4 strains from two geographic regions in vitro at a similar high $PRNT_{50}$ titer of 0.03-0.05 µg/ml (FIG. 5). Humanized IgG1 5H2 represents the first DENV-4-neutralizing monoclonal antibody of primate origin.

TABLE 1

Serum neutralizing antibody titers of chimpanzees.

| Chimpanzee 1-3 | Infection with DENV- | Neutralizing antibody titer against | | | |
|---|---|---|---|---|---|
| | | DENV-4 | DENV-1 | DENV-2 | DENV-3 |
| 1616 | Pre- | 1031 | <10 | 34 | 80 |
| | Post- | 2380 | 327 | 880 | 610 |
| 1618 | Pre- | 1110 | 23 | 69 | 156 |
| | Post- | 1654 | 730 | 1787 | 1271 |

Chimpanzees were previously inoculated with DENV-4 RNA intra-hepatically and then infected with a mixture of DENV-1, DENV-2 and DENV-3 nine months later. Chimpanzees were infected with a mixture of DENV-1, DENV-2 and DENV-3 at a dose of $10^6$ PFU for each virus. The neutralizing antibody titer was the reciprocal of the serum dilution that yielded a 50% plaque reduction.

TABLE 2

Sequence similarities between chimpanzee Fab antibodies and their most related human germ line immunoglobulin genes.

| Chimp. Fab | $V_H$ Homologue | | | $V_L$ Homologue | | |
|---|---|---|---|---|---|---|
| | Family (gene) | % Identity | Ref. cited | Family (gene) | % Identity | Ref. Cited |
| 5A7 | VH3 (COS-6) | 95 | a | Vκ3 (DPK-23) | 90 | b |
| 3C1 | VH1 (DP-10) | 88 | a | Vκ1 (L12a) | 92 | c |
| 3E4 | VH1 (DP-10) | 88 | a | Vκ2 (DPK-8) | 88 | b |
| 7G4 | VH3 (DP-54) | 92 | a | Vκ1 (L12a) | 95 | c |
| 5H2 | VH4 (DP-71) | 89 | a | Vκ1 (Va) | 94 | d |
| 5D9 | VH4 (DP-71) | 88 | a | Vκ1 (Va) | 93 | d |

The DNAPlot program was used to search for the most homologous sequence of human IgG molecules in the data base. The percent identity in the $V_H$ or $V_L$ region excluding CDR3 is included.
a. Tomlinson, I. M. et al. 1992 J. Mol. Biol. 227: 776-798
b. Cox, J. P. et al. 1994 Eur. J. Immunol. 24: 827-836
c. Huber, C. et al. 1993 Eur. J. Immunol. 23: 2868-2875
d. Pech, M. et al. 1985 J. Mol. Biol. 183: 291-299

TABLE 3

Binding activities of Fab monoclonal antibodies to DENV-4 and other dengue virus serotypes as determined by ELISA.

| Fab | ELISA titer of Fab binding to | | | |
|---|---|---|---|---|
| | DENV-4 | DENV-1 | DENV-2 | DENV-3 |
| 5A7 | 3.41 | 2.51 | 2.51 | 2.51 |
| 3C1 | 3.71 | 1.30 | 3.11 | 1.30 |
| 3E4 | 4.61 | 4.61 | 4.31 | 4.61 |
| 7G4 | 4.01 | 4.01 | 4.01 | 4.01 |
| 5D9 | 3.41 | <1.0 | <1.0 | <1.0 |
| 5H2 | 4.01 | <1.0 | <1.0 | <1.0 |
| 1F2* | 1.30 | <1.0 | <1.0 | <1.0 |

Microtiter plates were coated with DENV-1, DENV-2, DENV-3 or DENV-4 virions. The starting amount of each Fab in ELISA was approximately 300 µg/ml. Data are presented as $\log_{10}$ of the reciprocal dilution that gave OD reading of twofold or higher than the background.
*Chimpanzee Fab from library D4 was used as negative control for binding to DENV-4 and other dengue virus serotypes.

TABLE 4

DENV-4 neutralizing titer of chimpanzee Fab antibodies.

| Fab | Phase library | $PRNT_{50}$ titer (µg/ml) |
|---|---|---|
| 5A7 | D4 | >200 |
| 3C1 | D4 | >200 |
| 7G4 | D4 | 121 |
| 3E4 | D4 | 91 |
| 5D9 | D1-4 | 0.58 |
| 5H2 | D1-4 | 0.24 |
| 1F2* | D4 | >200 |

Affinity-purified chimpanzee Fabs were tested for DENV-4 neutralization by PRNT and the $PRNT_{50}$ titer was calculated.
*Chimpanzee Fab that did not bind to DENV-4.

Protocol 1

Preparation of Serotypes DENV-1 TO DENV-4.

Mosquito C6/36 cells were grown in minimum essential medium (EM) supplemented with 10% fetal calf serum. Confluent C6/36 cells were infected with DENV-4 at 0.1 multiplicity of infection (MOI) in MEM containing 2% fetal calf serum and incubated at 28° C. The medium from the infected cells was harvested at 7 days and again at 10 days. It was clarified by centrifugation at 3,000 rpm in a JA10 rotor (1,000 g) and then centrifuged at 9,000 rpm in a JA10 rotor (15,000 g) overnight. The DENV-4 pellet was re-suspended in phosphate buffered saline (PBS) for phage panning and for enzyme-linked immunosorbent assay (ELISA). In addition, DENV-4 grown in C6/36 cells in serum-free medium (VP-SFM, Gibco) was directly used for panning and for ELISA. DENV-1 (Western Pacific strain), DENV-2 (prototype New Guinea C strain) and DENV-3 (strain H87) were prepared in serum-free medium from infected simian Vero cells.

Inoculation of Chimpanzees with Infectious DENV-4 RNA and with DENV-1, DENV-2, and DENV-3.

Two dengue virus-seronegative chimpanzees, #1616 and #1618, were intrahepatically inoculated with infectious RNA transcripts made from the full-length cDNA clone of DENV-4 strain 814669 (Lai, C. J. et al. 1991 *Proc. Natl. Acad. Sci. USA*. 88:5139-5143). A blood sample was collected weekly from each animal for analysis of the serum ALT levels and for analysis of antibodies to DENV-4. Eleven weeks after DENV-4 RNA inoculation, bone marrow was aspirated from the iliac crest of each chimpanzee and a combinatorial antibody library (designated library D4) was constructed. Nine and one-half months after inoculation with DENV-4 RNA, each of the chimpanzees was inoculated subcutaneously with a mixture of DENV-1, DENV-2 and DENV-3, each at $10^6$ plaque forming units (PFU), in 1 ml of MEM (Gibco) plus 0.25% human serum albumin. Six weeks after inoculation with the dengue virus mixture, serum samples were collected for analysis of antibody response. Twelve weeks after inoculation with DENV-1, DENV-2 and DENV-3, bone marrow was aspirated again and a second antibody library (designated library D1-4) was constructed. Both libraries were prepared from bone marrow of chimpanzee #1618, which developed slightly higher antibody titers against DENV-1, DENV-2 and DENV-3 than did chimpanzee #1616.

Construction of γ1/κ chimpanzee Fab Antibody Libraries.

The lymphocytes from bone marrow were separated on a Ficoll-Paque gradient by centrifugation and aliquots of approximately $1 \times 10^7$ cells/ml in MEM containing 10% dimethyl sulfoxide (DMSO) and 10% fetal calf serum were stored over liquid nitrogen. Total RNA was extracted from $3 \times 10^7$ lymphocytes using the RNA Extraction Kit (Stratagene) and mRNA was reverse-transcribed using oligo (dT) as primer (ThermoScript RT-PCR System, Invitrogen). The κ light chain DNA was amplified from the cDNA product by PCR with seven pairs of human κ light chain family-specific 5' primers and a 3' primer in the constant domain (Barbas, C. F. et al. 1991 *Proc. Natl. Acad. Sci.* 88:7978-7982; Glamann, J. et al. 1998 *J. Virol.* 72:585-592; Persson, M. A. et al. 1991 *Proc. Natl. Acad. Sci.* 88:2432-2436; Schofield, D. J. et al. 2000 *J. Virol.* 74:5548-5555). The γ1 heavy chain Fd cDNA was amplified using nine human γ1 heavy chain family-specific 5' primers plus a chimpanzee γ1-specific 3' primer (Glamann, J. et al. 1998 *J. Virol.* 72:585-592; Schofield, D. J. et al. 2000 *J. Virol.* 74:5548-5555). A thirty-cycle PCR at 94 C for 15 s, 52 C for 50 s and 68 C for 90 s was performed with AmpliTaq DNA polymerase (Perkin Elmers).

Cloning of the chimpanzee κ light chain and γ1 heavy chain DNA fragments into the pComb 3H phage display vector was performed as described (Barbas, C. F. et al. 1991 *Proc. Natl. Acad. Sci.* 88:7978-7982; Williamson, R. A. I et al. 1993 *Proc. Nat. Acad. Sci.* 90:41413-4145 [Erratum 91:1193, 1994]). Briefly, amplified κ light chain DNA fragments were pooled, digested with Sac I and XbaI, and then cloned into pComb 3H (Persson, M. A. et al. 1991 *Proc. Natl. Acad. Sci.* 88:2432-2436) by transformation of electrocompetent *E. coli* XL-1 Blue (Stratagene). A plasmid containing the γ1 light chain DNA inserts was prepared from *E. coli* transformants and then cleaved with SpeI and XhoI for insertion with amplified γ1 heavy chain DNA fragments cleaved with the same enzymes. The plasmid containing both the heavy chain and the light chain DNA inserts was used for transformation of *E. coli* XL-1 Blue by electroporation. In both electroporation steps, the ligated DNA mixture yielded a library size of 1-3× $10^8$ *E. coli* colonies.

Panning of Phase Library and Isolation of DENV-4-specific Soluble Fabs.

The construction of phage display libraries, recovery and transfer of Fab sequences, and identification of *E. coli* transformants expressing DENV-4-specific soluble Fabs were carried out as described (Glamann, J. et al. 1998 *J. Virol.* 72:585-592; Schofield, D. J. et al. 2000 *J. Virol.* 74:5548-5555). Briefly, approximately $10^8$ transformants were grown in 2YT broth containing 1% glucose, 10 µg/ml tetracycline and 100 µg/ml ampicillin for 3 hr at 37° C. The bacterial culture was then infected with helper phage VSC M13 (Stratagene) at 50 MOI to generate the phage library. The phage library D4 was panned by affinity binding on DENV-4 virions used to coat an ELISA plate that was blocked with 3% nonfat powdered milk in PBS to reduce non-specific binding. The phage library D1-4 was panned by affinity binding on DENV-4 virions captured by a chimpanzee serum immobilized on an ELISA plate to minimize conformational changes of the DENV-4 antigenic structure. Following three cycles of panning, the selected phage mixture was used to infect *E. coli* XL-1 Blue, and replicative form DNA (phagemid) was prepared. The phagemid was cleaved with NheI and SpeI and recircularized to remove the phage gene III portion of the fused Fab sequence. *E. coli* XL-1 Blue were transformed with the circularized DNA, and colonies that yielded soluble Fab fragments reactive to DENV-4 virus were screened by ELISA.

DNA Sequencing of DENV-4 Specific Fab Clones.

Plasmid from the selected *E. coli* transformants was initially analyzed by BstN1 digestion to identify Fab clones with distinct patterns. Sequence analysis of the Fab $V_H$ and $V_L$ DNA segments was performed on an automated DNA sequencer with a fluorescence dideoxynucleotide terminator cycle sequencing kit with Taq DNA polymerase (Perkin-Elmer). The following primers were used: 5' ACAGC-TATCGCGATTGCAGTG (LC-1) (SEQ ID NO: 193) and 5' CACCTGATCCTCAGATGGCGG (LC-4) (SEQ ID NO: 194) for sequencing the $V_L$ segment; 5' ATTGCCTACG-GCAGCCGCTGG (HC-1) (SEQ ID NO: 195) and 5' GGAAGTAGTCCTTGACCAGGC (HC-4) (SEQ ID NO: 196) for sequencing both DNA strands of the $V_H$ segment (Glamann, J. et al. 1998 *J. Virol.* 72:585-592; Schofield, D. J. et al. 2000 *J. Virol.* 74:5548-5555). Software Vector NTI (InforMax) was used for sequence analysis. The DNAPLOT software program (MRC Center for Protein Engineering) was used to search for human immunoglobulin homologues in the data base.

Production and Purification of Fab Antibodies.

Selected *E. coli* colonies were grown in 1 liter of L-broth containing 1% glucose and 100 µg/ml ampicillin and 10 µg/ml tetracycline to an early exponential growth phase (optical density at 600 nm approximately 0.2) at 30° C. The bacteria were then transferred to 2 liters of L-broth containing 100 µg/ml ampicillin and 10 µg/ml tetracycline and grown at 30° C. in the presence of 0.1 mM of inducer isopropyl-β-D-thiogalactopyranoside (IPTG) for 5 h. The bacteria were pelleted and resuspended in 20 ml of extraction buffer containing 50 mM sodium phosphate, 10 mM Tris-HCl, pH 8.0, 100 mM NaCl (Clontech), and 0.1 mM protease inhibitor 4-(2-aminoethyl)-benzene sulfonyl fluoride (AEBSF). After three cycles of freezing and thawing to release the soluble Fab product from the bacterial periplasm, the preparation was clarified by centrifugation at 10,000 rpm in a JA-20 rotor (10,000 g) for 60 min. The histidine-tagged Fab in the supernatant was purified through a column containing a 1-ml bed volume of TALON metal affinity resin (Clontech) using the pH elution procedure as suggested by the manufacturer. The Fab purity was verified by polyacrylamide gel electrophoresis using purified human IgG F(ab')$_2$ (Cappel) as a marker. The Fab concentration was determined colorimetrically using the BCA protein assay kit (Pierce).

Biotinylation of Purified Fab Fragments and Competition ELISA.

Purified Fabs were biotinylated with EZ-Link NHS-LC-biotin (Pierce) according to the procedure suggested by the supplier. After extensive dialysis against PBS, the biotin-labeled Fab was tested for binding to DENV-4 coated on wells of a microtiter plate. For competition ELISA, a fixed concentration of biotinylated Fab was mixed with a competing Fab in serial dilution and the mixture was added to the DENV-4-coated wells. Streptavidin-alkaline phosphatase was used for detection of biotinylated Fab bound to DENV-4.

Radiolabeling of DENV-4 Antigens and Radio-immunoprecipitation

Infection with DENV-4 or recombinant vaccinia virus and subsequent radiolabeling of infected cells were performed as described (Falgout, B. et al. 1990. *J. Virol.* 64:4356-4363). Confluent Vero cells in a T-25 flask were infected with DENV-4 strain 814669 at 1 MOI and incubated for 4 days at 37° C. Infected cells were rinsed once, starved for methionine in methionine-free MEM for 30 min and, then labeled with $^{35}$S-methionine at 150 µCi/ml (specific activity, 3000 Ci/mM). After a 6-h labeling period, cells were rinsed with cold PBS and lysed in 2 ml of radioimmunoprecipitation assay (RIPA) buffer containing 1% sodium deoxycholate, 1% NP-40, 0.1% sodium dodecyl sulphate (SDS), 0.15 M NaCl, and 0.1 M Tris, pH 7.5. Confluent CV-1 cells were infected with 5 MOI of recombinant vaccinia virus vDENV-4 PrM (Bray, M., and C. J. Lai. 1991 *Virology* 185:505-508) or vDENV-4 E (Men, R. et al. 1991 *J. Virol.* 65:1400-1407) containing the full-length PrM or E coding sequence, respectively, for 15 h at 37° C. Infected cells were rinsed and starved for methionine in methionine-free MEM, placed in the labeling medium for 2 h, and then lysed in RIPA buffer as described. A 20-µl labeled lysate of DENV-4- or recombinant vaccinia virus-infected cells was mixed with 10 µl of the Fab fragment to be tested and 70 µl RIPA buffer, incubated at 4 C overnight, and then mixed with 2 µl of goat anti-human IgG F(ab')$_2$ antibody for 2 h. A 100-µl suspension of protein A-Sepharose beads was added to bind the radioimmune complexes. The Sepharose beads were collected by centrifugation and washed three times with RIPA buffer prior to separation by SDS-12% polyacrylamide gel (acrylamide/bisacrylamide ratio of 37.5:1) electrophoresis. Radiolabeled protein bands on the dried gel were visualized by exposure to an X-ray film.

Construction of DNA Recombinants and Expression of Full-length IgG1 in Chinese Hamster Ovary (CHO) Cells.

The expression vector pFab CMV (Sanna, P. P. et al. 1999 *Immunotechnology* 4:185-188) was re-engineered for IgG1 production (FIG. 1). The vector contained a neomycin phosphotransferase gene (neo), located between the two human CMV (hCMV) promoters, and a β-lactamase gene (amp), located between the two polyA sites as mapped by restriction digestion and by sequencing. The neo and amp locations differed from the published map. A di-hydrofolate reductase (dhfr) gene together with the transcription signals was inserted at the unique NotI site in the original vector as the selecting marker and for gene amplification (Wood, C. R. et al. 1990 *J. Immunol.* 145:3011-3016 ). The dhfr gene insert was the 1.4 kb DNA fragment from Pvu II/Afe I cleavage of pCDHC68B (Ames, R. S. et al. 1995 *J. Immunol. Methods.* 184:177-180). The original plasmid vector contained an A at the last nucleotide position of the intron that precedes the $C_H3$ exon. This variant nucleotide was converted to G to allow proper RNA splicing for full-length IgG1 expression. The Fab 5H2 κ, light chain DNA segment cleaved by SacI and XbaI was first inserted into the expression vector. The resulting recombinant was then added with the γ1 heavy chain DNA segment cleaved by XhoI and SpeI, which was regenerated by PCR using the Fab 5H2 DNA template and appropriate primers. The chimpanzee-specific sequence in the hinge region together with the variant sequences introduced during plasmid construction were converted to the human hinge sequence using positive strand primer 5'

GACAAAACTCACACATGTCCACCGTGCCCA (SEQ ID NO: 197), which introduced a PciI site (underlined) with silent mutations (Ehrich, P. H. et al. 1991 *Mol. Immunol.* 28:319-322; Takahashi, N. et al. 1982 *Cell* 29:671-679). Accordingly, the IgG1 antibody product would contain the chimpanzee $V_H$ and $C_H1$ sequences and the entire human hinge, $C_H2$ and $C_H3$ sequences.

CHO/dhfr- (duk-) cells were purchased from American Type Culture Collection. Production of the whole IgG1 in CHO/dhfr-cells was carried out by transfection with RsrII-cleaved recombinant plasmid in the presence of Lipofectamine (Gibco). Two days after transfection, cells in a T25 flask were re-plated in Iscove's modified Dulbecco medium (Gibco) supplemented with 10% fetal bovine serum plus $10^{-7}$ M methotrexate in the absence of hypoxanthine/thymidine as selecting medium (Dorai, H, and G P Moore. 1987. *J. Immunol.* 139:4232-4241; Wood, C. R. et al. 1990 *J. Immunol.* 145:3011-3016). Transformed CHO cells resistant to $10^{-7}$ M methotrexate appeared approximately two weeks after transfection. Transformed CHO cells producing IgG1 in the medium were identified by ELISA and by plaque reduction neutralization test (PRNT) following sub-cloning in a 96- or 24-well plate. Gene amplification was carried out step-wise by increasing methotrexate concentration to $2 \times 10^{-7}$ M in the selecting medium. CHO cells that produced IgG1 at a high level were selected. The selected CHO cells were adapted to growth in suspension for IgG1 production in serum-free CD CHO medium (Gibco). Medium fluid was concentrated and the IgG1 product was purified through a protein-A affinity column. The full-length IgG1 5H2 antibody was compared with the Fab 5H2 fragment for DENV-4-binding affinity by ELISA. The equilibrium affinity constant (Kd) was calculated as the antibody concentration that gave 50% of maximum binding (Lin, C.-W. and S.-C. Wu. 2003 *J. Virol.* 77:2600-2606; Raffai, R. et al. *J. Biol. Chem.* 275:7109-7116).

Determination of DENV-4 Neutralizing Activity of Fab and Whole IgG1 Antibodies.

Affinity-purified Fab or full-length IgG1 antibodies were analyzed for DENV-4 neutralizing activity by a modification of plaque reduction neutralization test (PRNT), as described (Okuno, Y. et al. 1985 *Arch. Virol.* 86:129-135). Briefly, approximately 50 focus-forming units of DENV-4 were mixed with a serial dilution of Fab or IgG1 antibodies in 250 µl of MEM. The mixture was incubated at 37° C. for 30 min and then used for infection of Vero cell monolayers in a 24-well plate. The cells were overlaid with a semi-solid medium containing 1% Tragacanth gum (Sigma) and incubated at 37° C. for 4 days. Foci of DENV-4 infected cells were visualized following immunostaining with hyperimmune mouse ascites fluid (HMAF) and anti-mouse horseradish peroxidase conjugate (Pierce). The Fab or IgG1 concentration that produced 50% focus reduction was calculated. The neutralizing activity of the IgG1 antibody was tested against DENV-4 strain H241 isolated from the Philippines and two Caribbean DENV-4 isolates, i.e., strain 814669 and strain 341750.

PART 2
Brief Description of the SEQ ID NOs.

| Region | Heavy Chain 1A5 Sequence SEQ ID NO: 97 | Light Chain 1A5 Sequence SEQ. ID. NO: 105 | Heavy Chain 2H7 Sequence SEQ. ID. NO: 113 | Light Chain 2H7 Sequence SEQ. ID. NO: 121 | Heavy Chain 2H5 Sequence SEQ. ID. NO: 129 | Light Chain 2H5 Sequence SEQ. ID. NO: 137 | Heavy Chain 3A2 Sequence SEQ. ID. NO: 145 | Light Chain 3A2 Sequence SEQ. ID. NO: 153 | Heavy Chain 1B2 Sequence SEQ. ID. NO: 161 | Light Chain 1B2 Sequence SEQ. ID. NO: 169 | Heavy Chain 1A10 Sequence SEQ. ID. NO: 177 | Light Chain 1A10 Sequence SEQ. ID. NO: 185 |
|---|---|---|---|---|---|---|---|---|---|---|---|---|
| FR1 | SEQ ID NO: 98 | SEQ ID NO: 106 | SEQ ID NO: 114 | SEQ ID NO: 122 | SEQ ID NO: 130 | SEQ ID NO: 138 | SEQ ID NO: 146 | SEQ ID NO: 154 | SEQ ID NO: 162 | SEQ ID NO: 170 | SEQ ID NO: 178 | SEQ ID NO: 186 |
| CDR1 | SEQ ID NO: 99 | SEQ ID NO: 107 | SEQ ID NO: 115 | SEQ ID NO: 123 | SEQ ID NO: 131 | SEQ ID NO: 139 | SEQ ID NO: 147 | SEQ ID NO: 155 | SEQ ID NO: 163 | SEQ ID NO: 171 | SEQ ID NO: 179 | SEQ ID NO: 187 |
| FR2 | SEQ ID NO: 100 | SEQ ID NO: 108 | SEQ ID NO: 116 | SEQ ID NO: 124 | SEQ ID NO: 132 | SEQ ID NO: 140 | SEQ ID NO: 148 | SEQ ID NO: 156 | SEQ ID NO: 164 | SEQ ID NO: 172 | SEQ ID NO: 180 | SEQ ID NO: 188 |
| CDR2 | SEQ ID NO: 101 | SEQ ID NO: 109 | SEQ ID NO: 117 | SEQ ID NO: 125 | SEQ ID NO: 133 | SEQ ID NO: 141 | SEQ ID NO: 149 | SEQ ID NO: 157 | SEQ ID NO: 165 | SEQ ID NO: 173 | SEQ ID NO: 181 | SEQ ID NO: 189 |
| FR3 | SEQ ID NO: 102 | SEQ ID NO: 110 | SEQ ID NO: 118 | SEQ ID NO: 126 | SEQ ID NO: 134 | SEQ ID NO: 142 | SEQ ID NO: 150 | SEQ ID NO: 158 | SEQ ID NO: 166 | SEQ ID NO: 174 | SEQ ID NO: 182 | SEQ ID NO: 190 |
| CDR3 | SEQ ID NO: 103 | SEQ ID NO: 111 | SEQ ID NO: 119 | SEQ ID NO: 127 | SEQ ID NO: 135 | SEQ ID NO: 143 | SEQ ID NO: 151 | SEQ ID NO: 159 | SEQ ID NO: 167 | SEQ ID NO: 175 | SEQ ID NO: 183 | SEQ ID NO: 191 |
| FR4 | SEQ ID NO: 104 | SEQ ID NO: 112 | SEQ ID NO: 120 | SEQ ID NO: 128 | SEQ ID NO: 136 | SEQ ID NO: 144 | SEQ ID NO: 152 | SEQ ID NO: 160 | SEQ ID NO: 168 | SEQ ID NO: 176 | SEQ ID NO: 184 | SEQ ID NO: 192 |

Deposit of Biological Material

The following biological material has been deposited in accordance with the terms of the Budapest Treaty with the American Type Culture Collection (ATCC), Manassas, Va., on the date indicated:

| Biological material | Designation No. | Date |
|---|---|---|
| Plasmid: Humanized IgG1 1A5 | PTA-6265 | Oct. 22, 2004 |

The Plasmid: Humanized IgG1 1A5 was deposited as ATCC Accession No. PTA-6265 on Oct. 22, 2004 with the American Type Culture Collection (ATCC), 10801 University Blvd., Manassas, Va. 20110-2209, USA. This deposit was made under the provisions of the Budapest Treaty on the International Recognition of the Deposit of Microorganisms for the Purposes of Patent Procedure and the Regulations thereunder (Budapest Treaty). This assures maintenance of a viable culture of the deposit for 30 years from date of deposit. The deposit will be made available by ATCC under the terms of the Budapest Treaty, and subject to an agreement between Applicant and ATCC which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC § 122 and the Commissioner's rules pursuant thereto (including 37 CFR § 1.14). Availability of the deposited biological material is not to be construed as a license to practice the invention in contravention of the rights granted under the authority of any government in accordance with its patent laws.

Detailed Description of the Preferred Embodiment of the Next Part

Passive immunization using monoclonal antibodies from humans or non-human primates represents an attractive alternative to vaccines for prevention of illness caused by dengue viruses and other flaviviruses, including the West Nile virus. In the previous study, we described repertoire cloning to recover Fab fragments from bone marrow mRNA of chimpanzees infected with all four dengue virus serotypes (DENV-1 to DENV-4). In that study we recovered and characterized a humanized IgG1 antibody that efficiently neutralized DENV-4. In this study, the phage library constructed from the chimpanzees was used to recover Fab antibodies against the other three dengue virus serotypes. Serotype-specific neutralizing Fabs were not identified. Instead, we recovered dengue virus-neutralizing Fabs that specifically precipitated the envelope protein and were cross-reactive with all four dengue serotypes. Three of the Fabs competed with each other for binding to DENV-1 and DENV-2, although each of these Fabs contained a distinct CDR3-H sequence. Fabs that shared an identical or nearly identical CDR3-H sequence cross-neutralized DENV-1 and DENV-2 at a similar high 50% plaque reduction (PRNT$_{50}$) titer, ranging from 0.26 to 1.33 µg/ml, and neutralized DENV-3 and DENV-4 but at a titer 10-20 fold lower. One of these Fabs, 1A5, also neutralized the West Nile virus most efficiently among other flaviviruses tested. Fab 1A5 was converted to a full-length antibody in combination with human sequences for production in mammalian CHO cells. Humanized IgG1 1A5 proved to be as efficient as Fab 1A5 for cross-neutralization of DENV-1 and DENV-2 at a titer of 0.48 and 0.95 µg/ml, respectively. IgG1 1A5 also neutralized DENV-3, DENV-4 and the West Nile virus at a PRNT$_{50}$ titer of approximately 3.2-4.2 µg/ml. This humanized antibody is envisioned to be useful for prophylactic and therapeutic application against dengue and other flaviviruses-associated diseases.

Definitions

As used herein, the term "antibody" means an immunoglobulin molecule or a fragment of an immunoglobulin molecule having the ability to specifically bind to a particular antigen. Antibodies are well known to those of ordinary skill in the science of immunology. As used herein, the term "antibody" means not only full-length antibody molecules but also fragments of antibody molecules retaining antigen binding ability. Such fragments are also well known in the art and are regularly employed both in vitro and in vivo. In particular, as used herein, the term "antibody" means not only full-length immunoglobulin molecules but also antigen binding active fragments such as the well-known active fragments F(ab')$_2$, Fab, Fv, and Fd.

As used herein, the term "dengue virus disease" means any disease caused, directly or indirectly, by one of the four serotypes of a dengue virus, which is a flavivirus. Dengue is an acute febrile disease characterized by sudden onset, with headache, fever, prostration, joint and muscle pain, lymphadenopathy, and a rash that appears simultaneously with a temperature rise. A second phase of temperature rise may appear following an afebrile period. Dengue hemorrhagic fever/dengue shock syndrome is an acute disease occurring primarily in children characterized by an abrupt febrile onset followed by hemorrhagic manifestations and circulatory collapse.

As used herein with respect to polypeptides, the term "substantially pure" means that the polypeptides are essentially free of other substances with which they may be found in nature or in vivo systems to an extent practical and appropriate for their intended use. In particular, the polypeptides are sufficiently pure and are sufficiently free from other biological constituents of their hosts cells so as to be useful in, for example, generating antibodies, sequencing, or producing pharmaceutical preparations. By techniques well known in the art, substantially pure polypeptides may be produced in light of the nucleic acid and amino acid sequences disclosed herein. Because a substantially purified polypeptide of the invention may be admixed with a pharmaceutically acceptable carrier in a pharmaceutical preparation, the polypeptide may comprise only a certain percentage by weight of the preparation. The polypeptide is nonetheless substantially pure in that it has been substantially separated from the substances with which it may be associated in living systems.

As used herein with respect to nucleic acids, the term "isolated" means: (1) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification and selection of cells which have been transformed or transfected with the vector. Markers include, for example, genes encoding proteins which increase or decrease either resistance or sensitivity to antibiotics or other compounds, genes which encode enzymes whose activities are detectable by standard assays known in the art (e.g., B-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

Novel Anti-Dengue Virus Monoclonal Antibodies

The present invention derives, in part, from the isolation and characterization of novel chimpanzee Fab fragments and their humanized monoclonal antibodies that selectively bind and neutralize dengue type 1, 2, 3 and/or 4 virus and that we have designated 1A5, 2H7, 2H5, 3A2, 1B2, and 1A10. As described more fully herein, these new monoclonal antibodies have been shown to bind and neutralize the dengue type 1, 2, 3 and/or 4 virus. The paratopes of the 1A5, 2H7, 2H5, 3A2, 1B2, and 1A10 Fab fragments associated with the neutralization epitopes on the dengue type 1, 2, 3 and/or 4 virus are defined by the amino acid (aa) sequences of the immunoglobulin heavy and light chain V-regions depicted in FIG. 6 and, for 1A5, SEQ ID NO: 97 and SEQ ID NO: 105;
  for 2H7, SEQ ID NO: 113 and SEQ ID NO: 121;
  for 2H5, SEQ ID NO: 129 and SEQ ID NO: 137;
  for 3A2, SEQ ID NO: 145 and SEQ ID NO: 153;
  for 1B2, SEQ ID NO: 161 and SEQ ID NO: 169; and
  for 1A10, SEQ ID NO: 177 and SEQ ID NO: 185.

The nucleic acid sequences coding for these aa sequences were identified as described herein, by sequencing the Fab heavy chain and light chain fragments. Due to the degeneracy of the DNA code, the paratope is more properly defined by the derived aa sequences depicted in FIG. 6 and SEQ ID NOs.

In one set of embodiments, the present invention provides the full-length, humanized monoclonal antibody of the 1A5 antibody, or the 2H7, 2H5, 3A, 1B2, or 1A10 antibody or other dengue type 1, 2, 3 and/or 4 virus antibody in isolated form and in pharmaceutical preparations. Similarly, as described herein, the present invention provides isolated nucleic acids, host cells transformed with nucleic acids, and pharmaceutical preparations including isolated nucleic acids, encoding the full-length, humanized monoclonal antibody of the 1A5 antibody, or the 2H7, 2H5, 3A2, 1B2, or 1A10 antibody or other dengue type 1, 2, 3 and/or 4 virus antibody. Finally, the present invention provides methods, as described more fully herein, employing these antibodies and nucleic acids in the in vitro and in vivo diagnosis, prevention and therapy of dengue virus disease.

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of a full-length antibody. Similarly, an antibody from which the Fc region has been enzymatically cleaved, or which has been produced without the Fc region, designated an Fab fragment, retains one of the antigen binding sites of a full-length antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986, supra; Roitt, 1991, supra). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

The complete amino acid sequences of the antigen-binding Fab portion of the 1A5 monoclonal antibody as well as the relevant FR and CDR regions are disclosed herein. SEQ ID NO: 97 discloses the amino acid sequence of the Fd fragment of 1A5. The amino acid sequences of the heavy chain FR1, CDR1, FR2, CDR2, FR3, CDR3 and FR4 regions are disclosed as SEQ ID NO: 98 through SEQ ID NO: 104, respectively. SEQ ID NO: 105 discloses the amino acid sequence of the light chain of 1A5. The amino acid sequences of the light chain FR1, CDR1, FR2, CDR2, FR3, CDR3 and FR4 regions are disclosed as SEQ ID NO: 106 through SEQ ID NO: 112, respectively.

The complete amino acid sequences of the antigen-binding Fab portion of the 2H7 monoclonal antibody as well as the relevant FR and CDR regions are disclosed herein. SEQ ID NO: 113 discloses the amino acid sequence of the Fd fragment of 2H7. The amino acid sequences of the heavy chain FR1, CDR1, FR2, CDR2, FR3, CDR3 and FR4 regions are disclosed as SEQ ID NO: 114 through SEQ ID NO: 120, respectively. SEQ ID NO: 121 discloses the amino acid sequence of the light chain of 2H7. The amino acid sequences of the light chain FR1, CDR1, FR2, CDR2, FR3, CDR3 and FR4 regions are disclosed as SEQ ID NO: 122 through SEQ ID NO: 128, respectively.

The complete amino acid sequences of the antigen-binding Fab portion of the 2H5 monoclonal antibody as well as the relevant FR and CDR regions are disclosed herein. SEQ ID NO: 129 discloses the amino acid sequence of the Fd fragment of 2H5. The amino acid sequences of the heavy chain FR1, CDR1, FR2, CDR2, FR3, CDR3 and FR4 regions are disclosed as SEQ ID NO: 130 through SEQ ID NO: 136, respectively. SEQ ID NO: 137 discloses the amino acid sequence of the light chain of 2H5. The amino acid sequences of the light chain FR1, CDR1, FR2, CDR2, FR3, CDR3 and FR4 regions are disclosed as SEQ ID NO: 138 through SEQ ID NO: 144, respectively.

The complete amino acid sequences of the antigen-binding Fab portion of the 3A2 monoclonal antibody as well as the relevant FR and CDR regions are disclosed herein. SEQ ID NO: 145 discloses the amino acid sequence of the Fd fragment of 3A2. The amino acid sequences of the heavy chain FR1, CDR1, FR2, CDR2, FR3, CDR3 and FR4 regions are disclosed as SEQ ID NO: 146 through SEQ ID NO: 152, respectively. SEQ ID NO: 153 discloses the amino acid sequence of the light chain of 3A2. The amino acid sequences of the light chain FR1, CDR1, FR2, CDR, FR3, CDR3 and FR4 regions are disclosed as SEQ ID NO: 154 through SEQ ID NO: 160, respectively.

The complete amino acid sequences of the antigen-binding Fab portion of the 1B2 monoclonal antibody as well as the relevant FR and CDR regions are disclosed herein. SEQ ID NO: 161 discloses the amino acid sequence of the Fd fragment of 1B2. The amino acid sequences of the heavy chain FR1, CDR1, FR2, CDR2, FR3, CDR3 and FR4 regions are disclosed as SEQ ID NO: 162 through SEQ ID NO: 168, respectively. SEQ ID NO: 169 discloses the amino acid sequence of the light chain of 1B2. The amino acid sequences of the light chain FR1, CDR1, FR2, CDR2, FR3, CDR3 and FR4 regions are disclosed as SEQ ID NO: 170 through SEQ ID NO: 176, respectively.

The complete amino acid sequences of the antigen-binding Fab portion of the 1A10 monoclonal antibody as well as the relevant FR and CDR regions are disclosed herein. SEQ ID NO: 177 discloses the amino acid sequence of the Fd fragment of 1A10. The amino acid sequences of the heavy chain FR1, CDR1, FR2, CDR2, FR3, CDR3 and FR4 regions are disclosed as SEQ ID NO: 178 through SEQ ID NO: 184, respectively. SEQ ID NO: 185 discloses the amino acid sequence of the light chain of 1A10. The amino acid sequences of the light chain FR1, CDR1, FR2, CDR2, FR3, CDR3 and FR4 regions are disclosed as SEQ ID NO: 186 through SEQ ID NO: 192, respectively.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of full-length antibodies with antigen-binding ability, are often referred to as "chimeric" antibodies.

Thus, as will be apparent to one of ordinary skill in the art, the present invention also provides for $F(ab')_2$, Fab, Fv and Fd fragments of the 1A5 antibody, or the 2H7, 2H5, 3A2, 1B2, or 1A10 antibody or other dengue type 1, 2, 3 and/or 4 virus antibody; chimeric antibodies in which the Fc and/or FR and/or CDR1 and/or CDR2 and/or light chain CDR3 regions of the 1A5 antibody, or the 2H7, 2H5, 3A2, 1B2, or 1A10 antibody or other dengue type 1, 2, 3 and/or 4 virus antibody, have been replaced by homologous human or non-human sequences; chimeric-$F(ab')_2$ fragment antibodies in which the FR and/or CDR1 and/or CDR and/or light chain CDR3 regions of the 1A5 antibody, or the 2H7, 2H5, 3A2, 1B2, or 1A10 antibody or other dengue type 1, 2, 3 and/or 4 virus antibody, have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. Thus, those skilled in the art may alter the 1A5 antibody, or the 2H7, 2H5, 3A2, 1B2, or 1A10 antibody or other dengue type 1, 2, 3 and/or 4 virus antibody, by the construction of CDR grafted or chimeric antibodies or antibody fragments containing all, or part thereof, of the disclosed heavy and light chain V-region CDR aa sequences (Jones, P. T. et al. 1986. *Nature* 321:522; Verhoeyen, M. et al. 1988 *Science* 39:1534; and Tempest, P. R. et al. 1991 *Bio/Technology* 9:266), without destroying the specificity of the antibodies for the dengue type 1, 2, 3 and/or 4 virus epitope. Such CDR grafted or chimeric antibodies or antibody fragments can be effective in prevention and treatment of dengue infection in animals (e.g. cattle) and man.

In preferred embodiments, the chimeric antibodies of the invention are fully human or humanized chimpanzee monoclonal antibodies including at least the heavy chain CDR3 region of the 1A5 antibody, or the 2H7, 2H5, 3A2, 1B2, or 1A10 antibody or other dengue type 1, 2, 3 and/or 4 virus antibody. As noted above, such chimeric antibodies may be produced in which some or all of the FR regions of the 1A5 antibody, or the 2H7, 2H5, 3A2, 1B2, or 1A10 antibody or other dengue type 1, 2, 3 and/or 4 virus antibody, have been replaced by other homologous human FR regions. In addition, the Fc portions may be replaced so as to produce IgA or IgM as well as IgG antibodies bearing some or all of the CDRs of the 1A5 antibody, or the 2H7, 2H5, 3A2, 1B2, or 1A10 antibody or other dengue type 1, 2, 3 and/or 4 virus antibody. Of particular importance is the inclusion of the heavy chain CDR3 region and, to a lesser extent, the other CDRs of the 1A5 antibody, or the 2H7, 2H5, 3A2, 1B2, or 1A10 antibody or other dengue type 1, 2, 3 and/or 4 virus antibody. Such fully human or humanized chimpanzee monoclonal antibodies will have particular utility in that they will not evoke an immune response against the antibody itself.

It is also possible, in accordance with the present invention, to produce chimeric antibodies including non-human sequences. Thus, one may use, for example, murine, ovine, equine, bovine or other mammalian Fc or FR sequences to replace some or all of the Fc or FR regions of the 1A5 antibody, or the 2H7, 2H5, 3A2, 1B2, or 1A10 antibody or other dengue type 1, 2, 3 and/or 4 virus antibody. Some of the CDRs may be replaced as well. Again, however, it is preferred that at least the heavy chain CDR3 of the 1A5 antibody, or the 2H7, 2H5, 3A2, 1B2, or 1A10 antibody or other dengue type 1, 2, 3 and/or 4 virus antibody, be included in such chimeric antibodies and, to a lesser extent, it is also preferred that some or all of the other CDRs of the 1A5 antibody, or the 2H7, 2H5, 3A2, 1B2, or 1A10 antibody or other dengue type 1, 2, 3 and/or 4 virus antibody, be included. Such chimeric antibodies bearing non-human immunoglobulin sequences admixed with the CDRs of the 1A5 antibody, or the 2H7, 2H5, 3A2, 1B2, or 1A10 antibody or other dengue type 1, 2, 3 and/or 4 virus antibody, are not preferred for use in humans and are particularly not preferred for extended use because they may evoke an immune response against the non-human sequences. They may, of course, be used for brief periods or in immunosuppressed individuals but, again, fully human or humanized chimpanzee monoclonal antibodies are preferred. Because such antibodies may be used for brief periods or in immunosuppressed subjects, chimeric antibodies bearing non-human mammalian Fc and FR sequences but including at least the heavy chain CDR3 of the 1A5 antibody, or the 2H7, 2H5, 3A2, 1B2, or 1A10 antibody or other dengue type 1, 2, 3 and/or 4 virus antibody, are contemplated as alternative embodiments of the present invention.

For inoculation or prophylactic uses, the antibodies of the present invention are preferably full-length antibody molecules including the Fc region. Such full-length antibodies will have longer half-lives than smaller fragment antibodies (e.g. Fab) and are more suitable for intravenous, intraperitoneal, intramuscular, intracavity, subcutaneous, or transdermal administration.

In some embodiments, Fab fragments, including chimeric Fab fragments, are preferred. Fabs offer several advantages over F(ab')$_2$ and whole immunoglobulin molecules for this therapeutic modality. First, because Fabs have only one binding site for their cognate antigen, the formation of immune complexes is precluded whereas such complexes can be generated when bivalent F(ab')$_2$ s and whole immunoglobulin molecules encounter their target antigen. This is of some importance because immune complex deposition in tissues can produce adverse inflammatory reactions. Second, because Fabs lack an Fc region they cannot trigger adverse inflammatory reactions that are activated by Fc, such as activation of the complement cascade. Third, the tissue penetration of the small Fab molecule is likely to be much better than that of the larger whole antibody. Fourth, Fabs can be produced easily and inexpensively in bacteria, such as *E. coli*, whereas whole immunoglobulin antibody molecules require mammalian cells for their production in useful amounts. The latter entails transfection of immunoglobulin sequences into mammalian cells with resultant transformation. Amplification of these sequences must then be achieved by rigorous selective procedures and stable transformants must be identified and maintained. The whole immunoglobulin molecules must be produced by stably transformed, high expression mammalian cells in culture with the attendant problems of serum-containing culture medium. In contrast, production of Fabs in *E. coli* eliminates these difficulties and makes it possible to produce these antibody fragments in large fermenters which are less expensive than cell culture-derived products.

In addition to Fabs, smaller antibody fragments and epitope-binding peptides having binding specificity for the epitope defined by the 1A5 antibody, or the 2H7, 2H5, 3A2, 1B2, or 1A10 antibody or other dengue type 1, 2, 3 and/or 4 virus antibody, are also contemplated by the present invention and can also be used to bind or neutralize the virus. For example, single chain antibodies can be constructed according to the method of U.S. Pat. No. 4,946,778, to Ladner et al. Single chain antibodies comprise the variable regions of the light and heavy chains joined by a flexible linker moiety. Yet smaller is the antibody fragment known as the single domain antibody or Fd, which comprises an isolated VH single domain. Techniques for obtaining a single domain antibody with at least some of the binding specificity of the full-length antibody from which they are derived are known in the art.

It is possible to determine, without undue experimentation, if an altered or chimeric antibody has the same specificity as the antibody of the 1A5 antibody, or the 2H7, 2H5, 3A2, 1B2, or 1A10 antibody or other dengue type 1, 2, 3 and/or 4 virus antibody, of the invention by ascertaining whether the former blocks the latter from binding to dengue type 1, 2, 3 and/or 4 virus. If the monoclonal antibody being tested competes with the 1A5 antibody, or the 2H7, 2H5, 3A2, 1B2, or 1A10 antibody or other dengue type 1, 2, 3 and/or 4 virus antibody, as shown by a decrease in binding of the 1A5 antibody, or the 2H7, 2H5, 3A2, 1B2, or 1A10 antibody or other dengue type 1, 2, 3 and/or 4 virus antibody, then it is likely that the two monoclonal antibodies bind to the same, or a closely spaced, epitope. Still another way to determine whether a monoclonal antibody has the specificity of the 1A5 antibody, or the 2H7, 2H5, 3A2, 1B2, or 1A10 antibody or other dengue type 1, 2, 3 and/or 4 virus antibody, of the invention is to pre-incubate the 1A5 antibody, or the 2H7, 2H5, 3A2, 1B2, or 1A10 antibody or other dengue type 1, 2, 3 and/or 4 virus antibody, with dengue type 1, 2, 3 and/or 4 virus with which it is normally reactive, and then add the monoclonal antibody being tested to determine if the monoclonal antibody being tested is inhibited in its ability to bind dengue type 1, 2, 3 and/or 4 virus. If the monoclonal antibody being tested is inhibited then, in all likelihood, it has the same, or a functionally equivalent, epitope and specificity as the 1A5 antibody, or the 2H7, 2H5, 3A2, 1B2, or 1A10 antibody or other dengue type 1, 2, 3 and/or 4 virus antibody, of the invention. Screening of monoclonal antibodies of the invention also can be carried out utilizing dengue type 1, 2, 3 and/or 4 virus and determining whether the monoclonal antibody neutralizes dengue type 1, 2, 3 and/or 4 virus.

By using the antibodies of the invention, it is now possible to produce anti-idiotypic antibodies which can be used to screen other monoclonal antibodies to identify whether the antibody has the same binding specificity as an antibody of the invention. In addition, such antiidiotypic antibodies can be used for active immunization (Herlyn, D. et al. 1986 *Science* 232:100). Such anti-idiotypic antibodies can be produced using well-known hybridoma techniques (Kohler, G. and Milstein, C. 1975 *Nature* 256:495). An anti-idiotypic antibody is an antibody which recognizes unique determinants present on the monoclonal antibody produced by the cell line of interest. These determinants are located in the hypervariable region of the antibody. It is this region which binds to a given epitope and, thus, is responsible for the specificity of the antibody.

An anti-idiotypic antibody can be prepared by immunizing an animal with the monoclonal antibody of interest. The immunized animal will recognize and respond to the idiotypic determinants of the immunizing antibody and produce an antibody to these idiotypic determinants. By using the anti-idiotypic antibodies of the immunized animal, which are specific for the monoclonal antibodies of the invention, it is possible to identify other clones with the same idiotype as the antibody of the hybridoma used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity.

It is also possible to use the anti-idiotype technology to produce monoclonal antibodies which mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

Nucleic Acids Encoding Anti-Dengue Virus Antibodies

Given the disclosure herein of the amino acid sequences of the heavy chain Fd and light chain variable domains of the 1A5 antibody, or the 2H7, 2H5, 3A2, 1B2, or 1A10 antibody or other dengue type 1, 2, 3 and/or 4 virus, one of ordinary skill in the art is now enabled to produce nucleic acids which encode this antibody or which encode the various fragment antibodies or chimeric antibodies described above. It is contemplated that such nucleic acids will be operably joined to other nucleic acids forming a recombinant vector for cloning or for expression of the antibodies of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the immunoglobulin V-regions of the 1A5 antibody, or the 2H7, 2H5, 3A2, 1B2, or 1A10 antibody or other dengue type 1, 2, 3 and/or 4 virus antibody, including framework and CDRs or parts thereof, and a suitable promoter either with (Whittle, N. et al. 1987 *Protein Eng.* 1:499 and Burton, D. R. et al. 1994 *Science* 266:1024) or without (Marasco, W. A. et al. 1993 *Proc. Natl. Acad, Sci.* (*USA*) 90:7889 and Duan, L. et al. 1994 *Proc. Natl. Acad, Sci.* (*USA*) 91:5075) a signal sequence for export or secretion. Such vectors may be transformed or transfected into prokaryotic (Huse, W. D. et al. 1989 *Science* 246:1275; Ward, S. et al. 1989 *Nature* 341:544; Marks, J. D. et al. 1991 *J. Mol. Biol.* 222:581; and Barbas, C. F. et al. 1991 *Proc. Natl. Acad. Sci.* (*USA*) 88:7987) or eukaryotic (Whittle, N. et al. 1987 *Protein Eng.* 1:499 and Burton, D. R. et al. 1994 *Science* 266:1024) cells or used for gene therapy (Marasco, W. A. et al. 1993 *Proc. Natl. Acad, Sci.* (*USA*) 90:7889 and Duan, L. et al. 1994 *Proc. Natl. Acad, Sci.* (*USA*) 91:5075) by conventional techniques, known to those with skill in the art.

The expression vectors of the present invention include regulatory sequences operably joined to a nucleotide sequence encoding one of the antibodies of the invention. As used herein, the term "regulatory sequences" means nucleotide sequences which are necessary for or conducive to the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the antibodies may be accomplished by any of a variety of standard means known in the art.

A preferred vector for screening monoclonal antibodies, but not necessarily preferred for the mass production of the antibodies of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic, regulatory sequences. Such vectors can be constructed by those with skill in the art and have been described by Smith, G. P. et al. (1985 *Science* 228:1315); Clackson, T. et al. (1991 *Nature* 352:624); Kang et al. (1991 in "Methods: A Companion to Methods in Enzymology: Vol. 2"; R. A. Lerner and D. R. Burton, ed. Academic Press, NY, pp 111-118); Barbas, C. F. et al. (1991 *Proc, Natl. Acad. Sci,* (*USA*) 88:7978), Roberts, B. L. et al. (1992 *Proc. Natl. Acad. Sci.* (*USA*) 89:2429).

A fusion polypeptide may be useful for purification of the antibodies of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein to the membrane of the host cell, such as the periplasmic membrane of Gram-negative bacteria. A preferred secretion signal for *E. coli* is a pelB secretion signal. The leader sequence of the pelB protein has previously been used as a secretion signal for fusion proteins (Better, M. et al. 1988 *Science* 240:1041; Sastry, L. et al. 1989 *Proc, Natl. Acad. Sci* (*USA*) 86:5728; and Mullinax, R. L. et al., 1990 *Proc. Natl. Acad. Sci.* (*USA*) 87:8095). Amino acid residue sequences for other secretion signal polypeptide domains from *E. coli* useful in this invention can be found in Neidhard, F. C. (ed.), 1987 *Escherichia coli and Salmonella Typhimurium: Typhimurium Cellular and Molecular Biology*, American Society for Microbiology, Washington, D.C.

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine et al. 1975 *Nature*

254:34). The sequence, which is called the Shine-Dalgarno (SD) sequence, is complementary to the 3' end of *E. coli* 16S rRNA. Binding of the ribosome to mRNA and the sequence at the 3' end of the mRNA can be affected by several factors: the degree of complementarity between the SD sequence and 3' end of the 16S rRNA; the spacing lying between the SD sequence and the AUG; and the nucleotide sequence following the AUG, which affects ribosome binding. The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extrachromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColEI found in pBR322 and a variety of other common plasmids. Also preferred is the p15A origin of replication found on pACYC and its derivatives. The ColEI and p15A replicons have been extensively utilized in molecular biology, are available on a variety of plasmids and are described by Sambrook. et al. 1989 *Molecular Cloning: A Laboratory Manual,* 2nd edition, Cold Spring Harbor Laboratory Press.

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as those commercially available from suppliers such as Invitrogen, (San Diego, Calif.).

When the antibodies of the invention include both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the full-length antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a di-cistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The antibodies of the present invention may additionally, of course, be produced by eukaryotic cells such as CHO cells, human or mouse hybridomas, immortalized B-lymphoblastoid cells, and the like. In this case, a vector is constructed in which eukaryotic regulatory sequences are operably joined to the nucleotide sequences encoding the antibody polypeptide or polypeptides. The design and selection of an appropriate eukaryotic vector is within the ability and discretion of one of ordinary skill in the art. The subsequent purification of the antibodies may be accomplished by any of a variety of standard means known in the art.

The antibodies of the present invention may furthermore, of course, be produced in plants. In 1989, Hiatt et al. 1989 *Nature* 342:76 first demonstrated that functional antibodies could be produced in transgenic plants. Since then, a considerable amount of effort has been invested in developing plants for antibody (or "plantibody") production (for reviews see Giddings, G. et al., 2000 *Nat Biotechnol* 18:1151; Fischer, R. and Emans, N., 2000, *Transgenic Res* 9:279). Recombinant antibodies can be targeted to seeds, tubers, or fruits, making administration of antibodies in such plant tissues advantageous for immunization programs in developing countries and worldwide.

In another embodiment, the present invention provides host cells, both prokaryotic and eukaryotic, transformed or transfected with, and therefore including, the vectors of the present invention.

Diagnostic and Pharmaceutical Anti-Dengue Virus Antibody Preparations

The invention also relates to a method for preparing diagnostic or pharmaceutical compositions comprising the monoclonal antibodies of the invention or polynucleotide sequences encoding the antibodies of the invention or part thereof, the pharmaceutical compositions being used for immunoprophylaxis or immunotherapy of dengue virus disease. The pharmaceutical preparation includes a pharmaceutically acceptable carrier. Such carriers, as used herein, means a non-toxic material that does not interfere with the effectiveness of the biological activity of the active ingredients. The term "physiologically acceptable" refers to a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

A preferred embodiment of the invention relates to monoclonal antibodies whose heavy chains comprise in CDR3 the polypeptide having SEQ ID NO: 103, and/or whose light chains comprise in CDR3 the polypeptide having SEQ ID NO: 111; whose heavy chains comprise in CDR3 the polypeptide having SEQ ID NO: 119, and/or whose light chains comprise in CDR3 the polypeptide having SEQ ID NO: 127; whose heavy chains comprise in CDR3 the polypeptide having SEQ ID NO: 135, and/or whose light chains comprise in CDR3 the polypeptide having SEQ ID NO: 143; whose heavy chains comprise in CDR3 the polypeptide having SEQ ID NO: 151, and/or whose light chains comprise in CDR3 the polypeptide having SEQ ID NO: 159; whose heavy chains comprise in CDR3 the polypeptide having SEQ ID NO: 167, and/or whose light chains comprise in CDR3 the polypeptide having SEQ ID NO: 175; whose heavy chains comprise in CDR3 the polypeptide having SEQ ID NO: 183, and/or whose light chains comprise in CDR3 the polypeptide having SEQ ID NO: 191; and conservative variations of these peptides. Also encompassed by the present invention are certain amino acid sequences that bind to epitopic sequences in E of dengue type 1, 2, 3 and/or 4 virus and that confer neutralization of dengue type 1, 2, 3 and/or 4 virus when bound thereto. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies having the substituted polypeptide also bind or neutralize dengue type 1, 2, 3 and/or 4 virus. Analogously, another preferred embodiment of the invention relates to polynucleotides which encode the above noted heavy chain polypeptides and to polynucleotide sequences which are complementary to these polynucleotide sequences. Complementary polynucleotide sequences include those sequences that hybridize to the polynucleotide sequences of the invention under stringent hybridization conditions.

The anti-dengue type 1, 2, 3 and/or 4 virus antibodies of the invention may be labeled by a variety of means for use in diagnostic and/or pharmaceutical applications. There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

Another labeling technique which may result in greater sensitivity consists of coupling the antibodies to low molecular weight haptens. These haptens can then be specifically altered by means of a second reaction. For example, it is common to use haptens such as biotin, which reacts with avidin, or dinitrophenol, pyridoxal, or fluorescein, which can react with specific antihapten antibodies.

The materials for use in the assay of the invention are ideally suited for the preparation of a kit. Such a kit may comprise a carrier means being compartmentalized to receive in close confinement one or more container means such as vials, tubes, and the like, each of the container means comprising one of the separate elements to be used in the method. For example, one of the container means may comprise a monoclonal antibody of the invention that is, or can be, detectably labeled. The kit may also have containers containing buffer(s) and/or a container comprising a reporter-means, such as a biotin-binding protein, such as avidin or streptavidin, bound to a reporter molecule, such as an enzymatic or fluorescent label.

In Vitro Detection and Diagnostics

The monoclonal antibodies of the invention are suited for in vitro use, for example, in immunoassays in which they can be utilized in liquid phase or bound to a solid phase carrier. In addition, the monoclonal antibodies in these immunoassays can be detectably labeled in various ways. Examples of types of immunoassays which can utilize the monoclonal antibodies of the invention are competitive and non-competitive immunoassays in either a direct or indirect format. Examples of such immunoassays are the radioimmunoassay (RIA) and the sandwich (immunometric) assay. Detection of antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of dengue type 1, 2, 3 and/or 4 virus. Examples of well-known carriers include glass, polystyrene, polypropylene, polyethylene, dextran, nylon, amylase, natural and modified cellulose, polyacrylamide, agarose and magnetite. The nature of the carrier can be either soluble or insoluble for purposes of the invention. Those skilled in the art will know of other suitable carriers for binding monoclonal antibodies, or will be able to ascertain such, using routine experimentation.

For purposes of the invention, dengue type 1, 2, 3 and/or 4 virus may be detected by the monoclonal antibodies of the invention when present in biological fluids and tissues. Any sample containing a detectable amount of dengue type 1, 2, 3 and/or 4 virus can be used. A sample can be a liquid such as urine, saliva, cerebrospinal fluid, blood, serum or the like; a solid or semi-solid such as tissues, feces, or the like; or, alternatively, a solid tissue such as those commonly used in histological diagnosis.

In Vivo Detection of Dengue Virus

In using the monoclonal antibodies of the invention for the in vivo detection of antigen, the detectably labeled monoclonal antibody is given in a dose which is diagnostically effective. The term "diagnostically effective" means that the amount of detectably labeled monoclonal antibody is administered in sufficient quantity to enable detection of the site having the dengue type 1, 2, 3 and/or 4 virus antigen for which the monoclonal antibodies are specific.

The concentration of detectably labeled monoclonal antibody which is administered should be sufficient such that the binding to dengue type 1, 2, 3 and/or 4 virus is detectable compared to the background. Further, it is desirable that the detectably labeled monoclonal antibody be rapidly cleared from the circulatory system in order to give the best target-to-background signal ratio.

As a rule, the dosage of detectably labeled monoclonal antibody for in vivo diagnosis will vary depending on such factors as age, sex, and extent of disease of the individual. The dosage of monoclonal antibody can vary from about 0.01 mg/kg to about 50 mg/kg, preferably 0.1 mg/kg to about 20 mg/kg, most preferably about 0.1 mg/kg to about 2 mg/kg. Such dosages may vary, for example, depending on whether multiple injections are given, on the tissue being assayed, and other factors known to those of skill in the art.

For in vivo diagnostic imaging, the type of detection instrument available is a major factor in selecting an appropriate radioisotope. The radioisotope chosen must have a type of decay which is detectable for the given type of instrument. Still another important factor in selecting a radioisotope for in vivo diagnosis is that the half-life of the radioisotope be long enough such that it is still detectable at the time of maximum uptake by the target, but short enough such that deleterious radiation with respect to the host is acceptable. Ideally, a radioisotope used for in vivo imaging will lack a particle emission but produce a large number of photons in the 140-250 keV range, which may be readily detected by conventional gamma cameras.

For in vivo diagnosis, radioisotopes may be bound to immunoglobulin either directly or indirectly by using an intermediate functional group. Intermediate functional groups which often are used to bind radioisotopes which exist as metallic ions are the bifunctional chelating agents such as diethylenetriaminepentacetic acid (DTPA) and ethylenediaminetetra-acetic acid (EDTA) and similar molecules. Typical examples of metallic ions which can be bound to the monoclonal antibodies of the invention are $^{111}$In, $^{97}$Ru, $^{67}$Ga, $^{68}$Ga, $^{72}$As, $^{89}$Zr and $^{201}$Tl.

The monoclonal antibodies of the invention can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually gamma and positron emitting radioisotopes are used for camera imaging and paramagnetic isotopes for MRI. Elements which are particularly useful in such techniques include $^{157}$Gd, $^{55}$Mn, $^{162}$Dy, $^{52}$Cr and $^{56}$Fe.

The monoclonal antibodies of the invention can be used in vitro and in vivo to monitor the course of dengue virus disease therapy. Thus, for example, by measuring the increase or decrease in the number of cells infected with dengue type 1, 2, 3 and/or 4 virus or changes in the concentration of dengue type 1, 2, 3 and/or 4 virus present in the body or in various body fluids, it would be possible to determine whether a particular therapeutic regimen aimed at ameliorating dengue virus disease is effective.

Prophylaxis and Therapy of Dengue Virus Disease

The monoclonal antibodies can also be used in prophylaxis and as therapy for dengue virus disease in humans. The terms, "prophylaxis" and "therapy" as used herein in conjunction with the monoclonal antibodies of the invention denote both prophylactic as well as therapeutic administration and both passive immunization with substantially purified polypeptide products, as well as gene therapy by transfer of polynucleotide sequences encoding the product or part thereof. Thus, the monoclonal antibodies can be administered to high-risk subjects in order to lessen the likelihood and/or severity of dengue virus disease or administered to subjects already evidencing active dengue virus infection. In the present invention, Fab fragments also bind or neutralize dengue type 1, 2, 3 and/or 4 virus and therefore may be used to treat dengue virus infection but full-length antibody molecules are otherwise preferred.

As used herein, a "prophylactically effective amount" of the monoclonal antibodies of the invention is a dosage large enough to produce the desired effect in the protection of individuals against dengue virus infection for a reasonable period of time, such as one to two months or longer following administration. A prophylactically effective amount is not, however, a dosage so large as to cause adverse side effects, such as hyperviscosity syndromes, pulmonary edema, congestive heart failure, and the like. Generally, a prophylactically effective amount may vary with the subject's age, condition, and sex, as well as the extent of the disease in the subject and can be determined by one of skill in the art. The dosage of the prophylactically effective amount may be adjusted by the individual physician or veterinarian in the event of any complication. A prophylactically effective amount may vary from about 0.01 mg/kg to about 50 mg/kg, preferably from about 0.1 mg/kg to about 20 mg/kg, most preferably from about 0.2 mg/kg to about 2 mg/kg, in one or more administrations (priming and boosting).

As used herein, a "therapeutically effective amount" of the monoclonal antibodies of the invention is a dosage large enough to produce the desired effect in which the symptoms of dengue virus disease are ameliorated or the likelihood of infection is decreased. A therapeutically effective amount is not, however, a dosage so large as to cause adverse side effects, such as hyperviscosity syndromes, pulmonary edema, congestive heart failure, and the like. Generally, a therapeutically effective amount may vary with the subject's age, condition, and sex, as well as the extent of the disease in the subject and can be determined by one of skill in the art. The dosage of the therapeutically effective amount may be adjusted by the individual physician or veterinarian in the event of any complication. A therapeutically effective amount may vary from about 0.01 mg/kg to about 50 mg/kg, preferably from about 0.1 mg/kg to about 20 mg/kg, most preferably from about 0.2 mg/kg to about 2 mg/kg, in one or more dose administrations daily, for one or several days. Preferred is administration of the antibody for 2 to 5 or more consecutive days in order to avoid "rebound" of virus replication from occurring.

The monoclonal antibodies of the invention can be administered by injection or by gradual infusion over time. The administration of the monoclonal antibodies of the invention may, for example, be intravenous, intraperitoneal, intramuscular, intracavity, subcutaneous, or transdermal. Techniques for preparing injectate or infusate delivery systems containing antibodies are well known to those of skill in the art. Generally, such systems should utilize components which will not significantly impair the biological properties of the antibodies, such as the paratope binding capacity (see, for example, *Remington's Pharmaceutical Sciences*, 18*th edition*, 1990, Mack Publishing). Those of skill in the art can readily determine the various parameters and conditions for producing antibody injectates or infusates without resort to undue experimentation.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and the like.

Monoclonal Antibodies that Bind or Neutralize Dengue Type 1, 2, 3 and/or 4 Viruses The four dengue virus serotypes (DENV-1 to DENV-4) and several other arthropod-borne flaviviruses, including tick-borne encephalitis virus (TBEV), and yellow fever virus (YFV), Japanese encephalitis virus (JEV), St. Louis encephalitis virus (SLEV) and West Nile virus (WNV) are important human pathogens. Currently, dengue viruses are the most important in terms of morbidity and geographic distribution (Gubler, D. J. 1998 Clin. Microbiol. Rev. 11:480-496; Monath, T. P. 1994 Proc. Natl. Acad. Sci. USA 91:2395-2400). Patients with dengue usually develop fever, rash, and joint pain, and the disease is self-limited. Occasionally, more severe forms of disease, known as dengue hemorrhagic fever and dengue hemorrhagic shock syndrome (DHF/DSS), also occur especially in the dengue endemic regions of Southeast Asia and more recently of Central and South America. It is estimated that 50-100 million dengue infections and several hundred thousand cases of DHF occur every year. Aedes aegypti and A. albopictus mosquitoes are the principal vectors for human-to-human transmission of dengue viruses. Control of dengue epidemics by spraying of insecticides to reduce the vector mosquito population has proven to be rather ineffective. Aedes mosquito species are also responsible for transmission of WNV, which emerged for the first time in New York in 1999 (Lanciotti, R. S. et al. 1999 Science 286:2333-2337). Since that time the virus has spread widely to most of the continental U. S. There were several thousand reported WNV infections with mortality of two hundred in 2002 (O'Leary, D. R. et al. 2004 Vector Borne Zoonotic Dis. 4:61-70). Prevention of WNV infections has become an important public health issue in the U. S. and many other countries.

Dengue infection is thought to induce a life-long immunity against the same serotype of virus. Cross-protection against other dengue virus serotypes (heterotypic immunity) in humans is brief, lasting only 2-9 months (Sabin, A. B. 1952. Am. J. Trop. Med. Hyg. 1:30-50). Concurrent or sequential infections with different dengue virus serotypes are common (Gubler, D. J. et al. 1985 Am. J. Trop. Med. Hyg. 34:170-173; Laille, M. et al. 1991 J. Med. Virol. 34:51-54; Wang, W. K. et al. 2003 J. Microbiol. Immunol. Infect. 36:89-95). Epidemiological data suggest that a subsequent infection with a dengue virus serotype different from the serotype of the previous infection is more frequently associated with severe dengue illness than is the primary dengue infection. This observation has led to the hypothesis that immunopathological mechanisms involving the activities of dengue virus-specific antibodies or cytotoxic T cells contribute to dengue severity (Halstead, S. B. 1979 J. Inf. Dis. 140:527-533; Halstead, S. B. 1988 Science 239:476-481). However, evidence also indicates that dengue virulence could be in part due to a virus factor, such as replication capacity (Rosen, L. 1996 Bull. Soc. Pathol. Exot. 89:91-3; discussion 93-94; Wang, W. K. et al. 2003 Virology 305:330-338). In order to better protect against dengue infection and to minimize the risk of severe dengue, the current immunization strategy favors the use of a tetravalent vaccine against all four dengue serotypes. However, development of a safe and effective vaccine against dengue has been elusive.

Previously, we described an alternative strategy for the prevention of dengue fever by passive immunization with humanized antibodies. Repertoire cloning was employed to identify Fab antibody fragments from chimpanzees infected with all four dengue virus serotypes. One of these Fabs, 5H2, efficiently neutralized DENV-4 and was subsequently converted to a full-length IgG antibody containing human IgG sequences. Humanized antibody IgG 5H2 was produced in mammalian CHO cells and shown to neutralize DENV-4 at a 50% plaque reduction ($PRNT_{50}$) titer of 0.03-0.05 µg/ml by a plaque reduction neutralization test (PRNT). This success prompted us to employ the phage library constructed from the chimpanzee infected with multiple dengue virus serotypes in an effort to recover Fab fragments against the other three dengue virus serotypes. In this study, we describe identification of Fab fragments that are broadly cross-reactive with all four dengue viruses as well as with other major insect-borne flaviviruses. Several of these Fabs were shown to cross-neutralize DENV-1 and DENV-2 at a similar high titer and DENV-3 or DENV-4 at a reduced titer. A full-length humanized IgG1 antibody, designated IgG 1A5, was produced by combining Fab 1A5 with human IgG1 sequences. Humanized IgG1 1A5 antibody, like Fab 1A5, efficiently neutralized DENV-1 and DENV-2, but less efficiently neutralized DENV-3 and DENV-4 as well as other flaviviruses.

Inoculation of Chimpanzees with Multiple Dengue Virus Serotypes and Preparation of Lymphocytes from Bone Marrow.

As described previously, two chimpanzees (#1616 and #1618) that had been intra-hepatically transfected with infectious RNA transcripts of a full-length DENV-4 cDNA clone were infected subcutaneously (sc) nine-and-half months later with a mixture of DENV-1 (Western Pacific strain), DENV-2 (New Guinea C strain, prototype) and DENV-3 (strain H87), each at $10^6$ plaque forming units (pfu), diluted in minimal essential medium (MEM) plus 0.25% human serum albumin. Twelve weeks after infection with the multiple dengue virus serotypes, bone marrow was aspirated from each chimpanzee and the lymphocytes were prepared by centrifugation on a Ficoll-Paque gradient.

Construction of γ1/κ Chimpanzee Fab Antibody Library.

Repertoire cloning of chimpanzee Fab fragments was described earlier. Briefly, approximately $3 \times 10^7$ bone marrow lymphocytes from chimpanzee 1618, which developed higher neutralizing antibody titers against DENV-1, DENV-2 and DENV-3 than did chimpanzee #1616, were used for phage library construction. Total RNA from lymphocytes was extracted using the RNA Extraction kit (Stratagene, La Jolla, Calif.) and reverse-transcribed with oligo dT as primer using the ThermoScript RT-PCR system (Invitrogen). Chimpanzee $V_L$-$C_L$ DNA sequences were amplified by PCR using seven pairs of human κ light chain family-specific primers and a constant domain 3' primer using AmpliTaq DNA polymerase (Perkin Elmers) (Barbas, C. F. et al. 1991 Proc. Natl. Acad. Sci. USA 88:7978-7982; Glamann, J. et al. 1998 J. Virol. 72:585-592; Persson, M. A. et al. 1991 Proc. Natl. Acad. Sci. USA 88:2432-6; Schofield, D. J. et al. 2000 J. Virol. 74:5548-55). Chimpanzee $V_H$-$C_{H1}$ DNA sequences were similarly amplified using nine human γ1 heavy chain family-specific 5' primers and a chimpanzee γ1 specific 3' primer across the constant domain 1-hinge junction (Glamann, J. et al. 1998 J. Virol. 72:585-592; Schofield, D. J. et al. 2000 J. Virol. 74:5548-55).

Pooled κ light chain DNA fragments were digested with SacI and XbaI and then cloned into the pComb 3H vector by electroporation of electrocompetent E. coli XL-1 Blue (Stratagene). The recombinant plasmid was used for cloning of the pooled γ1 heavy chain DNA fragments at the XhoI and SpeI sites. A library size of $2-4 \times 10^8$ colonies of transformed E. coli was obtained at each cloning.

Preparation of Dengue Viruses from Infected Mosquito C6/36 Cells.

Mosquito C6/36 cells were grown in MEM supplemented with 10% fetal bovine serum (FBS) plus gentamycin and fungizone. Confluent cells were infected with DENV-1, DENV-2, DENV-3 or DENV-4 of the strain indicated above, each at 0.1 multiple of infection (moi) in MEM containing 2% FBS. DENV-1, prototype Hawaii strain, and DENV-2, New Guinea B strain, were also used. Infected cells were placed in serum-free medium (VP-SFM, Gibco Corp) one day after infection and incubated at 28° C. The culture medium was harvested on days 6, 8, and 10 after infection and fresh serum-free medium was added after each harvest. The virus titer in the medium was determined by a focus assay on Vero cells and the medium was kept refrigerated for use as panning antigen and for ELISA and neutralization assays.

Preparation of WNV/DENV-4 Chimera, JEV, and LGTV.

Vero cells were grown in MEM supplemented with 10% FBS plus gentamycin and fungizone at 37° C. Confluent Vero cell monolayers were infected with 1 moi of Langat virus strain TP 21 (LGTV) or WNV/DENV-4 chimera, and the infected cells were placed in MEM containing 2% fetal calf serum. JEV vaccine strain SA14-14-2 was also propagated in Vero cells. The culture medium was harvested 7 days after infection and titered by focus assay on Vero cells. For use as ELISA antigens, LGTV, JEV and WNV/DENV-4 were grown in serum-free medium as described above. For neutralization assays, each of the above virus stocks was prepared in MEM containing 20% FBS and frozen until use.

Panning of Phage Library Using DENV-1l DENV-2 or DENV-3 as Antigens.

The pComb H DNA library that contained the $V_L$-$C_L$ and $V_H$-$C_{H1}$ inserts constructed earlier was again used for phage preparation. Identification of Fabs that were recovered from separate pannings against DENV-1, DENV-2 or DENV-3 was performed as described earlier. Briefly, a bacterial culture greater than $2 \times 10^8$ diversity prepared by transformation with the plasmid DNA library was infected with VSC M13 helper phage (Stratagene) at 50 moi to generate a phage display library. The phage library was panned by affinity binding on DENV-1, DENV-2, or DENV-3 virions captured by chimpanzee dengue virus-convalescent sera coated on the wells of an ELISA plate. Following three cycles of panning, the selected phage was used for infection of E. coli XL-1 to produce phagemid DNA. Phagemid DNA was cleaved with SpeI and NheI to remove the phage gene III segment and circularized prior to use for transformation of E coli XL-1. E. coli colonies were screened by ELISA to identify clones that yielded soluble Fab fragments reactive with DENV-1, DENV-2 or DENV-3.

DNA Sequencing of Dengue Virus-specific Fab Clones.

Plasmid from selected E. coli clones producing soluble Fabs was first analyzed by digestion with BstN1 to identify clones with distinct cleavage patterns. Sequence analysis of the $V_H$ and $V_L$ DNA inserts was performed on an automated DNA sequencer using a Taq fluorescent dideoxynucleotide terminator cycle sequencing kit. The following primers were used: 5' ACAGCTATCGCGATTGCAGTG (SEQ ID NO: 193) and 5' CACCTGATCCTCAGATGGCGG (SEQ ID NO: 194) for sequencing the $V_L$ segments; 5' ATTGCCTACG-GCAGCCGCTGG (SEQ ID NO: 195) and 5' GGAAG-TAGTCCTTGACCAGGC (SEQ ID NO: 196) for sequencing the $V_H$ segments. Software Vector NTi Suite 7.0 (InforMax) was used for analysis of the sequences. The DNA-PLOT software program (MRC Center for Protein Engineering) was used for a homologous sequence search of the human IgG variable segments in the data bank.

Fab Production and Purification

Selected E. coli clones were grown in 2 liters of L-broth containing 1% glucose and 100 µg/ml ampicillin and 10 µg/ml tetracycline to an early log phase at 30° C. The bacteria were pelleted and resuspended in 2 liters of L-broth containing ampicillin and tetracycline plus 0.1 mM inducer isopropyl-β-D-thiogalactopyranoside (IPTG) for growth at 30° C. for 4-5 hr (Glamann, J. et al. 1998 J. Virol. 72:585-592; Schofield, D. J. et al 2000 J. Virol. 74:5548-55). After induction, the bacteria were collected and resuspended in 40 ml of buffer containing 50 mM phosphate buffer, pH 8.0, 10 mM Tris-HCl, 100 mM NaCl, and 0.1 mM protease inhibitor 4-(2-aminoethyl)-benzene sulfonyl fluoride (AEBSF). After three cycles of freezing and thawing to release the soluble Fab product from the bacterial periplasm, clear supernatant was prepared by centrifugation at 12,000 rpm in a Beckman JA-20 rotor for 60 min. The histidine-tagged Fab was affinity-purified through a column of TALON Metal Affinity Resin (Clontech). The purity of the Fab preparation was verified by polyacrylamide gel electrophoresis and the Fab concentration determined by ELISA using human IgG F(ab')$_2$ (Cappel) as a protein weight standard.

Biotinylation of Purified Fab Fragments and Competition ELISA.

Purified Fab was biotinylated with EZ-Link NHS-LC-Biotin (Pierce) as suggested by the supplier. After extensive dialysis against PBS, the biotin-labeled Fab was analyzed for binding to DENV-1 or DENV-2 coated on wells of a microtiter plate. For competition ELISA, a fixed concentration of biotin-labeled Fab was mixed with the crude or purified preparation of competing Fabs in serial dilutions. The mixture was added to DENV-1 or DENV-2 coated wells and incubated at 37° C. After washing, streptavidin-alkaline phophatase (Pierce) was added for detection of biotinylated Fab reactive to DENV-1 or DENV-2 as described previously.

Western Blot Analysis.

Virus samples were prepared by mixing approximately $10^5$ pfu of each virus with an equal volume of 2x sample buffer containing 2% SDS, 20% glycerol, 20 nM Tris-HCl, pH 8.0 and 0.03% bromophenol blue. The sample was loaded on SDS-polyacrylamide gel and separated by electrophoresis. The gel was blotted on a nitrocellulose membrane, treated with 5% skim milk, reacted with Fab 1A5 and then with a 1/1000 dilution of goat anti-human IgG-horseradish peroxides (Pierce). The blot was developed with Sigma fast 3,3'-diaminobenzidine (Sigma-Aldrich).

Measurement of Neutralizing Activity of Chimpanzee Fab Fragments.

Purified Fab antibodies were used in PRNT to determine the neutralizing titer against each of the four dengue virus serotypes. Typically, approximately 50 pfu of the dengue virus in 100 µl of MEM was mixed with the same volume of the Fab in serial dilution. The dengue virus-Fab antibody mixture was incubated at 37° C. for 1 h and then 100 µl of the mixture was added to confluent Vero cells in a 24-well plate in duplicate. After an 1-h adsorption period at 37° C., an overlay of MEM containing 2% FCS and 1% Tragacanth gum was added and the plates were placed in a 5% $CO_2$-incubator at 37° C. for 3-4 days. Virus foci that formed on the cell monolayer were immuno-stained (Okuno, Y. et al. 1985 Arch. Virol. 86:129-135). The $PRNT_{50}$ titer in µg/ml was calculated. Neutralization of the BSL-3 flaviviruses TBEV, JEV and WNV was performed with attenuated BSL-2 variants LGTV, the JEV strain SA 14-14-2 and the WNV/DENV-4 chimera, which contains the WNV preM-E structure protein genes on the DENV-4 backbone.

Construction of Recombinant Plasmid and Expression of Whole IgG1 Molecules in CHO Cells.

The pFab CMV-dhfr vector for full-length IgG1 expression was constructed from plasmid pFab CMV originally obtained from P. Sanna (Scripps Research Institute) (Sanna, P. P. et al. 1999 *Immunotechnology* 4:185-8). A di-hydrofolate reductase gene (dhfr) along with the transcription signals was inserted at the unique Not I site as a selecting marker and for gene copy amplification. In addition, an A to G substitution at the last nucleotide position of the intron that preceded the $C_H3$ exon present in the original vector was made to enable full-length IgG1 expression. Fabs 2H7, 1A5, 3A2, and 1B2 were selected for conversion to whole IgG1 antibodies for analysis of their neutralizing activity. The $V_L$ DNA segment of each Fab was inserted into the expression vector at the SacI and XbaI sites. The $V_H$ DNA segment of the Fab, regenerated by PCR, was then added at the XhoI and SpeI sites. The chimpanzee-specific sequences in the hinge region were converted to the human sequence as described previously.

Production of whole IgG molecules in CHO/dhfr-cells (ATCC) was carried out by transfection with RsrII-linearized plasmid in the presence of Lipofectamine (Gibco). Two days after transfection, cells in a T25 flask were re-plated in Iscove's Modified Dulbecco Medium supplemented with 10% FBS plus $10^{-7}$ M methotrexate (MTX) in the absence of hypoxanthine/thymidine as selecting medium (Dorai, H., and G. P. Moore. 1987 *J. Immunol.* 139:4232-4241; Wood, C. R. et al. 1990 *J. Immunol.* 145:3011-6). Colonies of CHO cells resistant to $2\times10^{-7}$ M MTX appeared approximately two weeks after transfection. The transformed CHO cells secreting IgG1 in the medium were identified following cloning in a 96- or 24-well plate. To produce IgG1, the selected CHO cells were adapted to grow in CHO CD medium. The culture medium was concentrated and the IgG1 product was purified through a protein-A affinity column (Pierce). The apparent affinity constant (Kd) for the binding of the IgG to each of the four dengue virus serotypes was calculated as the antibody concentrations that gave 50% maximum binding by ELISA (Lin, C.-W. and S.-C. Wu 2003 *J. Virol.* 77:2600-2606; Moore, J. P. et al 1995 *J. Virol.* 69:101-109).

Chimpanzee Antibody Library and Identification of Fabs Recovered by Panning with DENV-1, DENV-2 or DENV-3.

As described earlier, two chimpanzees (#1616 and #1618) that had been intra-hepatically transfected with infectious DENV-4 RNA were infected with a mixture of DENV-1, DENV-2 and DENV-3 nine-and-half months later. Each of the chimpanzees developed moderate to high $PRNT_{50}$ titers of antibodies against DENV-1, DENV-2 and DENV-3. The $PRNT_{50}$ titer against DENV-4 also increased appreciably after secondary dengue infection. Chimpanzee 1618 developed slightly higher neutralizing antibody titers against DENV-1, DENV-2 and DENV-3 than did chimpanzee 1616. Previously, we constructed a phage library from bone marrow mRNA of chimpanzee 1618 and identified DENV-4 and dengue-complex specific Fabs following panning of the library against DENV-4. Based on this experience, we reasoned initially that separate panning of the phage library using DENV-1, DENV-2 or DENV-3 would yield dengue type, sub-complex or complex-specific Fab clones that could be further analyzed for their capacity to neutralize DENV-1, DENV-2 or DENV-3 in vitro.

(a) Fabs recovered from panning against DENV-1. Several Fab clones with distinct BstN1 digestion patterns were recovered following panning with DENV-1. PRNT against DENV-1 was carried out to identify the most promising neutralizing Fab antibodies. Fab clones that did not neutralize DENV-1 or only poorly neutralized it, were not studied further. Table 5 shows that Fab 2H7 and Fab 2H5 efficiently neutralized DENV-1 at a $PRNT_{50}$ titer of 0.26 and 0.47 µg/ml, respectively. Unexpectedly, each of these Fabs also neutralized DENV-2 at a titer similar to that detected for DENV-1. The $PRNT_{50}$ titer of these Fabs against DENV-3 or DENV-4 was reduced by 20 fold or more. Fab 2H5 and Fab 2H7 shared similar sequences (see below), but Fab 2H5 neutralized all four dengue viruses at lower titers than did Fab 2H7. Fab 2H5 was therefore not studied further.

(b) Fabs recovered from panning against DENV-2. Three distinct neutralizing Fabs, i.e., 1A5, 1A10, and 1B2, were identified in this experiment (Table 5). Like Fab 2H7 and Fab 2H5 identified above, Fab 1A5 efficiently neutralized both DENV-1 and DENV-2 at a similar $PRNT_{50}$ of 0.49 and 0.77 µg/ml, respectively, and also neutralized DENV-3 and DENV-4, but at a lower titer. Fab 1B2 and Fab 1A10 neutralized DENV-1 more efficiently than DENV-2 and much more efficiently than DENV-3 or DENV-4.

(c) Fabs recovered from panning against DENV-3. A large number of Fab clones showing a distinct BstN1 digestion pattern were recovered from the library by panning against DENV-3. Fab 3A2 neutralized DENV-1 and DENV-2 at a titer of 0.37 and 1.33 µg/ml, respectively and also efficiently neutralized DENV-3 at a $PRNT_{50}$ titer of 3.0 µg/ml (Table 5). The ability of Fabs to cross-neutralize DENV-1 and DENV-2 at a similar high titer was a novel characteristic of several monoclonal antibodies, regardless of the dengue virus serotype used as the panning antigen.

Analysis of $V_H$ and $V_L$ Sequences.

The amino acid sequences in the $V_L$ and $V_H$ segment of six selected Fab antibodies are shown in FIGS. 6A and 6B. Fabs 2H7, 2H5, 1A5 and 3A2 were closely related, as an identical or nearly identical sequence was present in various framework segments or complementarity determining regions (CDR's) of the light chain or the heavy chain. Nevertheless, minor sequence variations (two or more amino acids) among them were present in other regions of the heavy chain as well as some regions of the light chain. These Fabs contained an identical or nearly identical 16-amino acid sequence, which included two cysteines in the CDR3-H domain principally involved in antigen binding. The sequences of Fab 1B2 and Fab 1A10 were distinct and contained a CDR3-H sequence different from those of Fabs 2H7, 1A5 and 3 . Table 6 shows the result of a homologous sequence search of human IgG germ line gene segments most related to the $V_H$ or $V_L$ segments of the selected six chimpanzee Fabs. The germ line origin was the same for Fab 2H7, 2H5, 1A5, or 3A2 and the homology with the most related human sequence was 82-94%, excluding the CDR3-H and CDR3-L regions.

The $V_H$ and $V_L$ sequences of these Fab antibodies were also compared with the corresponding sequence of the Fab antibodies previously recovered by panning with DENV-4. Interestingly, Fab 1A10 and Fab 3E4 shared an identical $V_H$ sequence with the exception of two amino acids: one in the FR1 region and the other in the CDR3 region (FIG. 6B). These two Fabs, however, differed appreciably in various regions of the $V_L$ sequence (FIG. 6A). While the neutralizing activity of Fab 3E4 against DENV-1 and DENV-2 was low (titer greater than 42 µg/ml), Fab 1A10 neutralized DENV-1 and DENV-2 at a titer of 0.94 and 5.26 µg/ml, respectively.

Antigen Specificity of Chimpanzee Fabs.

Soluble Fabs were analyzed for binding activity to each of the four dengue virus serotypes by ELISA. Table 7 shows that each of these Fabs was broadly cross-reactive for all four dengue serotypes and had a similar high binding titer. Surprisingly, none of the Fab antibodies recovered from panning with DENV-1, DENV-2 or DENV-3 reacted in a dengue type-specific manner.

Figure 7:
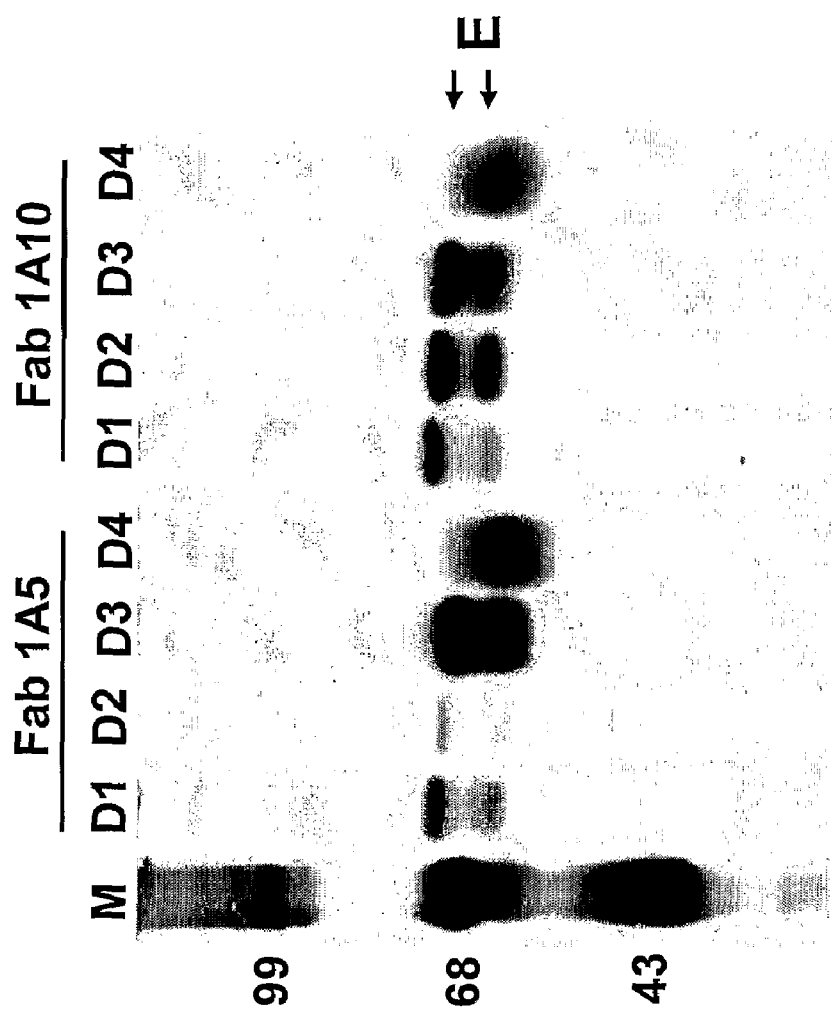
FIG. 7. Analysis of antigen specificity by radio-immuno-precipitation. Radioactive $^{35}$S-methionine-labeled lysates separately prepared from Vero cells infected with each of the dengue virus serotypes (D1 to D4) were used for immune precipitation with Fab 1A5 or Fab 1A10. M shows the protein markers with molecular weight in kD on the left. Each of the Fabs precipitated the E protein of each of four dengue virus serotypes. Note that the E protein often migrated as a doublet or a broad band probably resulting from differences in glycosylation.

Radio-immunoprecipitation was performed to determine the antigen binding specificity for each of the Fabs using a radio-labeled lysate of Vero cells infected with DENV-1, DENV-2, DENV-3 or DENV-4. FIG. 7 shows a typical autoradiogram of the immune precipitate separated by polyacrylamide gel electrophoresis. Fab 1A5 and Fab 1A10 specifically precipitated the E protein, migrating as a doublet, of each of the four dengue viruses. Fabs 2H7, 3A2 and 1B2 also precipitated E from the lysate of each of the four dengue virus serotypes.

Analysis of Chimpanzee Fabs Binding to DENV-1 or DENV-2 by Competition ELISA.

Figure 8:
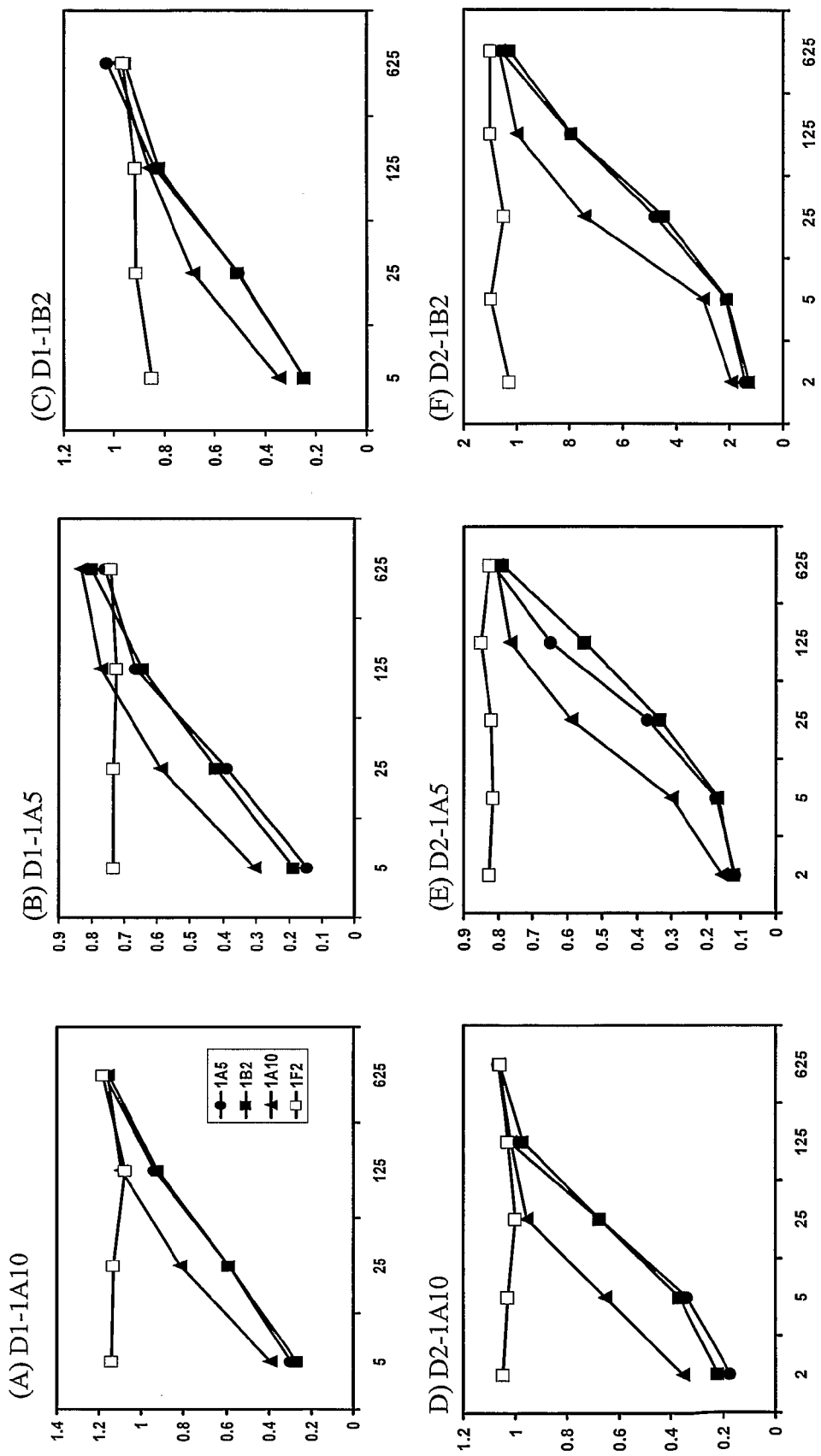
FIG. 8A-F. Analysis of Fab binding to DENV-1 or DENV-2. Fabs 1A5, 1B2 and 1A10 were affinity-purified, biotinylated and used for analysis of binding activity to DENV-1 or DENV-2 virus by competition ELISA in the presence of competing, unlabeled Fabs. Chimpanzee Fab 1F2, which did not react with any of the dengue viruses, was used as a negative control. The numbers on the Y axis are OD readings and the X coordinates represent reciprocal dilutions of the competing Fabs. D1 or D2 (top of each panel) indicates DENV-1 or DENV-2 used. The insert inside panel A shows the symbol for each Fab and the symbols are the same for all six panels.

Fabs 1A5, 2H7 and 3A2 shared an identical or nearly identical CDR3-H sequence, whereas Fab 1A10 and Fab 1B2 each contained a distinct CDR3-H sequence. The relatedness of the binding sites for Fabs 1A5, 1A10 and 1B2 on DENV-1 or DENV-2 was analyzed by competition ELISA. Surprising, binding of affinity-purified, biotinylated Fab 1A10 to DENV-1 was competed by the unlabeled crude preparation of Fab 1B2 and Fab 1A5 (FIG. 8A). Similarly, binding of biotinylated Fab 1A5 to DENV-1 was competed by Fab 1B2 and Fab 1A10 and binding of Fab 1B2 was competed by Fab 1A5 and Fab 1A10 (FIG. 8B and 8C). When DENV-2 was tested, the binding competition patterns among these three Fabs were essentially identical to that seen with DENV-1 (FIG. 8D, 8E, and 8F). As a control, chimpanzee Fab 1F2, which did not bind either DENV-1 or DENV-2, failed to compete any of the labeled Fabs. Thus, the site that was occupied by Fab 1A5 overlapped with the site occupied by Fab 1B2 and Fab 1A10 on DENV-1, and on DENV-2 E. The Fab 1A5 binding site (epitope) on the DENV-2 E protein was mapped in a separate study (see herein).

Cross-reactivity of Chimpanzee Fabs to WNV and Other Flaviviruses.

Figure 9:
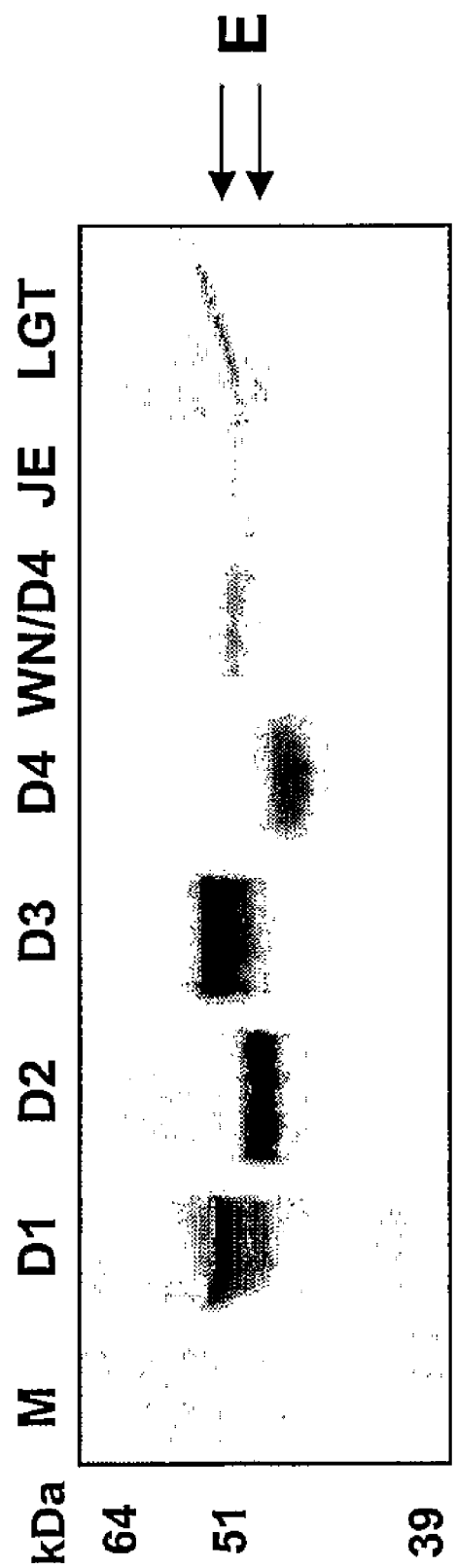
FIG. 9. Binding of Fab 1A5 to dengue viruses and other flaviviruses as measured by Western blotting. Approximately $10^5$ pfu of each virus was applied and separated by polyacrylamide gel electrophoresis. Gel lanes are: D1, DENV-1 strain Hawaii; D2, DENV-2 strain New Guinea B; D3, DENV-3 strain H87; D4, DENV-4 strain 814669; WN/D4, WNV/DENV-4 chimera; JE, JEV strain SA 14-14-2; LGT, LGTV strain TP 21. The position of the E protein is indicated. Molecular size markers are shown on the left.

In the course of this study, we found that the Fabs recovered in this study also reacted with the WNV/DENV-4 chimera at a high titer as detected by ELISA. Fab 1A5 was selected for analysis of binding to the four dengue viruses and other major flaviviruses. Western blot analysis (FIG. 9) showed that Fab 1A5 reacted relatively strongly with each of the four dengue viruses and WNV/DENV-4. By comparison, Fab 1A5 bound weakly to JEV SA14-14-2 and LGTV TP 21. The reduced binding activity of Fab1A5 to the JEV SA14-14-2 and LGTV TP21 reflected the low $PRNT_{50}$ titer (greater than 70 µg/ml) of Fab 1A5 against these two viruses. Interestingly, Fab 1A5 neutralized WNV/DENV-4 chimera at a $PRNT_{50}$ titer of 4.8 µg/ml, similar to that measured for DENV-3 and DENV-4.

Production and Characterization of Full-length Humanized IgG1 Antibodies.

Figure 10:
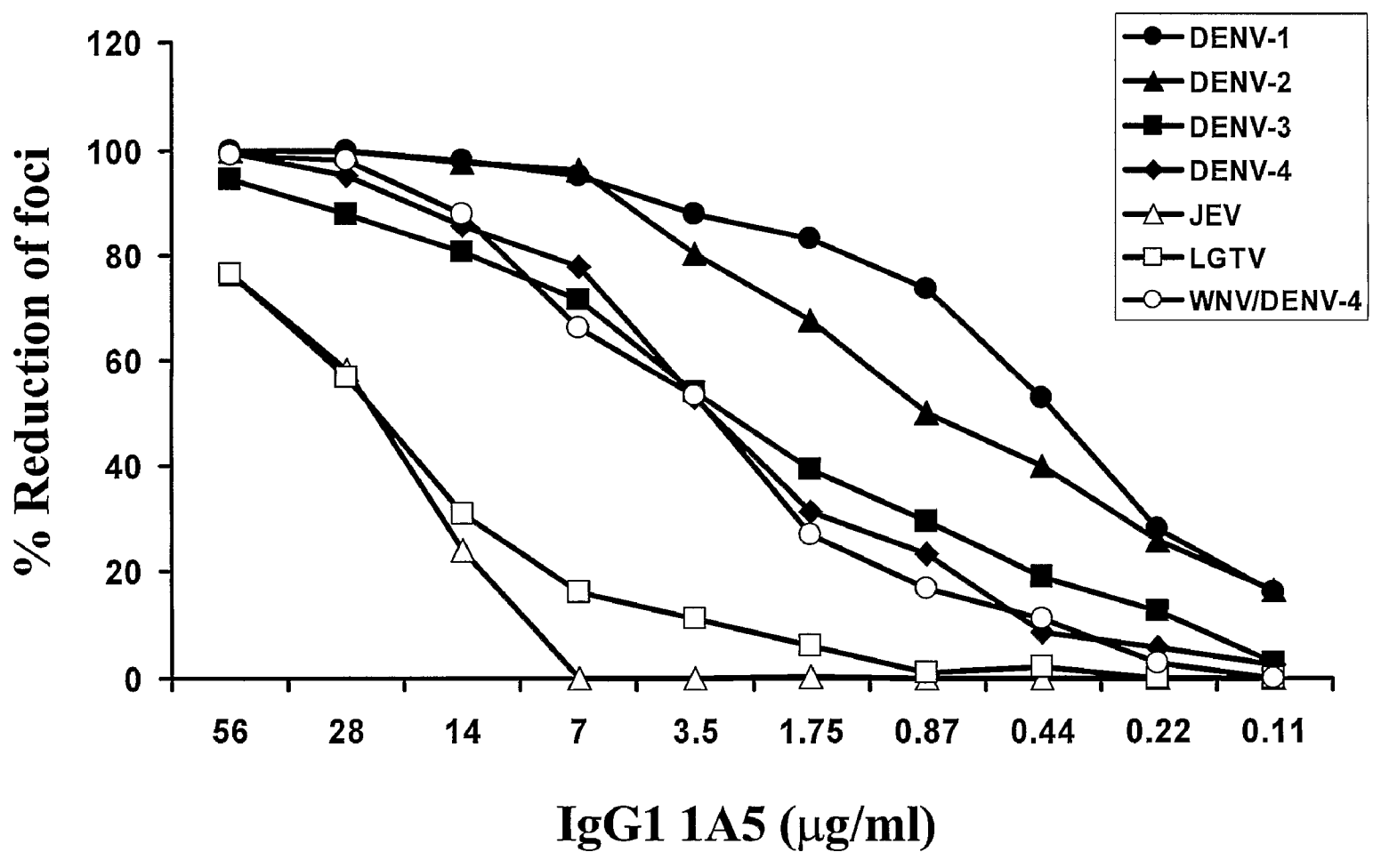

With the exception of Fab 1A10, the Fab fragments were each converted to the full-length IgG1 antibody in combination with the human IgG1 sequence using the expression vector pFab CMV-dhfr for transformation of CHO cells. Among these antibodies, IgG1 1A5 was produced in the highest yield, approximately 2 µg/$10^6$ cells per day in the medium of the transformed CHO cells. IgG1 1A5 was selected to determine the $PRNT_{50}$ against each of the four dengue viruses (FIG. 10). IgG1 1A5 neutralized DENV-1 and DENV-2 at a $PRNT_{50}$ titer of 0.48 and 0.95 µg/ml, respectively. IgG1 1A5 also neutralized DENV-3 and DENV-4 at a $PRNT_{50}$ titer of 3.2 and 4.3 µg/ml, respectively. The apparent affinity constants determined by ELISA, termed ELSA Kd, were calculated at 0.50, 0.60, 0.67 and 0.82 nM for DENV-1, DENV-2, DENV-3 and DENV-4, respectively, in the same decreasing order as the $PRNT_{50}$ titers against these viruses. Humanized IgG1 1A5 was also tested for neutralization of WNV/DENV-4, JEV strain SA14-14-2 and LGT strain TP21 by PRNT. The $PRNT_{50}$ titer against WNV/DENV-4 was -3.8 µg/ml, whereas the $PRNT_{50}$ titer against JEV strain SA14-14-2 and LGTV strain TP21 was 21 and 28 µg/ml, respectively (FIG. 10).

TABLE 5

Dengue virus cross-neutralizing activities of Fabs identified by panning against DENV-1, DENV-2, or DENV-3

| Fab | Panning antigen | $PRNT_{50}$ titer (µg/ml) aganist | | | |
|---|---|---|---|---|---|
| | | DENV-1 | DENV-2 | DENV-3 | DENV-4 |
| 2H7 | DENV-1 | 0.26 | 0.33 | 5.92 | 7.26 |
| 2H5 | DENV-1 | 0.47 | 0.53 | 20.8 | 9.26 |
| 1A5 | DENV-2 | 0.49 | 0.77 | 3.49 | 4.23 |
| 1A10 | DENV-2 | 0.94 | 5.26 | 26.3 | 12.6 |
| 1B2 | DENV-2 | 0.50 | 3.13 | >100 | 29.2 |
| 3A2 | DENV-3 | 0.37 | 1.33 | 2.99 | 4.71 |
| 3E4* | DENV-4 | 42.7 | >100 | >100 | 40.5 |

Fabs which are underlined shared a similar VH sequence or VL sequence.
*Fab 3E4 was recovered from the chimpanzee after primary infection by panning against DENV-4 as described previously. Fab 3E4 was included for comparison with Fab 1A10.

TABLE 6

Sequence similarity between chimpanzee Fab antibodies and their most related human immunoglobulin homologs.

| Chimp. Fab | $V_H$ vs. Human Family (gene) | homology % identity | Ref. cited | $V_L$ vs. Human Family (gene) | homology % Identity | Ref. cited |
|---|---|---|---|---|---|---|
| 2H7 | VH3 (8-1B) | 84 | 1 | VKI (DPK9) | 90 | 4 |
| 2H5 | VH3 (8-1B) | 85 | 1 | VKI (DPK9) | 86 | 4 |
| 3A2 | VH3 (8-1B) | 82 | 1 | VKI (DPK9) | 86 | 4 |
| 1A5 | VH3 (8-1B) | 85 | 1 | VKI (DPK9) | 86 | 4 |
| 1B2 | VH4 (DP-78) | 87 | 2 | VKI (Va) | 94 | 5 |
| 1A10 | VH1 (dp-10) | 86 | 3 | VKII (A2b) | 85 | 6 |

The DNAPLOT program was used to search for the most homologous sequence of human germ-line IgG genes in the data base. Percent amino acid identity in the VH or VL segment excluding the CDR-3 region is indicated.
1 Berman et al. 1988 EMBO J. 7: 727-738.
2 Chothia et al. 1992 J. Mol. Biol. 227: 799-817.
3 Schofield et al. 2000 J. Virol. 74: 5548-55.
4 Cox et al. 1994 Eur. J. Immunol. 24: 827-836.
5. Ogata et al. 1993 Proc. Natl. Acad. Sci. USA 90: 3014-3018.
6. Engle et al. 2003 J. Virol. 77: 12941-12949.

TABLE 7

Binding activities of Fab monoclonal antibodies to each of the four dengue virus serotypes as determined by ELISA

| | ELISA titer of Fab binding to | | | |
|---|---|---|---|---|
| Fab | DENV-1 | DENV-2 | DENV-3 | DENV-4 |
| 1A5 | 4.1 | 3.8 | 3.8 | 3.8 |
| 3A2 | 4.1 | 3.8 | 3.8 | 3.8 |
| 2H7 | 4.1 | 3.8 | 3.6 | 3.8 |
| 1B2 | 3.9 | 3.8 | 3.8 | 3.8 |
| 1A10 | 4.1 | 3.8 | 3.6 | 3.8 |
| 5H2 | <1.0 | <1.0 | <1.0 | 3.8 |
| 3E4 | 4.0 | 3.8 | 3.6 | 3.8 |
| 1F2* | <1.0 | <1.0 | <1.0 | <1.0 |

Microtiter plates were coated with DENV-1, DENV-2, DENV-3 or DENV-4 virions. Data are presented as log10 of the reciprocal dilution that gave an OD reading 2 fold or higher than the background. Dengue virus cross-reactive Fab 3E4 and DENV-4 specific Fab 5H2 were described previously. The starting concentration of each Fab was approximately 140 µg/ml.
*Chimpanzee Fab 1F2 was used as negative control.

Epitope of Monoclonal Antibody That Neutralizes Dengue Type 1 and Type 2 Viruses The epitope determinants of chimpanzee Fab antibody 1A5, which had been shown to be broadly reactive to flaviviruses and efficient for cross-neutralization of dengue type 1 and type 2 viruses (DENV-1 and DENV-2), were studied by analysis of DENV-2 antigenic variants. Sequence analysis showed that one antigenic variant contained a Gly-to-Val substitution at position 106 within the flavivirus-conserved fusion peptide loop of the envelope protein (E) and another variant contained a His-to-Gln substitution at position 317 in E. Substitution of $Gly_{106}Val$ in DENV-2 E reduced the binding affinity of Fab 1A5 by approximately 80 fold, whereas substitution of $His_{317}Gln$ had little or no effect on antibody binding as compared to the parental virus. Treatment of DENV-2 with β-mercaptoethanol abolished binding of Fab 1A5, indicating that disulfide bridges were required for the structural integrity of the Fab 1A5 epitope. Binding of Fab 1A5 to DENV-2 was competed by an oligopeptide containing the fusion peptide sequence as shown by competition ELISA. Both DENV-2 antigenic variants were shown to be attenuated or at least similar to the parental virus, when evaluated for growth in cultured cells or for neurovirulence in mice. Fab 1A5 inhibited low pH-induced membrane fusion of mosquito C6/36 cells infected with DENV-1 or DENV-2, as detected by reduced syncytium formation. Both substitutions in DENV-2 E lowered the pH threshold for membrane fusion, as measured by fusion-from-within assay. In the 3-D structure of E, $Gly_{106}$ in domain II and $His_{317}$ in domain II of the opposite E monomer were spatially close. From the locations of these amino acids, Fab 1A5 is concluded to recognize a novel epitope that has not been mapped before with a flavivirus monoclonal antibody.

Introduction.

The flavivirus genome contains a positive strand RNA with one open reading frame coding for a polyprotein. The polyprotein is processed to produce the three structural proteins, i.e., the capsid (C), precursor membrane (prM) and envelope (E) proteins, plus seven nonstructural proteins, designated as NS1, NS2A, NS2B, NS3, NS4A, NS4B and NS5. The E protein is responsible for viral attachment to the putative cell surface receptor(s), fusion with the endosomal membranes upon entry, and mediating protective immune responses in the infected host. Mouse monoclonal antibodies against the E proteins of most major flaviviruses have been identified (Heinz, F. X. 1986 Adv. Virus Res. 31:103-168; Roehrig, J. T. 2003 Adv. Virus Res. 59:141-175). Studies using these monoclonal antibodies have allowed identification of flavivirus group-, complex- and type-specific epitopes on the flavivirus E proteins. With few exceptions, neutralizing monoclonal antibodies are flavivirus type- or subtype-specific, consistent with the flavivirus classification determined with the polyclonal sera (Calisher, C. H. et al. 1989 J. Gen. Virol. 70:37-43).

The 3-D structure of the flat homodimeric E glycoprotein that is organized in a direction parallel to the viral membrane has been determined for TBEV (Rey, F. A. et al. 1995 Nature 375:291-298) and DENV-2 (Modis, Y. et al. 2003 Proc. Natl. Acad. Sci. USA 100:6986-6991). The E subunit, approximately 500 amino acids in length, is folded into three structurally distinct domains, termed domains I, II and III. Domain I organizes the entire E structure and contains a flavivirus-conserved glycosylated asparagine. Domain II is folded into an elongated structure containing at its distal end the fusion peptide sequence, commonly called the fusion loop, which is conserved among the flaviviruses. The outward glycan unit in domain I protrudes to cover the fusion loop of the other subunit. There is an extensive interface contact between domain II and each of the three domains of the neighboring subunit. Domain III is an immunoglobulin-like region and lies at the end of the subunit. The dimeric E structure realigns to become trimeric when triggered by lowering the pH, while the three domains remain intact structurally (Bressanelli, S. et al. 2004 EMBO. J. 23:728-738; Modis, Y. et al. 2004 Nature 427:313-319). During the transition, the fusion loop becomes exposed and re-oriented outward, making it available for membrane contact.

Antigenic determinants of flavivirus cross-reactive antibodies have been mapped to domain II, whereas determinants of subtype- and type-specific antibodies have been assigned to domains I and III (Heinz, F. X. 1986 Adv. Virus Res. 31:103-168; Mandl, C. W. et al. 1989 J. Virol. 63:564-571; Roehrig, J. T. 2003 Adv. Virus Res. 59:141-175; Roehrig, J. T. et al. 1998 Virology 246:317-328). Most epitopes of neutralizing antibodies have been placed on the outer surface of the E glycoprotein, consistent with their accessibility to antibody binding. Mutations present in variant viruses that have escaped neutralization by antibodies blocking virus adsorption to Vero cells have been assigned to the lateral side of E in domain III (Crill, W. D., and J. T. Roehrig 2001 J. Virol 75:7769-7773). Similarly, the mutations of antigenic variants that affect mouse neurovirulence have been mapped to this domain (Cecilia, D., and E. A. Gould 1991 Virology 181:70-77; Holzmann, H. et al. 1997 J. Gen. Virol. 78:31-37; Jiang, W. R. et al. 1993 J. Gen. Virol. 74:931-935). These findings have suggested that the sequence in domain III may mediate viral attachment to the receptor on susceptible cells.

The antigenic model of flavivirus E proteins established thus far from studies with the large repertoire of mouse monoclonal antibodies has provided much information about serological specificities and functional activities (Heinz, F. X. 1986 Adv. Virus Res. 31:103-168; Roehrig, J. T. 2003 Adv. Virus Res. 59:141-175). The question remains whether these antigenic epitopes are mouse-specific or whether in fact, they represent immuno-dominant sites on E recognized by the immune systems of other host species as well. Unfortunately, there is a lack of flavivirus monoclonal antibodies from other host species, especially higher primates or humans.

We have recently turned to the identification of chimpanzee Fab fragments by repertoire cloning and construction of full-length humanized IgG antibodies in an effort to develop a passive immunization strategy for prevention of dengue virus infection. We have described a DENV-4 specific chimpanzee Fab fragment and a derived full-length humanized IgG antibody highly efficient for neutralization of DENV-4. We have also identified chimpanzee Fab fragments, including 1A5, that exhibited a broad cross-reactivity to members of the flavivirus group and cross-neutralized DENV-1 and DENV-2 efficiently. The current study describes mapping the epitope determinants of Fab 1A5 by analysis of DENV-2 antigenic variants. A determinant critically involved in Fab 1A5 antibody binding and neutralization mapped to $Gly_{106}$ within the flavivirus-conserved fusion loop in domain II of E. Another determinant affecting antibody neutralization, but not antibody binding, mapped to $His_{317}$ in domain III of the neighboring E monomer. Amino acid substitutions in these DENV-2 variants lowered the pH threshold for membrane fusion of the infected cells. From the locations of these amino acids in the 3-D structure, the Fab 1A5 antibody is indicated to recognize a novel epitope on E.

Dengue Viruses and Cultured Cells.

Simian Vero cells and mosquito C6/36 cells were grown in minimum essential medium (MEM) plus 10% fetal bovine serum (FBS), 2 mM L-glutamine, 0.05 mg/ml gentamycin, and 2.5 units/ml fungizone. Mouse-adapted DENV-2 New Guinea B (NGB) and New Guinea C (NGC) strains were used for selection of antigenic variants. Stocks of the dengue viruses were prepared from infected C6/36 cells grown in VP-SFM medium (Invitrogen). The titers of these viruses were approximately $1 \times 10^7$ plaque-forming units (pfu)/ml, determined on Vero cell monolayers.

Antibodies.

Chimpanzee Fab 1A5 was identified by panning of a phage library using DENV-2 as described herein. Poly-histidine tagged Fab 1A5, expressed in *E. coli*, was affinity-purified using TALON affinity resin (Clontech). The concentration of Fab was determined colorimetrically using the BCA protein assay kit (Pierce). Hyper-immune mouse ascites fluid (HMAF) raised against DENV-2 and DENV-4 was purchased from American Type Culture Collection. Mouse monoclonal antibody Mab 3H5, specific to DENV-2, was kindly provided by R. Putnak (Hiramatsu, K. et al 1996 *Virology* 224:437-445).

Plaque Reduction Neutralization Test (PRNT).

Approximately 50 pfu of DENV-2, or other viruses to be tested, were mixed with Fab 1A5 serially diluted in 250 µl of MEM. The mixture was incubated at 37° C. for 1 h prior to use for infection of Vero cells or C6/36 cells in duplicate wells of a 24-well plate. Infected Vero cells were added with a medium overlay containing 1% gum tragacanth (Sigma) and incubated at 37° C. for 3 days. Infected C6/36 cells were overlaid with medium containing 0.8% methyl cellulose and incubated at 32° C. for 5 days. Foci of infected cells were visualized by immuno-staining, using HMAF and anti-mouse IgG peroxidase (Pierce). The Fab titer in µg/ml that produced 50% reduction of foci ($PRNT_{50}$) was calculated from at least 3 experiments.

Selection of DENV-2 Antigenic Variants.

Affinity-purified Fab 1A5 was used for selection of antigenic variants from mouse-passaged DENV-2 NGB and DENV-2 NGC, both of which had been previously sequenced in the C-prM-E region (Bray, M. et al. 1998 *J. Virol.* 72:1647-1651). Parental DENV-2 NGB or DENV-2 NGC, approximately $1 \times 10^7$ pfu, was mixed with Fab 1A5 at 25 µg/ml (equivalent to 100 $PRNT_{50}$ titers) in MEM and incubated at 37° C. for 1 h. The mixture was added to the Vero cell monolayer in a 35-mm culture plate for adsorption at 37° C. for 1 h. The monolayer was rinsed once with phosphate buffered saline (PBS), 3 ml of MEM containing 2% FBS plus 5 µg/ml of Fab 1A5 was added and then the cells were incubated at 37° C. for 7 days. Progeny virus in the culture medium was collected for neutralization with Fab 1A5, followed by infection of Vero cells again. The neutralization cycle was repeated and the Fab 1A5-resistance phenotype of progeny virus monitored. Fab 1A5-resistant variants were isolated by plaque-to-plaque purification three times on Vero cells prior to amplification in C6/36 cells in the absence of the antibody.

Sequence Analysis of Antigenic Variants.

Genomic RNA of each antigenic variant following amplification in C6/36 cells was extracted using Trizol solution (Life Technologies). Reverse transcription of RNA with primer AGTCTTGTTACTGAGCGGATTCC (SEQ ID NO: 198) at nucleotide positions 2587 to 2565 in DENV-2 NS1 was carried out using the Superscript kit (Life Technologies). Amplification of C-prM-E DNA with appropriate primers by PCR was performed, using AmpliTaq DNA polymerase (Perkin-Elmer). The DNA product was sequenced using primers spanning the DNA segment in an ABI sequencer (Perkin-Elmer, Applied Biosystems). The sequences of eight to ten plaque-purified isolates from each variant were analyzed. Sequence assembly was performed using Vector NTI Suite (InforMax). Structural modeling of the mutant E protein was performed using SwissModel and the crystal coordinates of DENV-2 (1OAN.pdb) as the template (Guex, N., and M. C. Peitsch 1997 *Electrophoresis* 18:2714-2723; Modis, Y. et al. 2003 *Proc. Natl. Acad. Sci. USA* 100:6986-6991). Swiss-Pdb Viewer was used for graphical development.

Construction of DENV-2/DENV-4 Chimeras.

Construction of chimeric cDNA containing the C-prM-E sequence of parental DENV-2 NGB, DENV-2 NGC or their antigenic variants on the DENV-4 background was as described (Bray, M., and C. J. Lai. 1991 *Proc. Natl. Acad. Sci. USA* 88:10342-10346). Briefly, parental or variant DENV-2 C-prM-E DNA was generated by reverse transcription of virion RNA and PCR amplification. The DNA product was digested with BglII and XhoI and then cloned into plasmid p5'-2, replacing the corresponding DENV-4 sequence. The ClaI-XhoI fragment of p5'-2 DNA containing the DENV-2 C-prM-E sequence was then used to replace the corresponding fragment of full-length DENV-4 DNA, generating full-length chimeric DENV-2/DENV-4 DNA. Confluent C6/36 cells were transfected with the RNA transcripts of the chimeric DENV-2/DENV-4 DNA construct as described (Bray, M., and C. J. Lai. 1991 *Proc. Natl. Acad. Sci. USA* 88:10342-10346; Lai, C. J. et al. 1991 *Proc. Natl. Acad. Sci. USA* 88:5139-5143). Three weeks after transfection, the culture medium had a titer greater than $10^6$ pfu/ml determined by focus assay on C6/36 cells. The C-prM-E DNA segment of progeny virus was prepared for sequence verification.

Construction of DENV-4 Variants.

Two silent mutations, A to C at nucleotide 378 and C to T at nucleotide 381 near the fusion loop encoding sequence in E, were first introduced to create a unique AgeI site in full-length DENV-4 DNA (Lai, C. J. et al. 1991 *Proc. Natl. Acad. Sci. USA* 88:5139-5143). Site-directed mutagenesis by PCR was performed using a forward primer GTTTGACAGCTTATCATCGATAAGC (SEQ ID NO: 199) corresponding to nucleotides 8-32 of pBR322 and a reverse primer containing the AgeI cleavage sequence and following nucleotide substitution(s) in E: G to C at nucleotide 310 and G to A at nucleotide 311 for generating $Gly_{104}His$ substitution; G to T at nucleotide 317 for $Gly_{106}Val$ substitution; and G to C at nucleotide 321 for Leu$_{107}$Phe substitution. The PCR products, digested with ClaI and AgeI, were each cloned into full-length DENV-4 DNA. RNA transcription and transfection of C6/36 cells and recovery of virus were performed as described above.

Polyacrylamide Gel Electrophoresis and Western Blotting.

Dengue virus was mixed with an equal volume of 2× sample buffer (2% SDS, 20% glycerol, 20 mM Tris-HCl, 0.02% bromophenol blue) with or without 0.5% β-mercaptoethanol. The virus mixture was boiled for 10 min prior to loading for separation by polyacrylamide gel electrophoresis. The protein gel was blot-transferred onto a nitrocellulose membrane electrophoretically. The protein blot was treated with 5% skim milk and reacted with Fab 1A5 or Mab 3H5 for 1 h. The blot was then washed with Tris-buffered saline containing 0.05% Tween 20 three times and reacted with goat anti-human IgG or anti-mouse IgG peroxidase (Pierce) at room temperature for 1 h. The protein blot was developed with Sigma fast™ 3,3'-diaminobenzidine (Sigma-Aldrich).

Antibody Binding Affinity Assay.

ELISA was performed to determine the binding affinity of Fab 1A5 to parental DENV-2 and its antigenic variants (Lin, C.-W. and S.-C. Wu. 2003 *J. Virol.* 77:2600-2606; Moore, J. P. 1995 *J. Virol.* 69:101-109; Raffai, R. et al. 2000 *J. Biol Chem.* 275:7109-7116). Briefly, Mab 3H5-coated wells of a microtiter plate were blocked with 3% bovine serum albumin and then each virus was added to separate wells. Following incubation at 37° C. for 1 h, affinity-purified Fab 1A5 in serial dilution was added and the plate incubated at 37° C. for 1 h. Fab 1A5 bound to DENV-2 on the microtiter plate was detected using goat anti-human IgG alkaline phosphatase (Sigma). The apparent affinity constant, termed ELISA Kd, was calculated for the Fab 1A5 concentration in nM that produced 50% of maximum binding.

Binding of Fab 1A5 to Oligopeptides.

Three oligopeptides were analyzed: control peptide 1, GAMHSALAGATEVD (SEQ ID NO: 200) and control peptide 2, WWWQTFDAR (SEQ ID NO: 201) (Thullier, P. 2001 *J. Gen. Virol.* 82:1885-1982); and fusion peptide, DRGWGNGSGLFGKGG (SEQ ID NO: 202). The control peptides contained sequences unrelated to the fusion sequence and the fusion peptide contained the entire fusion sequence with a Ser substitution for Cys. In a direct binding assay, each of the oligopeptides was coated on a 96-well microtiter plate at 5 μg/well in 0.1 M carbonate buffer, pH 9.6. After washing with PBS containing 0.05% Tween 20 and then blocking with PBS containing 3% bovine serum albumin (BSA), Fab 1A5 in PBS containing 1% BSA was added. Fab 1A5 bound to the oligopeptides was detected using goat anti-human IgG-alkaline phosphatase (Sigma). The competition binding assay was performed essentially as described (Thullier, P. 2001 *J. Gen. Virol.* 82:1885-1982). Briefly, purified Fab 1A5 at 0.05 jig/ml was pre-incubated with each of the oligopeptides in serial dilution at 37° C. for 2 h. The reaction mixture was added to the wells of a microtiter plate coated with 25 μl of DENV-2 at 10$^5$ pfu/ml in PBS plus 1% BSA. Fab 1A5 bound to DENV-2 was detected as described.

Plaque Morphology and Growth Analysis.

Vero cells in a 6-well plate were infected with parental DENV-2 NGB, DENV-2 NGC, or an antigenic variant and overlaid with medium containing 1% gum tragacanth. After incubation at 37° C. for 5 days, viral plaques were visualized by immuno-staining. The diameter of 20 plaques from each virus was measured on a digital image using Adobe Photoshop. For growth analysis, confluent monolayers of Vero cells or C6/36 cells in a 24-well plate were infected with each C6/36 cell-amplified virus at 0.01 multiplicity of infection (moi) in duplicate. Infected Vero cells were incubated at 37° C. and C6/36 cells at 32° C., and the culture medium was collected daily for 7 days. The virus sample was clarified by centrifugation and the titer determined by focus assay on Vero cells.

Mouse Neurovirulence.

Neurovirulence of parental DENV-2 NGB and its antigenic variants was evaluated in outbred Swiss mice. Three-day-old suckling mice, in groups of 8 to 11, were inoculated by the intracranial (ic) route with 100, 10, or 1 pfu of each virus in 20 μl MEM containing 0.25% human serum albumin. Inoculated mice were observed for symptoms of encephalitis, including ruffled hair, hunched back, paralysis and death. Paralyzed, moribund mice were euthanized and scored during the four-week observation period. Student's t-Test was used to compare the LD$_{50}$ in pfu between parental DENV-2 and its antigenic variants.

Fusion Activity Assay.

Fusion-from-within (FFWI) assays were performed for the DENV-2 parent and its antigenic variants as described (Randolph, V. B., and V. Stollar 1990 *J. Gen. Virol.* 71:1845-1850). C6/36 cell monolayers in a 24-well plate were infected with each virus at 0.2 moi in MEM plus 10% FBS, buffered with 10 mM 4-(2-hydroxyethyl)piperazine-1-ethanesulfonic acid (HEPES) at pH 7.7 and incubated at 32° C. Four to five days after infection, the infected cell monolayer was rinsed once with PBS and fusion medium (MEM plus 20 mM HEPES for pH 7.0 to 7.8 or 20 mM 2-morpholinoethanesulonic acid (MES) for pH 5.4 to 6.6 was added before incubation at 40° C. for 2 hr. The infected cells were stained using the Diff-Quik Stain Set (Dade Behring) and examined for syncytium formation microscopically. The fusion index defined as (1−[number of cells/number of nuclei]) was calculated by counting 300 nuclei for each virus in at least five microscopic fields. The percentage of infected cells was determined by immunofluorescence assay using HMAF. Fusion inhibition by Fab 1A5 was performed as described (Guirakhoo, F. et al. 1991 *J. Gen. Virol.* 72:1323-1329). In brief, DENV-1 or DENV-2 infected C6/36 cells were incubated with Fab 1A5 at 37° C. for 1 h prior to exposure to the low pH medium. Infected cells were also incubated with Mab 3H5 in parallel as the control.

Selection of DENV-2 Antigenic Variants Using Fab 1A5.

Mouse-adapted, neurovirulent DENV-2 NGB and DENV-2 NGC were used for selection of antigenic variants resistant to Fab 1A5 by neutralization in vitro. One DENV-2 NGB antigenic variant, designated as NGB-V1, was isolated after 8 cycles of neutralization and Vero cell passage. The PRNT$_{50}$ titer of NGB-V1 was 12.0 μg/ml, compared to that of parental DENV-2 NGB, which was 0.74 μg/ml (FIG. 11A). A second antigenic variant, designated NGB-V2, was isolated after 11 rounds of neutralization. NGB-V2 was completely resistant to neutralization by Fab 1A5 (>70 μg/ml). In parallel, selection of DENV-2 NGC variants of Fab 1A5 was also performed to provide additional information. This effort yielded one antigenic variant, termed NGC-V2. The PRNT$_{50}$ titer of NGC-V2 was >70 μg/ml, compared to that of parental DENV-2 NGC, which was 0.89 μg/ml (FIG. 11B).

Sequence Analysis of DENV-2 Antigenic Variants.

To map the Fab 1A5 epitope, the C-prM-E genes of antigenic variants NGB-V1, NGB-V2 and NGC-V2, and the parental viruses were sequenced. Variant NGB-V1 contained five nucleotide mutations in E, compared to the sequence of parental DENV-2 NGB (Table 8). Only the mutation at nucleotide 951 resulted in an amino acid substitution, Gln for His, at position 317 in E, whereas other nucleotide changes were silent mutations. The E sequence of variant NGB-V2 contained two nucleotide changes: a silent mutation of C to T at nucleotide 222, which was also present in NGB-V1, and a G to T mutation at position 317 that resulted in substitution of Val for Gly at position 106. Nucleotide changes were not found in the C-prM genes of variant NGB-V1 or NGB-V2. Variant NGC-V2 contained only a G to T change at nucleotide 317 in E that resulted in substitution of Val for Gly at position 106, identical to that found in NGB-V2. FIG. 12 shows alignment of the flavivirus E sequences surrounding $Gly_{106}$ (panel A) and $His_{317}$ (panel B). $Gly_{106}$ is located within the 12-amino acid fusion peptide sequence (positions 98-109) that is nearly conserved among the arthropod-borne flaviviruses. $His_{317}$ in E is also conserved among flaviviruses, although the surrounding sequences varied. In the 3-D structure, $Gly_{106}$ is located in the cd loop at the tip of domain II and $His_{317}$ is located between β-sheets A and B in domain III (FIGS. 13A and 13B). Despite their locations in different domains, $Gly_{106}$ and $His_{317}$ of the opposite E monomer are spatially close, approximately 16 Å apart, calculated with Swiss Model (Guex, N., and M. C. Peitsch 1997 *Electrophoresis* 18:2714-2723).

Neutralization of DENV-2/DENV-4 Chimeras by Fab 1A5.

Sequence analysis of antigenic variants indicated that Fab 1A5 appeared to recognize a novel epitope involving two closely spaced amino acids in different domains and from two interacting homodimers of DENV-2 E. The antigenic variants containing these mutations differed from the parent viruses in their Fab 1A5 neutralization titer. To provide additional evidence, we constructed DENV-2/DENV-4 chimeras composed of the parental DENV-2 NGB C-prM-E sequence or the variant C-prM-E sequence specifying the $His_{317}$-Gln or $Gly_{106}$-Val substitution present in NGB-V1 and NGB-V2, respectively, on the DENV-4 genetic background. As predicted, Fab 1A5 neutralized the chimeric DENV-2 (NGB-P)/DENV-4 at a $PRNT_{50}$ titer of 0.64 µg/ml, similar to that measured for parental DENV-2 NGB. Substitution of $Gly_{106}$Val or $His_{317}$Gln in DENV-2 E of these chimeras conferred resistance to neutralization by Fab 1A5. The chimera containing $Gly_{106}$Val had a $PRNT_{50}$ titer of >70 µg/ml and the chimera containing $His_{317}$Gln had a $PRNT_{50}$ titer of 31.7 µg/ml, similar to that measured for NGB-V2 and NGB-V1, respectively.

Binding Affinity of Fab 1A5 to Antigenic Variants.

To gain an insight into the neutralizing mechanism, the Fab 1A5 binding activity of the DENV-2 NGB parent virus and its variants was first analyzed by Western blotting. Mab 3H5, which had been shown to recognize an epitope at or near positions 383-385 of DENV-2 E (Hiramatsu, K. et al. 1996 *Virology* 224:437-445), was used for comparison. Mab 3H5 reacted to the DENV-2 NGB parent, variant NGB-V1, NGB-V2, and each of the chimeras similarly. Under the same conditions, Fab 1A5 reacted with the DENV-2 NGB parent and variant NGB-V1, but not with variant NGB-V2 (FIGS. 14A, top panel). Similarly, binding of Fab 1A5 to the DENV-2 NGB-V1/DENV-4 chimera, but not the DENV-2 NGB-V2/DEN4 chimera was observed (FIG. 14A, bottom panel).

An ELISA was performed to semi-quantify the binding affinity of Fab 1A5 for DENV-2 NGB and its two variants (FIG. 14B and Table 9). The apparent binding affinity ELISA Kd of Fab 1A5 for highly resistant variant NGB-V2 was the lowest among the three viruses. Thus, $Gly_{106}$ represented a major determinant of the Fab 1A5 epitope on the DENV-2 E. On the other hand, the binding affinity of Fab 1A5 for variant NGB-V1 was not appreciably reduced, compared to that for the DENV-2 NGB parent. It is possible that $His_{317}$ represented a minor determinant of the Fab 1A5 epitope and affected Fab 1A5 neutralization through a steric effect.

Disulfide Bridge Dependency of the Fab 1A5 Epitope.

In the DENV-2 E sequence, Fab 1A5 epitope determinant $Gly_{106}$ is followed by $Cys_{105}$, which forms a disulfide bridge with $Cys_{74}$. It was of interest to provide data in support of the requirements of this and other disulfide bridges for functional integrity of the Fab 1A5 epitope. Treatment of DENV-2 NGB with β-mercaptoethanol abolished binding of Fab 1A5, as determined by Western blot analysis. Mab 3H5, which recognizes a conformational epitope on DENV-2 E also failed to bind DENV-2 NGB that was similarly treated.

Reactivity of Fab 1A5 to an Oligopeptide Containing the Fusion Peptide Sequence.

Figure 15:
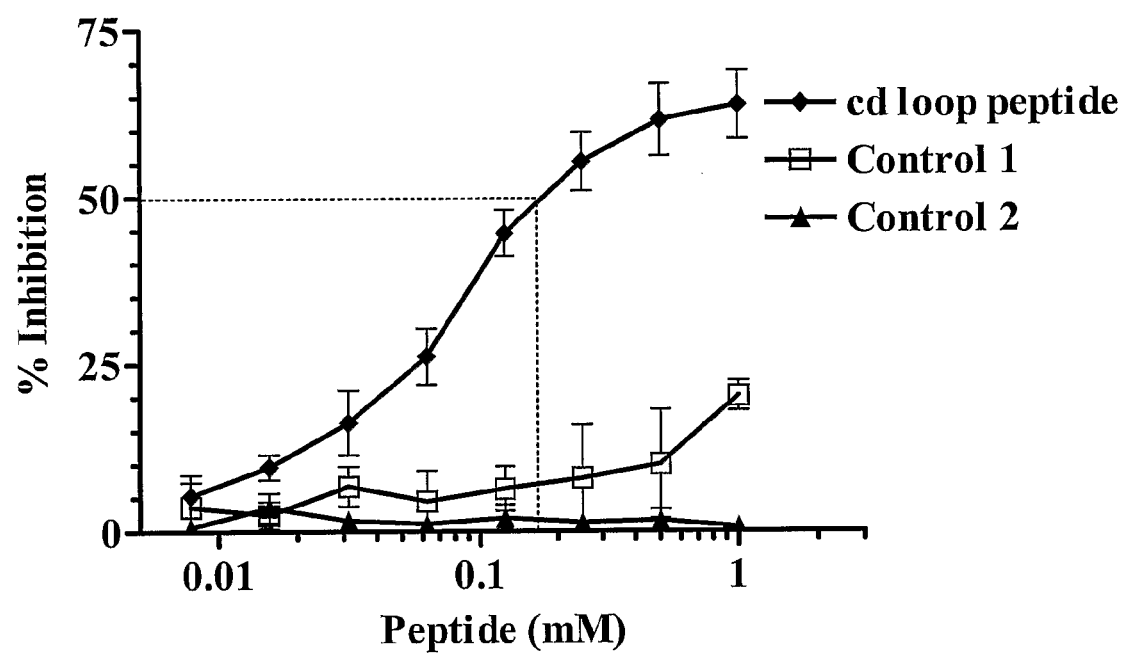
FIG. 15. Inhibition of Fab 1A5 binding to DENV-2 by a fusion peptide. In the binding competition assay, Fab 1A5 was mixed with serial dilutions of an oligopeptide containing the entire fusion peptide sequence (cd loop peptide) or a control peptide with an unrelated sequence. The mixtures were tested for binding to DENV-2 coated on an ELISA plate.

Two separate assays were performed to detect the reactivity of Fab 1A5 with oligopeptides bearing the fusion peptide sequence or unrelated sequences. Binding of Fab 1A5 to each of these oligopeptides immobilized on wells of a microtiter plate was not detected. Competition binding was then performed in which Fab 1A5 was allowed to bind the individual oligopeptides in solution prior to testing for binding to DENV-2. The result in FIG. 15 indicates that binding of Fab 1A5 to DENV-2 was competed by the fusion peptide sequence at the 50% inhibitory concentration of 0.17 mM, whereas each of the two control peptides containing unrelated sequences failed to compete, or only poorly. The concentration of Fab 1A5 used in the inhibition assay was as low as 1.04 nM. One interpretation of this result is that the oligopeptide in solution was able to assume the conformation that is required for binding to Fab 1A5, but rather inefficiently.

Growth Analysis of DENV2 NGB Antigenic Variants.

Four days after infection of Vero cells, parental DENV-2 NGB, DENV-2 NGC and variant NGBV-1 containing $His_{317}$Gln substitution produced plaques similar in size, averaging 1.2±0.2, 1.3±0.1, and 1.1±0.2 mm, respectively. Under the same conditions, variant NGB-V2 and NGC-V2 containing the $Gly_{106}$Val substitution produced plaques of 0.4±0.1 and 0.6±0.1 mm, respectively, appreciably smaller than their parental virus. The growth kinetics of variant NGB-V1 and its parental virus were similar in C6/36 cells and in Vero cells (FIGS. 16A and 16B). On the other hand, variant NGB-V2 consistently yielded a titer ten-fold lower than its parental virus in C6/36 cells and in Vero cells during the log-phase period, i.e., at 3, 4 and 5 days after infection. Similarly, $Gly_{106}$Val substitution reduced replication of DENV-2/DENV-4 chimeras in C6/36 and Vero cells (FIGS. 16C and 16D). The chimera containing $His_{317}$Gln replicated to a level that was comparable to that of NGB-V1 in C6/36 cells. For reasons not understood, the chimeras containing $His_{317}$Gln failed to replicate in Vero cells. Thus, Fab 1A5 selected antigenic variants that were attenuated, or at least, similar to the parental virus for growth in mammalian or insect cells.

Mouse Neurovirulence of DENV-2 Antigenic Variants.

Mouse neurovirulence of the DENV-2 NGB antigenic variants was evaluated by intracranial inoculation of three-day-old outbred Swiss mice. Mice infected with the DENV-2 NGB parent developed symptoms of encephalitis and eventually succumbed to infection. Table 10 shows that the $LD_{50}$ of variant NGB-V1 was 8.9 pfu, not significantly different from the $LD_{50}$ of 4.5 pfu calculated for the parental virus. The $LD_{50}$ of variant NGB-V2 at 16.4 pfu was significantly lower than that of the parental virus, indicating that the variant containing $Gly_{106}$Val substitution was attenuated.

Fusion Activity of DENV-2 Antigenic Variants.

Since the mutation site of variant NGB-V2 was mapped within the flavivirus-conserved fusion peptide loop, the attenuating phenotype of the variant might be associated with alteration of membrane fusion. Initially, the fusion activity of the DENV-2 NGB parent and its variants was examined on infected C6/36 cells. Syncytium formation of the cell monolayer was evident 2 days after infection with parental DENV-2 NGB. At 4 to 5 days after infection, cells of the entire monolayer formed syncytia and the cytopathic effect was extensive. In contrast, formation of syncytium was not observed on cells infected with either NGB-V1 or NGB-V2 under the same conditions, and the cytopathic effect was not seen till 7 days of infection. Reduced fusion of C6/36 cells infected with the DENV-2/DENV-4 chimeras containing the amino acid substitution present in NGB-V1 or NBG-V2 was also evident, compared to cells infected with the chimera containing the parental sequence.

Figure 17:
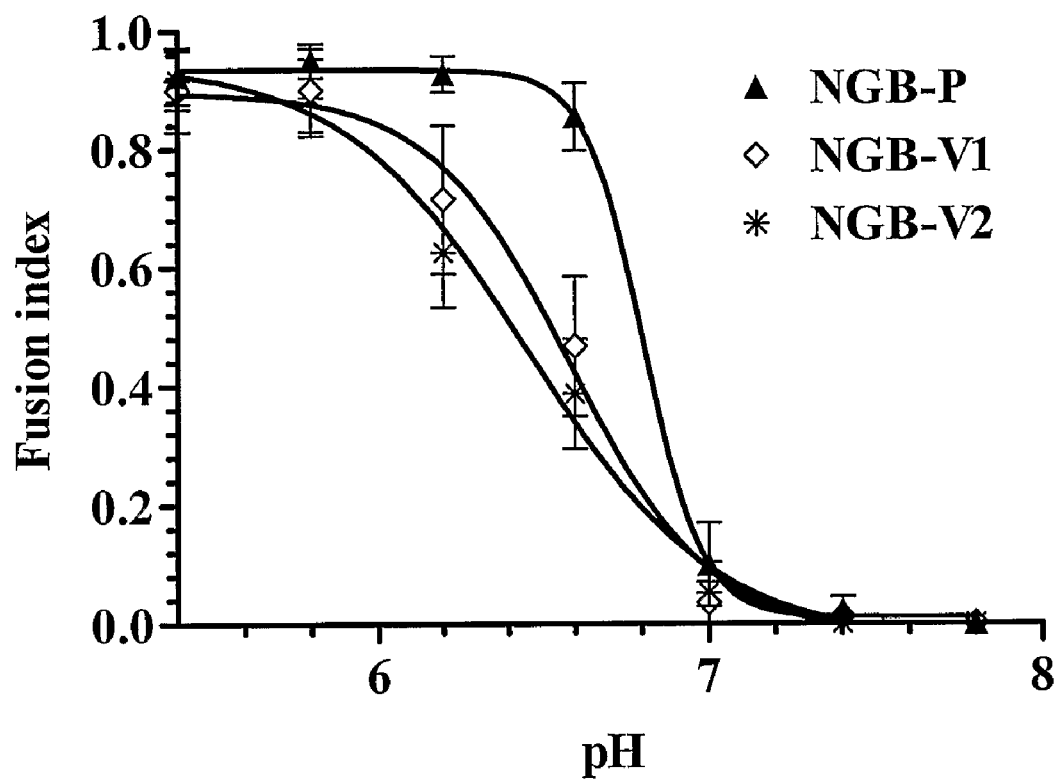
FIG. 17. Fusion activity of DENV-2 NGB parent or its variants. Fusion from within assay was performed on C6/36 cells infected with each of the viruses at 0.2 moi for four to five days at 32° C. The fusion activity of infected cells in the fusion medium at various pHs was detected by syncytium formation. The fusion index was calculated to determine the pH threshold for each virus.

We also studied fusion of C6/36 cells infected with DENV-2 NGB and its antigenic variants at various pH's using the FFWI assay. Little or no fusion was observed at pH 7.0, 7.4 and 7.8. At pH 6.8, approximately 84% of the cells infected with parental DENV-2 formed syncytia. In contrast, 37% of cells infected with variant NGB-V1 and 46% of cells infected with variant NGB-V2 formed syncytia. FIG. 17 shows the fusion activity in terms of the index (FD) for the DENV-2 NGB parent and its variants determined at various pH's. Accordingly, the DENV-2 NGB parent had a pH threshold for 50% maximum fusion activity (FI=0.5) at pH 6.77; variant NGB-V1 at pH 6.55; and variant NGB-V2 at pH 6.41.

Neutralizing Activity of Fab 1A5 Against DENV-4 Mutants Containing $Gly_{106}Val$ or $Leu_{107}Phe$ Substitution in the Fusion Loop.

Alignment of the flavivirus fusion sequences indicates JEV SA 14-14-2 contains a substitution of Phe for Leu at position 107, and Langat virus (LGTV) a His substituting for Gly at position 104 (FIG. 12). The neutralizing activity of Fab 1A5 against JEV SA 14-14-2 and LGTV was the lowest among the flaviviruses tested (Crill, W. D., and J. T. Roehrig 2001 *J. Virol.* 75:7769-7773). We questioned if substitution of $Leu_{107}Phe$ or $Gly_{104}His$ contributed to the resistance of these viruses to Fab 1A5 neutralization. The question of whether $Gly_{106}$ represented a determinant of the Fab 1A5 epitope on DENV-4 E was also raised.

To address the above questions in aggregate, full-length DENV-4 DNA was used to construct mutants containing various substitutions in the fusion peptide for analysis. DENV-4 mutants containing either $Gly_{106}Val$ or $Leu_{107}Phe$ were successfully constructed, however, a DENV-4 mutant containing the $Gly_{104}His$ substitution was apparently not viable. FIG. 18A shows the binding of Fab 1A5 to the DENV-4 parent and mutants containing a $Leu_{107}Phe$ or $Gly_{106}Val$ substitution. Fab 1A5 for the DENV-4 mutant containing $Gly_{106}Val$ had a binding affinity of ELISA Kd>40 nM, significantly reduced as compared to the DENV-4 parent (ELISA Kd=0.65 nM; P<0.0001). Similarly, substitution of $Leu_{107}Phe$ in DENV-4 lowered the binding affinity of Fab 1A5 to an ELISA Kd at 3.07±0.27 nM, p<0.001. FIG. 18B presents Fab 1A5 neutralization of the DENV-4 parent and mutants. The $PRNT_{50}$ titer of parental DENV-4, mutant $Gly_{106}Val$, and mutant $Leu_{107}Phe$ was 4.3 µg/ml, >50 µg/ml, and approximately 50 µg/ml, respectively. The neutralizing titer of Fab1A5 against each of the DENV-4 mutants was greatly reduced compared to that against DENV-4. These observations indicate that both $Gly_{106}$ and $Leu_{107}$ are Fab 1A5 epitope determinants on DENV-4 E.

TABLE 8

Nucleotide and amino acid changes in the E proteins of antigenic variants as compared to their parental viruses.

| Variant | Nucleotide change | Amino acid change | Domain |
|---|---|---|---|
| NGB-V1[1] | $^{222}C \to T$ | No | |
| | $^{402}T \to C$ | No | |
| | $^{468}A \to G$ | No | |
| | $^{526}A \to G$ | No | |
| | $^{951}T \to A$ | $^{317}His \to Gln$ | III |
| | $^{222}C \to T$ | No | |
| NGB-V2[1] | $^{222}C \to T$ | No | |
| | $^{317}G \to T$ | $^{106}Gly \to Val$ | II |
| NGC-V2[2] | $^{317}G \to T$ | $^{106}Gly \to Val$ | II |

[1]No amino acid changes were found in the C-PreM region.

[2]A substitution of Ala for Thr at position 280, the last amino acid of prM, was found.

TABLE 9

Apparent binding affinities of Fab 1A5 for parental DENV-2 NGB and its variants.

| DENV-2 | ELISA Kd (nM) | Affinity Reduction (fold) |
|---|---|---|
| NGB-P | 0.47 ± 0.18 | |
| NGB-V1 | 0.75 ± 0.31 | 1.60 |
| NGB-V2 | 37.75 ± 1.11 | 80.32 |

NGB-P indicates parental DENV-2 NGB.

TABLE 10

Neurovirulence of parental DENV-2 NGB and its variants following ic inoculation in suckling Swiss mice.

| | Mortality of mice after ic inoculation with the indicated virus at pfu of | | | Mean $LD_{50}$ ± |
|---|---|---|---|---|
| Virus | 100 | 10 | 1 | SE (pfu) |
| NGB-P | 20/20 (100%) | 19/21 (90.5%) | 3/10 (30%) | 4.52 ± 0.07 |
| NGB-V1 | 19/20 (95%) | 14/20 (70%) | 2/10 (20%) | 8.9 ± 3.6* |
| NGB-V2 | 18/18 (100%) | 9/19 (47.4%) | 2/10 (20%) | 16.4 ± 0.28** |

NGB-P indicates parental DENV-2 NGB.
The mortality rates at 100 pfu and 10 pfu are based on the cumulative numbers of two experiments.
*P = 0.23;
**P = 0.0065.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A monoclonal antibody, or binding fragment thereof that binds dengue type 4 virus, comprising:
   a heavy chain CDR1 polypeptide having the amino acid sequence of SEQ ID NO: 3, a heavy chain CDR2 polypeptide having the amino acid sequence of SEQ ID NO: 5 and a heavy chain CDR3 polypeptide having the amino acid sequence of SEQ ID NO: 7; and
   a light chain CDR1 polypeptide having the amino acid sequence of SEQ ID NO: 11, a light chain CDR2 polypeptide having the amino acid sequence of SEQ ID NO: 13 and a light chain CDR3 polypeptide having the amino acid sequence of SEQ ID NO: 15.

2. The antibody or binding fragment of claim 1 wherein said binding fragment comprises an Fv fragment.

3. The antibody or binding fragment of claim 1 wherein said binding fragment comprises an Fab fragment.

4. The antibody or binding fragment of claim 1 wherein said antibody is a fully human monoclonal antibody.

5. The antibody or binding fragment of claim 1, wherein said antibody is a humanized chimpanzee monoclonal antibody.

6. The antibody or binding fragment of claim 1, wherein the antibody or binding fragment neutralizes DENV-4 strains from different geographical origins.

7. The antibody or binding fragment of claim 1, wherein the antibody or binding fragment comprises a heavy chain polypeptide having the amino acid sequence of SEQ ID NO: 1.

8. The antibody or binding fragment of claim 1, wherein the antibody or binding fragment comprises a light chain polypeptide having the amino acid sequence of SEQ ID NO: 9.

9. The antibody or binding fragment of claim 1, wherein said antibody or binding fragment neutralizes dengue type 4.

10. An isolated nucleic acid molecule having a nucleotide sequence encoding a heavy chain polypeptide comprising SEQ ID NO:1.

11. An isolated nucleic acid molecule having a nucleotide sequence encoding a light chain polypeptide comprising SEQ ID NO:9.

12. A host cell comprising the isolated nucleic acid molecule of claim 10.

13. A host cell comprising the isolated nucleic acid molecule of claim 11.

14. A pharmaceutical preparation comprising
   a pharmaceutically acceptable carrier; and
   the antibody or binding fragment of claim 1.

15. A diagnostic preparation comprising
   a pharmaceutically acceptable carrier; and
   the antibody or binding fragment of claim 1.

16. A method for the treatment of dengue virus disease comprising administering to a patient a therapeutically effective amount of the pharmaceutical preparation of claim 14.

17. A method for prophylaxis against dengue virus disease comprising administering to a patient a prophylactically effective amount of the pharmaceutical preparation of claim 14.

18. A method for the diagnosis of dengue virus disease comprising:
   administering to a patient an effective amount of the diagnostic preparation of claim 15, and
   detecting binding of the antibody as a determination of the presence of dengue virus disease.

19. A method of detecting the presence of dengue virus in a biological sample comprising:
   contacting said sample with the diagnostic preparation of claim 15, and
   assaying binding of the antibody as a determination of the presence of said dengue virus.

20. Humanized IgG1 5H2 plasmid deposited with ATCC as ATCC Accession No. PTA-5662.

21. An isolated humanized chimpanzee monoclonal antibody that neutralizes dengue virus, wherein said antibody is produced by a plasmid having ATCC Accession No. PTA-5662.

22. A substantially pure antibody comprising
   SEQ ID NO.: 3, SEQ ID NO.: 5, SEQ ID NO.: 7, SEQ ID NO.: 11, SEQ ID NO.: 13, and SEQ ID NO.: 15.

23. The substantially pure antibody of claim 22, which is a monoclonal antibody.

24. The substantially pure antibody of claim 23, wherein the monoclonal antibody is fully human.

25. The substantially pure antibody of claim 23, wherein the monoclonal antibody is a humanized chimpanzee monoclonal antibody.

26. A monoclonal antibody or binding fragment thereof that binds to dengue type 4 virus, wherein said antibody or binding fragment comprises a heavy chain polypeptide having the amino acid sequence of SEQ ID NO: 1 and a light chain polypeptide having the amino acid sequence of SEQ ID NO:9.

* * * * *

UNITED STATES PATENT AND TRADEMARK OFFICE
CERTIFICATE OF CORRECTION

PATENT NO. : 7,622,113 B2
APPLICATION NO. : 10/582006
DATED : November 24, 2009
INVENTOR(S) : Lai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 410 days.

Signed and Sealed this

Twenty-sixth Day of October, 2010

David J. Kappos
*Director of the United States Patent and Trademark Office*